US008921546B2

(12) United States Patent
Chao

(10) Patent No.: US 8,921,546 B2
(45) Date of Patent: Dec. 30, 2014

(54) IMIDAZOLOTHIAZOLE COMPOUNDS FOR THE TREATMENT OF DISEASE

(71) Applicant: Ambit Biosciences Corporation, San Diego, CA (US)

(72) Inventor: Qi Chao, San Diego, CA (US)

(73) Assignee: Ambit Biosciences Corporation, San Diego, CA (US)

(*) Notice: Subject to any disclaimer, the term of this patent is extended or adjusted under 35 U.S.C. 154(b) by 0 days.

(21) Appl. No.: 14/033,299

(22) Filed: Sep. 20, 2013

(65) Prior Publication Data

US 2014/0243525 A1 Aug. 28, 2014

Related U.S. Application Data

(60) Continuation of application No. 13/357,477, filed on Jan. 24, 2012, now Pat. No. 8,557,810, which is a continuation of application No. 12/850,557, filed on Aug. 4, 2010, now Pat. No. 8,129,374, which is a division of application No. 11/724,992, filed on Mar. 16, 2007, now Pat. No. 7,820,657.

(60) Provisional application No. 60/743,543, filed on Mar. 17, 2006.

(51) Int. Cl.
 *C07D 513/04* (2006.01)
(52) U.S. Cl.
 CPC .................................... *C07D 513/04* (2013.01)
 USPC .......................................................... 544/133
(58) Field of Classification Search
 USPC ........................................................ 548/151
 See application file for complete search history.

(56) References Cited

U.S. PATENT DOCUMENTS

| | | | |
|---|---|---|---|
| 3,210,370 | A | 10/1965 | Ursprung |
| 3,267,112 | A | 8/1966 | Iwai el al. |
| 3,507,854 | A | 4/1970 | Sumagawa et al. |
| 4,354,970 | A | 10/1982 | Fleischer et al. |
| 4,464,384 | A | 8/1984 | Murase et al. |
| 4,497,817 | A | 2/1985 | Murase et al. |
| 4,880,824 | A | 11/1989 | Press et al. |
| 5,236,952 | A | 8/1993 | Bernauer et al. |
| 5,466,706 | A | 11/1995 | George et al. |
| 5,623,073 | A | 4/1997 | Anisimova et al. |
| 5,639,756 | A | 6/1997 | Anisimova et al. |
| 5,919,799 | A | 7/1999 | Tasaka et al. |
| 6,696,441 | B1 | 2/2004 | Cottam et al. |
| 7,153,873 | B2 | 12/2006 | Gerlach et al. |
| 7,820,657 | B2 | 10/2010 | Bhagwat et al. |
| 8,129,374 | B2 | 3/2012 | Bhagwat et al. |
| 2004/0067991 | A1 | 4/2004 | Greig et al. |
| 2004/0127719 | A1 | 7/2004 | Yang et al. |
| 2005/0074632 | A1 | 4/2005 | Lee et al. |
| 2005/0165024 | A1 | 7/2005 | Milanov et al. |
| 2006/0122178 | A1 | 6/2006 | Cottam et al. |
| 2009/0123418 | A1 | 5/2009 | James |
| 2009/0131426 | A1 | 5/2009 | Bhagwat et al. |

FOREIGN PATENT DOCUMENTS

| | | |
|---|---|---|
| EP | 524 055 A1 | 1/1993 |
| EP | 1 029 854 B1 | 1/2000 |
| EP | 1 047 418 B1 | 7/2005 |
| FR | 2699920 | 7/1994 |
| FR | 2700546 | 7/1994 |
| FR | 2722501 | 1/1996 |
| FR | 2759698 | 8/1998 |
| JP | 56138196 A2 | 10/1981 |
| JP | 57040492 | 3/1982 |
| JP | 57149288 | 9/1982 |
| JP | 05107705 A2 | 4/1993 |
| JP | 7291976 A2 | 7/1996 |
| JP | 11-106340 | 4/1999 |
| JP | 2001048786 | 2/2001 |
| JP | 2001192386 A | 7/2001 |
| WO | WO98/06724 | 2/1998 |
| WO | WO99/40094 | 8/1999 |
| WO | WO00/78726 | 12/2000 |
| WO | WO 01/27119 | 4/2001 |
| WO | WO 03/031587 | 4/2003 |
| WO | WO2004/048368 | 6/2004 |
| WO | WO2004/058758 | 7/2004 |

OTHER PUBLICATIONS

Abignente, et al., "Research on heterocyclic compounds-V," *II Farmaco Edizione Scientifica* (1976), vol. 31, fasc. 12, 880-887.
Achen, et al., "Targeting lymphangiogenesis to prevent tumor metastasis," *British Journal of Cancer* (2006) 94, 1355-1360.
Anisimova, et al., "Imidazo[1,2-a] benzimidazole derivatives, X Nitration of 2,9-disubstituted imidazo [1,2-a] benzimidazole," (1975), *Khimiya Geterotsiklicheskikh Soedinenii*, 258-62.
Bergers, et al., "Benefits of targeting both pericytes and endothelial cells in the tumor vasculature with kinase inhibitors," (2003), *Journal of Clinical Investigation*, vol. 111, No. 9, 1287-1295.
Blume-Jensen, et al., "Oncogenic kinase signalling," (2001), *Nature* vol. 411, 355-365.
Carlomagno, et al., "BAY 43-9006 Inhibition of Oncogenic RET Mutants," (2006), *Journal of the National Cancer Institute*, vol. 98, No. 5, 326-334.
Chernovyants, et al., Spectrochemical characteristics of symmetrical monomethinecyanines based on pyrrolo- and imidazo [1,2-a] benzimidazole, *Urainskii Khimicheskii Zhurnal*, (1992), 58(3), 257-61.
Cools, et al., "A Tyrosine Kinase Created by Fusion of the PDGFRA and FIP1L1 Genes as a Therapeutic Target of Imatinib in Idiopathic Hypereosinophilic Syndrome," (2003), *The New England Journal of Medicine*, vol. 348, No. 13, 1201-1214.
Curtin, et al., "Somatic Activation of KIT in Distinct Subtypes of Melanoma," (2006) *Journal of Clinical Oncology*, vol. 24, No. 26, 4340-4346.

(Continued)

*Primary Examiner* — Laura L. Stockton
(74) *Attorney, Agent, or Firm* — Jones Day

(57) ABSTRACT

Compounds, compositions and methods are provided for modulating the activity of receptor kinases and for the treatment, prevention, or amelioration of one or more symptoms of disease or disorder mediated by receptor kinases.

1 Claim, 1 Drawing Sheet

(56) References Cited

OTHER PUBLICATIONS

Duensing, et al., "Biology of Gastrointestinal Stromal Tumors: KIT Mutations and Beyond," (2004) *Cancer Investigation* vol. 22, No. 1, 106-116.
Fabian, et al., "A small molecule-kinase interation map for clinical kinase inhibitors," (2005) *Nature Biotechnology*, vol. 23, No. 3, 329-336.
Gazit, et al., "Tyrphostins. 5. Potent Inhibitors of Platelet-Drived Growth Factor Receptor Tyrosine Kinase: Structure-Activity Relationships in Quinoxalines, Quinolines, and Indole Tyrphostins," (1996) *J. Med. Chem*, 39, 2170-2177.
De Giorgi, et al., "Imatinib and gastrointestinal stromal tumors: Where do we go from here?," (2005) *Mol Cancer Ther* 4 (3), 495-501.
Glickman, et al., "A Comparison of ALPHAScreen, TR-FRET, and TRF as Assay Methods for FXR Nuclear Receptors," (2002) Journal of Biomolecular Screening, vol. 7, No. 1, 8 pages.
Grin, et al., "Investigations in the imidazole series LXXVIII. Reaction of 2-aminobenzothiazoles with a-Halo Ketones," (1972) *Khimiya Geterotsiklicheskikh Soedinenii*, 1271-4.
Haran-Ghera, et al., "Increased Circulating Colony-Stimulating Factor-1 (CSF-1) in SJL/J Mice with Radiation-Induced Acute Myeloid Leukemia (AML) is Associated With Autocrine Regulation of AML Cells by CSF-1," (1997) *Blood*, vol. 89, No. 7. 2537-2545.
Heinrich, et al., "PDGFRA Activating Mutations in Gastrointestinal Stromal Tumors," (2003) *Science*, vol. 299, 708-710.
Heinrich, "Targeting FLT3 Kinase in Acute Myelogenous Leukemia: Progress, Perils, and Prospects," (2004) *Mini-Reviews in Medicinal Chemistry*, vol. 4, 255-271.
Kacinski, "CSF-1 and Its Receptor in Breast Carcinomas and Neoplasms of the Female Reproductive Tract," (1997) *Molecular Reproduction and Development*, 46:71-74.
Kiyoi, et al., "Clinical Significance of FLT3 in Leukemia," (2005) *International Journal of Hematology*, vol. 82, No. 2, 85-92.
Kohn, et al., "Cell Cycle Control and Cancer Chemotherapy," (1994) *Journal of Cellular Biochemistry*, 54:440-452.
Krasovskii, et al., Synthesis and properties of naphtha[1,2-d]thiazolo[3,2-a]imidazole derivatives, *Farmatsevtichnii Zhurnal (Kiev)*, (1977) (5), 83-4.
Krause, et al., "Tyrosine Kinases as Targets for Cancer Therapy," (2005) *New England Journal of Medicine* 353;2, 172-187.
Kumabe, et al., "Amplification of x-platelet-derived growth factor receptor gene lacking an exon coding for a portion of the extracellular region in a primary brain tumor of glial origin," (1992) *Oncogene*, 7, 627-633.
Levis, et al., "FLT3 Tyrosine Kinase Inhibitors," (2005) *International Journal of Hematology*, vol. 82, No. 2, 100-107.
Magnusson, et al., "Activity of STI571 in chronic myelomonocytic leukemia with a platelet-derived growth factor B receptor fusion oncogene," (2002) *Blood*, vol. 100, No. 3, 1088-1091.
Ostman, et al., "Involvement of Platelet-Derived Growth Factor ni Disease: Development of Specific Antagonists," (2001) *Cancer Research*, vol. 80, 1-38.
Mase, et al., "Imidazo[2,1-b]benzothiazoles. 2.1 New Immunosuppressive Agents," *J. Med. Chem* (1986) 29, 386-394.
Patra, et al., "Derivatives of Imidazole," *J. Indian Chem. Soc.*, vol. L1, (1974) 1031-1034.
Paz, et al., "Development of Angiogenesis Inhibitors to Vascular Endothelial Growth Factor Receptor 2. Current Status and Future Perspective," (2005) *Fronters in Bioscience*, 10, 1415-1439.
Pentimalli, "Substitution and addition reactions of benzo-substituted 2-phenylimidazo [2,1-b] benzothiazoles," (1969) *Gazzetta Chimica Italiana*, 99(4), 362-72, CODEN: GCITA9; ISSN: 0016-5603.
Pietras, et al., "PDGF receptors as cancer drug targets," (2003) *Cancer Cell*, vol. 3, 439-443.
Pietras, et al., "Inhibition of PDGF Receptor Signaling in Tumor Stroma Enhances Antitumor Effect of Chemotherapy," (2002) *Cancer Research*, 62, 5476-5484.
Plowman, et al., "Receptor Tyrosine Kinases as Targets for Drug Intervention," (1994) *Drug News and Perspectives*, vol. 7, No. 6, 334-339.
Rolland, et al., "Increased Blood Myeloid Dendritic Cells and Dendritic Cell-Poietins in Langerhans Cell Histiocytosis," (2005) *The Journal of Immunology*, 174: 3067-3071.
Saharinen, et al., "Double target for tumor mass destruction," (2003) *The Journal of Clinical Investigation*, vol. 111, No. 9, 1277-1280.
Sawhney, et al., "Synthesis & Antiinflammatory Activity of Some Arylimidazo[2,1-b]-thiazolyl- & Aru;o,odazp[2,I-b]benzothiazolyl-acetic Acids," (1982) *Indian Journal of Chemistry*, vol. 21B, 134-138.
Stacker, et al., "Molecular Targeting of Lymphatics for Therapy," (2004) *Current Pharmaceutical Design*, 10:1, 65-74.
Stacker, et al., "Lymphangiogenesis and Cancer Metastasis," (2002) *Nature Reviews—Cancer*, vol. 2, 573-583.
Strock, et al., "CEP-701 and CEP-751 Inhibit Constitutively Activated RET Tyrosine Kinase Activity and Block Medullary Thyroid Carcinoma Cell Growth," (2003) *Cancer Research*, 63, 5559-5563.
Stone, et al., "Reversible, p16-mediated Cell Cycle Arrest as Protection from Chemotherapy," (1996) *Cancer Research*, 56, 3199-3202.
Ursprung, J., "2,2'-Methylenediimidazoles," (1965) *Chemical Abstracts*, vol. 63, 18103-18104.
Vousden, "Interactions of human papillomavirus transforming proteins with the products of tumor suppressor genes," (1993) *FASEB J.*, 7:872-879.
Whartenby, et al., "Inhibitor of FLT3 signaling targets DCs to ameliorate autoimmune disease," (2005) *National Academy of Sciences*, vol. 102, No. 46, 16741-16746.
Yee, et al., "SU5416 and SU5614 inhibit kinase activity of wild-type and mutant FLT3 receptor tyrosine kinase," (2002) *Blood*, vol. 100, No. 8, 2941-2949.
ISA/EP International Search Report dated Oct. 29, 2007 for International Application No. PCT/US2007/006613, filed Mar. 16, 2007.
ISA/EP Written Opinion of the International Searching Authority dated Oct. 29, 2007 for International Application No. PCT/US2007/006613, filed Mar. 16, 2007.
Abignente, et al. (1989) *Journal of Heterocyclic Chemistry* 26(6): 1875-80.
Anisimova, et al. (1976) *Khimiya Geterotsiklicheskikh Soedinenii* 11: 126-134.
Anisimova, et al. (1986) *Khimiya Geterotsiklicheskikh Soedinenii* 3: 339-45.
Anisimova, et al. (1987) *Khimiya Geterotsiklicheskikh Soedinenii* 11: 1496-502.
Balaban, T.S. *Science of Synthesis* (2003) 14 11-200.
Buu-Hot, et al. (1966) *Bulletin de la Societe Chimique de France* 4: 1277-9.
Kandeel, (2001) *Journal of Chinese Chemical Society* 48(1): 37-43.
Kandeel (2002) *Bulletin of the Polish Academy of Science, Chemistry* 50(3) 309-322.
Mase et al. (1987) *Heterocycles* 26(12): 3159-3164.
Palagiano et al. (1996) *Farmaco*, 51(7) 483-491.
Rached et al. (1992) *European Journal of Medicinal Chemistry* 27(4): 425-429.
Office Action mailed Apr. 17, 2009, U.S. Appl. No. 11/724,992.
Office Action mailed Aug. 31, 2009, U.S. Appl. No. 11/724,992.
Notice of Allowance mailed Dec. 30, 2011, U.S. Appl. No. 11/724,992.
Office Action mailed Jun. 8, 2011, U.S. Appl. No. 12/850,557.
Notice of Allowance mailed Oct. 13, 2011, U.S. Appl. No. 12/850,557.
Office Action mailed May 17, 2012, U.S. Appl. No. 13/357,477.
Office Action mailed Dec. 5, 2012, U.S. Appl. No. 13/357,477.
Notice of Allowance mailed Jun. 14, 2013, U.S. Appl. No. 13/357,477.

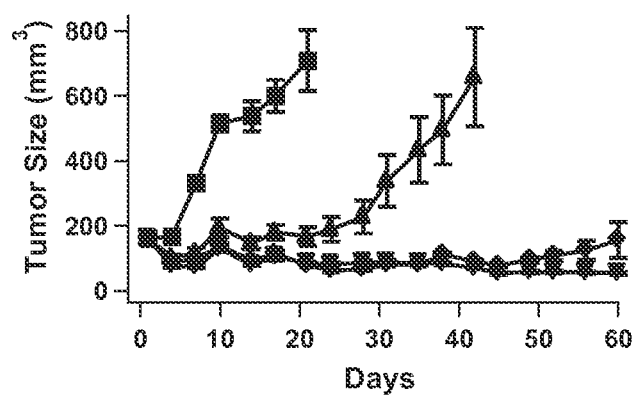

IMIDAZOLOTHIAZOLE COMPOUNDS FOR THE TREATMENT OF DISEASE

This application claims priority under 35 U.S.C. §120 to, and is a continuation of U.S. patent application Ser. No. 13/357,477, filed Jan. 24, 2012, now allowed, which claims priority under 35 U.S.C. §120 to, and is a continuation of U.S. patent application Ser. No. 12/850,557, filed Aug. 4, 2010, now issued as U.S. Pat. No. 8,129,374, which claims priority under 35 U.S.C. §120 to, and is a divisional of, U.S. patent application Ser. No. 11/724,992, filed Mar. 16, 2007, now issued as U.S. Pat. No. 7,820,657, which claims priority to U.S. provisional application Ser. No. 60/743,543, filed Mar. 17, 2006, entitled "Imidazolothiazole Derivatives For The Treatment Of Disease". The disclosures of each of the above referenced applications is incorporated by reference herein in their entireties.

FIELD

New small molecule compounds, compositions and methods for treating disease are provided. The compounds provided are modulators of activity of enzymes, such as kinases, and are useful in the treatment, prevention, or amelioration of a disease or disorder related to enzyme activity or one or more symptoms thereof.

BACKGROUND

Protein kinases (PKs) are enzymes that catalyze the phosphorylation of hydroxy groups on tyrosine, serine and threonine residues of proteins. Protein kinases, and in particular the receptor protein tyrosine kinase (RTK) family of protein kinases, act primarily as growth factor receptors and play a central role in signal transduction pathways regulating a number of cellular functions, such as cell cycle, cell growth, cell differentiation and cell death. Aberrant or excessive activity or the disregulation of activity of receptor protein tyrosine kinase (RPTK) has been observed in many disease states including benign and malignant proliferative disorders as well as inflammatory disorders and immune system disorders that result from inappropriate activation of the immune system to cause, for example, autoimmune diseases.

Disregulated activity of the receptor tyrosine kinase of the platelet growth factor receptor (PDGFR) family, as one example, has been implicated in various proliferative disorders. Gene amplification or upregulation of PDGFR occurs in patients with gliomas or sarcomas (Kumabe et al., *Oncogene*, 7:627-633 (1992), Ostman and Heldin Cancer Res. 80:1-38 (2001)). Constitutive activation of PDGFR-α has been found in patients with chronic myelomonocytic leukemia (CMML) ((Magnusson et al, *Blood* 100:1088-1091 (2002)). Gain of function mutations and small deletions in the PDGFR-α gene has also been found in patients with gastrointestinal tumors (GIST) (Heinrich et al. *Science* 299: 708-710 (2003)) and in patients with idiopathic hypereosinophilic syndrome (Cools et al. *N. Engl. J. Med.* 348:1201-1214 (2003)). PDGFR-β has been found to be expressed in the tumor stroma in a majority of solid tumors, which makes this receptor a potential target for anti-tumor therapy (Pietras et al. Cancer Cell 3:439-443 (2003), Pietras et al. *Cancer Res.* 62: 5476-5484 (2002)), PDGFR-β has also been found to be expressed in tumor vasculature and studies have suggested PDGFR-β inhibition as one mechanism for anti-angiogenic therapy. (See, Bergers et al *J. Clin. Invest.* 111(9): 1287-1295(2003), Saharinen et al. *J. Clin. Invest.* 111:1277-1280 (2003)).

A second member of the PDGFR family, Flt3 (also called Flk2), plays an important role in the proliferation and differentiation of hematopoietic stem cells and activating mutation or overexpression of this receptor is found in AML (See, Heinrich Mini-Reviews in Medicinal Chemistry (2004) 4(3): 255-271, Kiyoi et al. *Int J Hematol* (2005) 82:85-92). More than a dozen known Flt3 inhibitors are being developed and some have shown promising clinical effects against AML (See Levis et al. *Int J Hematol*. (2005) 82:100-107). The Flt3 receptor is also expressed in a large portion of dendritic cell progenitors and stimulation of the receptor causes the proliferation and differentiation of these progenitors into dendritic cells (DC). Since dendritic cells are the main initiators of the T-cell mediated immune response, including the autoreactive immune response, Flt3 inhibition is a mechanism for downregulating DC-mediated inflammatory and autoimmune responses. One study shows the Flt3 inhibitor CEP-701 to be effective in reducing myelin loss in experimental autoimmune encephalomyelitis (EAE), a mouse model for multiple sclerosis (See Whartenby et al. *PNAS* (2005) 102: 16741-16746). A high level of the Flt3 ligand is found in the serum of patients with Langerhans cell histiocytosis and systemic lupus erythematosus, which further implicates Flt3 signaling in the disregulation of dendritic cell progenitors in those autoimmune diseases (See Rolland et al. *J Immunol*. (2005) 174:3067-3071).

A third member of the PDGFR family, colony-stimulating factor-1 receptor (CSF-1R) (also called macrophage colony stimulating factor receptor (M-CSFR) or fms) is expressed by many carcinomas of the breast and human epithelial cancers, especially of the female reproductive tract (Kacinski (1997) *Mol. Reprod. Dev.* 46:71-74) and presents a potential target for cancer therapies. High level of CSF-1 expression in solid tumors and leukemias, also suggests that CSF-1R might be a therapeutic target for blood cancers and solid tumors (Haran-Ghera (1997) *Blood* 89:2537-2545). A high level of CSF-1 expression is also found in Langerhans cell histiocytosis (Rolland et al. *J Immunol*. (2005) 174:3067-3071).

Kit (or stem cell factor receptor, or SCFR) is another member of the PDGFR family, and the presence of kit mutations is a key diagnostic marker for gastrointestinal stromal tumors (GIST) (Duensing et al. (2004) *Cancer Investigation* 22(1): 106-116). Gleevec® (imatinib mesylate or STI571), the first FDA-approved RPTK inhibitor originally approved for c-Abl-mediated chronic myeloid leukemia, gained FDA-approval for Kit-mediated GIST in 2002 and has validated the molecular-based approach of Kit inhibition for the treatment of GIST. (Giorgi and Verweij, *Mol Cancer Ther* 4(3):495-501 (2005)). Gain of function mutations of the Kit receptor are also associated with mast cell myeloid leukemia and seminomas/dysgerminomas (Blume-Jensen *Nature* 411(17): 355-365(2001). Kit mutations have been also identified in certain melanomas and recognized as a potential therapeutic target for melanoma (Curtain et al. *J Clin. Oncol*. 24(26):4340-4346 (2006)).

The vascular endothelial growth factor receptor (VEGFR) represents another family of RTKs, one that is implicated in tumor angiogenesis. VEGF and its receptors VEGFR1 (also called Flt1) and VEGFR2 (also called KDR) are overexpressed in the great majority of clinically important human cancers including cancers of the gastrointestinal tract, pancreas, bladder, kidney, endometrium and in Kaposi's sarcoma. VEGFR2 is also highly expressed in certain intracranial tumors including glioblastoma multiforme and sporadic and von Hippel Landau (VHL) syndrome-associated capillary hemangioblastoma. There are currently more than a dozen VEGFR2 inhibitors in clinical development for anti-angiogenic therapy (Paz and Zhu, *Frontiers in Bioscience* 10:1415-1439 (2005)).

Another member of the VEGFR family, VEGFR3 (also called Flt 4) has been identified as a lymphangiogenic growth factor receptor which play a key role in the growth of new lymphatic vessels (lymphanigiogenesis). Activation of the VEGFR3 signaling pathway has been shown to stimulate metastatic spread of tumor cells (See Stacker et al. *Nature Rev* 2:573-583(2002)) and therefore its inhibition could be the basis for treating conditions characterized by abnormal lymphatic vessel function (See Stacker et al. *Current Pharmaceutical Design* 10:65-74 (2004), Achen et al. *British Journal of Cancer* 94:1355-1360 (2006)).

Ret kinase is yet another RTK, one that is found expressed in medullary thyroid carcinoma, a condition that is part of the multiple endocrine neoplasia 2A and 2B (MENS 2A and 2B) syndromes. Ret is constitutively active in medullary thyroid carcinoma (both familial and sporadic) and in papillary thyroid carcinoma. Some known RTK inhibitors having Ret-inhibitory activity have been shown to be effective in inhibiting tumor growth in nude mouse models (Stock et al., *Cancer Res* 63:5559-5563 (2003)) and Carlomagno et al., *Journal of the National Cancer Institute* 98(5):326-334 (2006)).

It is additionally possible that inhibitors of certain kinases may have utility in the treatment of diseases when the kinase is not misregulated, but is nonetheless essential for maintenance of the disease state. In such cases, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994)).

Finally, while overactivation of RTK signaling pathways is often the underlying mechanism for cancer, impaired deactivation of RTKs such as the impaired down-regulation of RTKs via ligand-induced endocytosis or impaired negative feedback loops, may also be the cause of some malignancies. Another strategy for use of the molecules discussed herein therefore is to repair and promote any existing mechanism for downregulating RTKs.

In view of the large number of protein kinase inhibitors and the multitude of PK-mediated proliferative, inflammatory and immune function diseases, there is an ever-existing need to provide novel classes of compounds that are useful as PK inhibitors and thus in the treatment of PK related diseases, as discussed herein.

SUMMARY

Compounds for use in medical treatment, pharmaceutical compositions and methods for modulating the activity, binding or sub-cellular distribution of kinases are provided. In one embodiment, the compounds for use in the compositions and methods provided herein have formula (I):

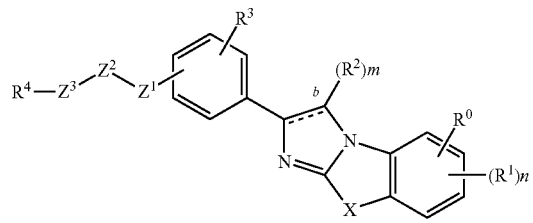

wherein
bond b is a single bond or double bond;
X is —S—, —N($R^5$)— or —O—;
$Z^1$ and $Z^3$ are each independently —N($R^5$)—, —(CH$_2$)$_q$, —O—, —S—, or a direct bond;
$Z^2$ is —C(O)— or —C(S)—;
m is an integer from 1 to 2;
n is an integer from 1 to 3;
each q is independently an integer from 1 to 4;
$R^0$ is hydrogen, halo, hydroxy, optionally substituted alkyl, or optionally substituted alkoxy;
each $R^1$ is independently selected from the group consisting of halo, optionally substituted alkyl, optionally substituted alkenyl, optionally substituted alkynyl, optionally substituted heterocyclylalkyl, optionally substituted heterocyclylalkenyl, optionally substituted heteroaralkyl, optionally substituted heteroaralkenyl, —$R^6OR^7$, —$R^6SR^7$, —$R^6S(O)_tR^8$ (where t is 1 or 2), —$R^6N(R^7)_2$, —$R^6OR^9OR^7$, —$R^6CN$, —$R^6C(O)R^7$, —$R^6C(S)R^7$, —$R^6C(NR^7)R^7$, —$R^6C(O)OR^7$, —$R^6C(S)OR^7$, —$R^6C(NR^7)OR^7$, —$R^6C(O)N(R^7)_2$, —$R^6C(S)N(R^7)_2$, —$R^6C(NR^7)N(R^7)_2$, —$R^6C(O)N(R^7)R^9N(R^7)_2$, —$R^6C(O)SR^8$, —$R^6C(S)SR^8$, —$R^6C(NR^7)SR^8$, —$R^6S(O)_tOR^7$ (where t is 1 or 2), —$R^6S(O)_tN(R^7)_2$ (where t is 1 or 2), —$R^6S(O)_tN(R^7)N(R^7)_2$ (where t is 1 or 2), —$R^6S(O)_tN(R^7)N=C(R^7)_2$, —$R^6S(O)_tN(R^7)C(O)R^8$ (where t is 1 or 2), —$R^6S(O)_tN(R^7)C(O)N(R^7)_2$ (where t is 1 or 2), —$R^6S(O)_tN(R^7)C(NR^7)N(R^7)_2$ (where t is 1 or 2), —$R^6N(R^7)C(O)R^8$, —$R^6N(R^7)C(O)OR^8$, —$R^6N(R^7)C(O)SR^8$, —$R^6N(R^7)C(NR^7)SR^8$, —$R^6N(R^7)C(S)SR^8$, —$R^6N(R^7)C(O)N(R^7)_2$, —$R^6N(R^7)C(NR^7)N(R^7)_2$, —$R^6N(R^7)C(S)N(R^7)_2$, —$R^6N(R^7)S(O)_tR^8$ (where t is 1 or 2), —$R^6OC(O)R^8$, —$R^6OC(NR^7)R^8$, —$R^6OC(S)R^8$, —$R^6OC(O)OR^6$, —$R^6OC(NR^7)OR^8$, —$R^6OC(S)OR^8$, —$R^6OC(O)SR^8$, —$R^6OC(O)N(R^7)_2$, —$R^6OC(NR^7)N(R^7)_2$, —$R^6OC(S)N(R^7)_2$, —$R^6OR^9N(R^7)_2$, —$R^6SR^9N(R^7)_2$, —$R^6N(R^7)R^9N(R^7)_2$, —$R^6C(O)R^9C(O)R^7$, —$R^6C(O)R^9C(S)R^7$, —$R^6C(O)R^9C(NR^7)R^7$, —$R^6C(O)R^9C(O)OR^7$, —$R^6C(O)R^9C(S)OR^7$, —$R^6C(O)R^9C(NR^7)OR^7$, —$R^6C(O)R^9C(O)N(R^7)_2$, —$R^6C(O)R^9C(S)N(R^7)_2$, —$R^6C(O)R^9C(NR^7)N(R^7)_2$, —$R^6C(O)R^9C(O)SR^8$, —$R^6C(O)R^9C(S)SR^6$, —$R^6C(O)R^9C(NR^7)SR^8$, —$R^6C(O)$, —$R^6C(O)R^9N(R^7)R^9N(R^7)_2$, —$R^6C(O)R^9N(R^7)R^9OR^7$ and —$R^6C(O)N(R^7)R^9OR^7$;

each $R^2$ is independently selected from hydrogen, halo, nitro, cyano, optionally substituted alkyl, —$OR^{12}$, —$SR^{12}$, —$N(R^{12})_2$, —$S(O)_tR^{13}$ (where t is 1 or 2), —$C(O)R^{12}$, —$C(O)OR^{12}$, —$C(O)N(R^{12})_2$, —$C(O)SR^{12}$, or —$N(R^{12})S(O)_tR^{13}$ (where t is 1 or 2);

$R^3$ is hydrogen, halo, nitro, cyano, optionally substituted alkyl, —$OR^{12}$, —$SR^{12}$, —$N(R^{12})_2$, —$S(O)_tR^{13}$ (where t is 1 or 2), —$C(O)R^{12}$, —$C(O)OR^{12}$, —$C(O)N(R^{12})_2$, —$C(O)SR^{12}$, or —$N(R^{12})S(O)R^{13}$ (where t is 1 or 2);

$R^4$ is selected from the group consisting of optionally substituted alkyl, optionally substituted heterocyclyl, optionally substituted heteroaryl, optionally substituted cycloalkyl, optionally substituted cycloalkenyl and optionally substituted aryl;

each $R^5$ is independently hydrogen, or optionally substituted alkyl;

each $R^6$ is independently a direct bond, an optionally substituted straight or branched alkylene chain, or an optionally substituted straight or branched alkenylene chain;

each $R^7$ is independently selected from (i) or (ii) below (i) $R^7$ is selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl, or (ii) two ($R^7$)s together with the atom to which they are attached form an optionally substituted heterocyclyl or optionally substituted heteroaryl;

$R^8$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;

each $R^9$ is independently an optionally substituted straight or branched alkylene chain or an optionally substituted straight or branched alkenylene chain;

each $R^{12}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and $R^{13}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl.

In one embodiment, the compound is selected with the proviso that, (i) if —$Z^1Z^2Z^3R^4$ is —NHC(O)Bu then $R^1$ may not be ethoxy;

(ii) if —$Z^1Z^2Z^3R^4$ is —C(O)OR$_p$, where R$_p$=methyl, or ethyl, then $R^1$ may not be hydroxyl, methoxy or methoxycarbonyl;

(iii) if —$Z^1Z^2Z^3R^4$ is —NHC(O)C(O)OR$_p$, where R$_p$=methyl, or ethyl, then $R^1$ may not be methoxy;

(iv) if —$Z^1Z^2Z^3R^4$ is —CH$_2$C(O)OR$_p$, where R$_p$=methyl, or ethyl, then $R^1$ may not be methoxy or ethoxy;

(v) if —$Z^1Z^2Z^3R^4$ is —OC(O)CH$_3$, then $R^1$ may not be methyl, methoxy or ethoxy;

as a single isomer, a mixture of isomers, a racemic mixture of isomers, a solvate, a hydrate or a prodrug, or as a pharmaceutically acceptable salt thereof.

In one embodiment, the compound provided herein is a pharmaceutically acceptable salt of the compound of formula (I). In one embodiment, the compounds provided herein is a solvate of the compound of formula (I). In one embodiment, the compounds provided herein is a hydrate of compound of formula (I). In one embodiment, the compound provided herein is a prodrug of the compound of formula (I).

Such compounds can bind to one or more kinases with high affinity and modulate their activity. In certain embodiment, such compounds exhibit an EC$_{50}$, IC$_{50}$ or binding affinity of less than 1 μM, and in certain embodiments, less than about 0.5 μM, 250 nM, 100 nM or 50 nM. In one aspect, the compounds provided herein are selective for a specific kinase, or specific subset of kinases, i.e. are at least 5, 10, or in another aspect, at least 20, 50, 100 times more potent, as measured by any of the in vitro assays described herein, in binding to the desired kinase(s) compared to a non preferred kinase or kinases. In one aspect, the compounds selectively inhibit the desired kinase(s) without significant effect on the non desired kinase(s).

Also provided are pharmaceutical compositions formulated for administration by an appropriate route and means containing effective concentrations of one or more of the compounds provided herein, or pharmaceutically acceptable salts, solvates, hydrates and prodrugs thereof, and optionally comprising at least one pharmaceutical carrier, excipient, vehicle, binder, diluent, disintegrating agent, lubricant, glidant, sweetening agent or flavoring agent.

Such pharmaceutical compositions deliver amounts effective for the treatment, prevention, or amelioration of diseases or disorders that are modulated or otherwise affected by protein kinases (PK related diseases) or one or more symptoms or causes thereof. Such diseases or disorders include without limitation:

A) Cancers, including, but not limited to head and neck cancer, (originating lip, oral cavity, oropharynx, hypopharynx, larynx, nasopharynx, nasal cavity and paranasal sinuses, salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of vater; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, prostate cancer, penile cancer, urethral cancer; neurologic tumors; endocrine neoplasms, including carcinoid and islet cell tumors, pheochromocytoma, adrenal cortical carcinoma, parathyroid carcinoma and metastases to endocrine glands.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer In one embodiment, cancer comprises various types of leukemias such as chronic lymphocytic leukemia, chronic myelocytic leukemia, acute lymphoblastic leukemia, acute myelogenous leukemia and acute myeloblastic leukemia.

In some embodiments, acute leukemia includes, but is not limited to undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7). In some embodiments, acute lymphocytic leukemia (ALL) includes leukemia that originates in the blast cells of the bone marrow (B-cells), thymus (T-cells) and lymph nodes. The acute lymphocytic leukemia is categorized as L1—Mature-appearing lymphoblasts (T-cells or pre-B-cells), L2—Immature and pleomorphic (variously shaped) lymphoblasts (T-cells or pre-B-cells) and L3—Lymphoblasts (B-cells; Burkitt's cells).

In one embodiment, cancer is cancer of stomach, gastric, bone, ovary, colon, lung, brain, larynx, lymphatic system, genitourinary tract, squamous cell carcinoma, astrocytoma, Kaposi's sarcoma, glioblastoma, lung cancer, bladder cancer, head and neck cancer, melanoma, prostate cancer, breast cancer, small-cell lung cancer, leukemia, glioma, colorectal cancer, genitourinary cancer, gastrointestinal cancer, hematologic cancer or pancreatic cancer. In particular, acute myelogenous leukemia (AML), B-precursor cell acute lymphoblastic leukemias, myelodysplastic leukemias, T-cell acute lymphoblastic leukemias and chronic myelogenous leukemias (CMLs).

The cancers to be treated herein may be primary or metastatic. In one embodiment, the cancer is a solid or blood born metastatic tumor. In another embodiment, the cancer is metastatic cancer of bone.

B) Nonmalignant proliferation diseases; atherosclerosis, restenosis following vascular angioplasty and fibroproliferative disorders such as obliterative bronchiolitis.

C) Inflammatory diseases or disorders related to immune dysfunction, including, immunodeficiency, immunomodulation, autoimmune diseases, tissue rejection, wound healing, kidney disease, allergies, inflammatory bowel disease, Lupus Erythematosis, arthritis, osteoarthritis, rheumatoid arthritis, asthma and rhinitis.

D) infectious diseases mediated either via viral or bacterial pathogens.

Compositions and methods for treating a disease comprising administering to a subject an effective amount of a Kit or stem cell factor receptor (SCFR) modulating compound are provided herein. In one embodiment, the disease is cancer. In another embodiment, the disease is carcinoma. In some embodiments, the cancer is small-cell lung cancer, or breast cancer. In another embodiment, the disease is prostate carcinoma. In yet another embodiment, the cancer is endometrial cancer. In another embodiment, the cancer is glioma. In other embodiments, the cancer is a malignant tumor, or a hematologic malignancy such as leukemia and lymphoma. In some embodiments, the leukemia is acute myelogenous leukemia (AML). In some embodiment, the leukemia is mast cell leukemia. In another embodiment, the disease is systemic mastocytosis. In yet another embodiment, the disease is myelodysplastic syndrome (MDS). In some embodiments, the malignant tumor is a germ cell tumor. In another embodiment, the germ cell tumor is semiomas and/or dysgerminomas. In yet another embodiment, the disease is gastrointestinal stromal tumor (GIST). In yet another embodiment, the disease is mast cell tumor, a, melanoma, or a neuroblastoma.

Compositions and methods for treating a disease comprising administering to a subject in need thereof an effective amount of a Platelet-Derived Growth Factor (PDGF) receptor modulating compound are provided herein. In one embodiment, the disease is cancer. In another embodiment, the disease is carcinoma. In another embodiment, the carcinoma is ovarian carcinoma. In yet another embodiment, the carcinoma is breast carcinoma. In another embodiment, the carcinoma is renal cell carcinoma. In yet another embodiment, the disease is sarcoma. In other embodiments, the cancer is a malignant tumor, or a hematologic malignancy such as leukemia and lymphoma. In some embodiments, the leukemia is acute lymphoblastic leukemia (ALL). In another embodiment, the leukemia is chronic myelogenous leukemia (CML). In some embodiments, the lymphoma is T-cell lymphoma. In another embodiment, the disease is idiopathic hypereosinophilic syndrome (HES). In another embodiment, the disease is chronic eosinophilic leukemia (CEL). In some embodiments, the malignant tumor is melanoma, or glioblastoma. In another embodiment, the disease is tumor angiogenesis. In a further embodiment, the disease is a nonmalignant proliferation disease. In some embodiments, the nonmalignant proliferation disease is atherosclerosis, or restenosis. In a still further embodiment, the disease is a fibroproliferative disorder. In some embodiments, the fibroproliferative disorder is obliterative bronchiolitis. In another embodiment, the fibroproliferative disorder is idiopathic myelofibrosis.

Compositions and methods for treating a disease comprising administering to a subject in need thereof an effective amount of a Flt-3 receptor modulating compound are provided herein. In one embodiment, the disease is cancer. In another embodiment, the disease is carcinoma. In some embodiments, the cancer is small-cell lung cancer, or breast cancer. In other embodiments, the cancer is a malignant tumor, or a hematologic malignancy such as leukemia and lymphoma. In another embodiment, the disease is a hematologic malignance such as leukemia and/or lymphoma. In some embodiments, the leukemia is acute myelogenous leukemia (AML) or is chronic myeloid leukemia (CML). In some embodiments, the cancer is acute lymphoblastic leukemia (ALL), myelodysplastic leukemia, T-cell acute lymphoblastic leukemia, and B-cell acute lymphoblastic leukemia. In another embodiment, the disorder is the myelodysplastic syndrome. In yet another embodiment, the disease is an immune system disorder and/or inflammatory disease. In another embodiment, the immune system disorder is systemic lupus erythematosis. In another embodiment, the immune system disorder is inflammatory bowel disease. In another embodiment, the inflammatory bowel disease is Crohn's disease and/or ulcerative colitis. In another embodiment, the immune system disorder is chronic obstructive pulmonary disease.

Compositions and methods for treating a disease comprising administering to a subject in need thereof an effective amount of VEGFR-modulating compound are provided herein. In one embodiment, the disease is cancer. In another embodiment, the disease is carcinoma. In another embodiment, the disease is solid tumor. In another embodiment, the disease is metastatic tumor. In another embodiment, the disease is stromal tumors. In yet another embodiment, the disease is neuroendocrine tumors. In yet another embodiment, the disease or disorder is tumor angiogenesis. In another embodiment, the disease is sarcoma. In another embodiment, the sarcoma is Kaposi's sarcoma, hemangiosarcoma and/or lymphangiosarcoma.

Compositions and methods for treating a disease comprising administering to a subject in need thereof an effective amount of CSF-1R- (or fms-) modulating compound are provided herein. In one embodiment, the disease is cancer. In another embodiment, the disease is carcinoma. In yet another embodiment, the disease is metastatic tumor. In another embodiment, the metastatic tumor is metastases to the bone. In yet another embodiment, the disease is Langerhans cell histiocytosis. In yet another embodiment, the disease is an immune system disorder and/or inflammatory disease. In another embodiment, the immune system disorder is systemic lupus erythematosis. In another embodiment, the immune system disorder is inflammatory bowel disease. In another embodiment, the inflammatory bowel disease is Crohn's disease and/or ulcerative colitis. In another embodiment, the immune system disorder is rheumatoid arthritis. In yet another embodiment, the immune system disorder is multiple sclerosis. In yet another embodiment, the immune system disorder is systemic lupus erythematosis. In yet another embodiment, the immune system disorder is allergic rhinitis and/or asthma. In another embodiment, the immune system disorder is type 1 diabetes.

Compositions and methods for treating a disease comprising administering to a subject in need thereof an effective amount of Ret-modulating compound are provided herein. In one embodiment, the disease is cancer. In another embodiment, the disease is carcinoma. In yet another embodiment, the carcinoma is thyroid carcinoma. In yet another embodiment, the thyroid carcinoma is sporadic or familial medullary carcinoma. In another embodiment, the thyroid carcinoma is papillary thyroid carcinoma. In yet another embodiment, the thyroid carcinoma is parathyroid carcinoma. In another embodiment, the disease is multiple endocrine neoplasia 2A or 2B.

Also contemplated herein are combination therapies using one or more compounds or compositions provided herein, or pharmaceutically acceptable derivatives thereof, in combination with other pharmaceutically active agents for the treatment of the diseases and disorders described herein.

In one embodiment, such additional pharmaceutical agents include one or more of the following: anti-cancer agents, and anti-inflammatory agents.

The compound or composition provided herein, or pharmaceutically acceptable derivative thereof, may be administered simultaneously with, prior to, or after administration of one or more of the above agents. Pharmaceutical compositions containing a compound provided herein and one or more of the above agents are also provided.

In practicing the methods, effective amounts of the compounds or compositions containing therapeutically effective concentrations of the compounds, which are formulated for systemic delivery, including parenteral, oral, or intravenous delivery, or for local or topical application are administered to an individual exhibiting the symptoms of the disease or disorder to be treated. The amounts are effective to ameliorate or eliminate one or more symptoms of the diseases or disorders.

Also contemplated herein are combination therapies using one or more compounds or compositions provided herein, or pharmaceutically acceptable salts thereof, in combination with other pharmaceutically active agents for the treatment of the diseases and disorders described herein.

In one embodiment, such additional pharmaceutical agents include one or more of the following: anti-cancer agents and anti-inflammatory agents.

The compound or composition provided herein, or pharmaceutically acceptable salt, solvate, hydrate or prodrug thereof, may be administered simultaneously with, prior to, or after administration of one or more of the above agents. Pharmaceutical compositions containing a compound provided herein and one or more of the above agents are also provided.

In practicing the methods, effective amounts of the compounds or compositions containing therapeutically effective concentrations of the compounds, which are formulated for oral, systemic, including parenteral or intravenous delivery, or for local or topical application are administered to an individual exhibiting the symptoms of the disease or disorder to be treated. The amounts are effective to treat, manage or ameliorate the disease or ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

BRIEF DESCRIPTION OF THE DRAWING

FIG. 1 depicts results of tumor growth delay experiment in a MV4-11 human leukemia xenograft model. A compound provided herein was administered by oral gavage (p.o.) once daily for twenty-eight days (qd×28) to mice implanted with MV4-11 tumors. The compound at 3 mg/kg and 10 mg/kg inhibits growth of MV4-11 xenographs in a statistically significant manner (p<0.01) compared to vehicle controls in the absence of morbidity or mortality.

DETAILED DESCRIPTION

Provided herein are imidazolothiazole compounds of formula (I) that have activity as protein kinase modulators. Further provided are methods of treating, preventing or ameliorating diseases that are modulated by protein kinases and pharmaceutical compositions and dosage forms useful for such methods. The methods and compositions are described in detail in the sections below.

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

"Alkyl" refers to a straight or branched hydrocarbon chain radical consisting solely of carbon and hydrogen atoms, containing no unsaturation, having from one to ten carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkenyl" refers to a straight or branched hydrocarbon chain radical consisting solely of carbon and hydrogen atoms, containing at least one double bond, having from two to ten carbon atoms, and which is attached to the rest of the molecule by a single bond or a double bond, e.g., ethenyl, prop-1-enyl, but-1-enyl, pent-1-enyl, penta-1,4-dienyl, and the like.

"Alkynyl" refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g., ethynyl, prop-1-ynyl, but-1-ynyl, pent-1-ynyl, pent-3-ynyl and the like.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene and the like. The alkylene chain may be attached to the rest of the molecule through any two carbons within the chain.

"Alkenylene" or "alkenylene chain" refers to a straight or branched chain unsaturated divalent radical consisting solely of carbon and hydrogen atoms, having from one to eight carbon atoms, wherein the unsaturation is present only as double bonds and wherein the double bond can exist between any two carbon atoms in the chain, e.g., ethenylene, prop-1-enylene, but-2-enylene and the like. The alkenylene chain may be attached to the rest of the molecule through any two carbons within the chain.

"Alkoxy" refers to the radical having the formula —OR wherein R is alkyl or haloalkyl. An "optionally substituted alkoxy" refers to the radical having the formula —OR wherein R is an optionally substituted alkyl as defined herein.

"Alkynylene" or "alkynylene chain" refers to a straight or branched chain unsaturated divalent radical consisting solely of carbon and hydrogen atoms, having from one to eight carbon atoms, wherein the unsaturation is present only as triple bonds and wherein the triple bond can exist between any two carbon atoms in the chain, e.g., ethynylene, prop-1-ynylene, but-2-ynylene, pent-1-ynylene, pent-3-ynylene and the like. The alkynylene chain may be attached to the rest of the molecule through any two carbons within the chain.

"Amino" refers to a radical having the formula —NR'R" wherein R' and R" are each independently hydrogen, alkyl or haloalkyl. An "optionally substituted amino" refers to a radical having the formula —NR'R" wherein one or both of R' and R" are optionally substituted alkyl as defined herein.

"Anti-cancer agents" refers to anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent® and Bevacizumab) or any other cytotoxic agents, (estramustine phosphate, prednimustine), hormones or hormone agonists, antagonists, partial agonists or partial antagonists, kinase inhibitors, and radiation treatment.

"Anti-inflammatory agents" refers to matrix metalloproteinase inhibitors, inhibitors of pro-inflammatory cytokines (e.g., anti-TNF molecules, TNF soluble receptors, and IL1) non-steroidal anti-inflammatory drugs (NSAIDs) such as prostaglandin synthase inhibitors (e.g., choline magnesium salicylate, salicylsalicyclic acid), COX-1 or COX-2 inhibitors), or glucocorticoid receptor agonists such as corticosteroids, methylprednisone, prednisone, or cortisone.

"Aryl" refers to a radical of carbocylic ring system wherein at least one of the rings is aromatic. The aryl may be fully aromatic, examples of which are phenyl, naphthyl, anthracenyl, acenaphthylenyl, azulenyl, fluorenyl, indenyl and pyrenyl. The aryl may also contain an aromatic ring in combination with a non-aromatic ring, examples of which are acenaphene, indene, and fluorene.

"Aralkyl" refers to a radical of the formula —$R_aR_b$ where $R_a$ is an alkyl radical as defined above, substituted by $R_b$, an aryl radical, as defined above, e.g., benzyl. Both the alkyl and aryl radicals may be optionally substituted as defined herein.

"Aralkoxy" refers to a radical of the formula —$OR_aR_b$ where —$R_aR_b$ is an aralkyl radical as defined above. Both the alkyl and aryl radicals may be optionally substituted as defined herein.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl, norbornane, norbornene, adamantyl, bicyclo[2.2.2]octane and the like.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined herein.

"Halo", "halogen" or "halide" refers to F, Cl, Br or I.

"Haloalkyl" refers to an alkyl group in which one or more of the hydrogen atoms are replaced by halogen. Such groups include, but are not limited to, chloromethyl, trifluoromethyl and 1-chloro-2-fluoroethyl.

"Haloalkenyl" refers to an alkenyl group in which one or more of the hydrogen atoms are replaced by halogen. Such groups include, but are not limited to, 1-chloro-2-fluoroethenyl.

"Heterocyclyl" refers to a stable 3- to 15-membered ring radical which consists of carbon atoms and from one to five heteroatoms selected from the group consisting of nitrogen, oxygen and sulfur. In one embodiment, the heterocyclic ring system radical may be a monocyclic, bicyclic or tricyclic ring or tetracyclic ring system, which may include fused or bridged ring systems; and the nitrogen or sulfur atoms in the heterocyclic ring system radical may be optionally oxidized; the nitrogen atom may be optionally quaternized; and the heterocyclyl radical may be partially or fully saturated or aromatic. The heterocyclic ring system may be attached to the main structure at any heteroatom or carbon atom which results in the creation of a stable compound. Examples of such heterocyclic radicals include, but are not limited to: acridinyl, azepinyl, benzimidazolyl, benzindolyl, benzisoxazinyl, benzo[4,6]imidazo[1,2-a]pyridinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thiophenyl, triazinyl, triazolyl and 1,3,5-trithianyl.

"Heteroaralkyl" refers to a radical of the formula —$R_aR_f$— where $R_a$ is an alkyl radical as defined above and $R_f$ is a heteroaryl radical as defined herein. The alkyl radical and the heteroaryl radical may be optionally substituted as defined herein.

"Heteroaralkoxy" refers to a radical of the formula —$OR_aR_f$— where —$R_aR_f$— is a heteroaralkyl radical as defined above. The alkyl radical and the heteroaryl radical may be optionally substituted as defined herein.

"Heteroaryl" refers to a heterocyclyl radical as defined above which is aromatic. The heteroaryl radical may be attached to the main structure at any heteroatom or carbon atom which results in the creation of a stable compound. Examples of such heteroaryl radicals include, but are not limited to: acridinyl, benzimidazolyl, benzindolyl, benzisoxazinyl, benzo[4,6]imidazo[1,2-a]pyridinyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuranyl, furanyl, imidazolyl, imidazopyridinyl, imidazothiazolyl, indazolyl, indolizinyl, indolyl, isobenzothienyl, isoindolinyl, isoquinolinyl, isothiazolidinyl, isothiazolyl, naphthyridinyl, octahydroindolyl, octahydroisoindolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, pteridinyl, purinyl, pyrazinyl, pyrazolyl, pyridazinyl, pyridinyl, pyridopyridinyl, pyrimidinyl, pyrrolyl, quinazolinyl, quinolinyl, quinoxalinyl, tetrazolyl, thiadiazolyl, thiazolyl, thiophenyl, triazinyl and triazolyl.

"Heterocyclylalkyl" refers to a radical of the formula —$R_aR_e$— wherein $R_a$ is an alkyl radical as defined above and $R_e$ is a heterocyclyl radical as defined herein. The alkyl radical and the heterocyclyl radical may be optionally substituted as defined herein.

"Heterocyclylalkoxy" refers to a radical of the formula —$OR_aR_e$— wherein —$R_aR_e$— is a heterocyclylalkyl radical as defined above. The alkyl radical and the heterocyclyl radical may be optionally substituted as defined herein.

"$IC_{50}$" refers to an amount, concentration or dosage of a particular test compound that achieves a 50% inhibition of a maximal response, such as cell growth or proliferation measured via any the in vitro or cell based assay described herein.

"Optionally substituted alkyl", "optionally substituted alkenyl" and "optionally" refer to alkyl radicals, alkenyl radicals and alkynyl radicals, respectively, substituted alkynyl that may be optionally substituted by one or more substituents independently selected from the group consisting of nitro, halo, azido, cyano, cycloalkyl, heteroaryl, heterocyclyl, —$OR^x$, —$N(R^y)(R^z)$, —$SR^x$, —$C(J)R^x$, —$C(J)OR^x$, —$C(J)N(R^y)(R^z)$, —$C(J)SR^x$, —$S(O)_tR^w$ (where t is 1 or 2), —$OC(J)R^x$, —$OC(J)OR^x$, —$OC(J)N(R^y)(R^z)$, —$OC(J)SR^x$, —$N(R^x)C(J)R^x$, —$N(R^x)C(J)OR^x$, —$N(R^x)C(J)N(R^y)(R^z)$, —$N(R^x)C(J)SR^x$, —$Si(R^w)_3$, —$N(R^x)S(O)_2R^w$, —$N(R^x)S(O)_2N(R^y)(R^z)$, —$S(O)_2N(R^y)(R^z)$, —$P(O)(R^v)_2$, —$OP(O)(R^v)_2$, —$C(J)N(R^x)S(O)_2R^w$, —$C(J)N(R^x)N(R^x)S(O)_2R^w$, —$C(R^x)=N(OR^x)$, and —$C(R^x)=NN(R^y)(R^z)$, wherein:

$R^x$ is hydrogen, alkyl, alkenyl, alkynyl, cycloalkyl, cycloalkylalkyl, heterocyclyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclalkyl, aryl, aralkyl, heteroaryl, or heteroaralkyl; or $R^y$ and $R^z$, together with the nitrogen atom to which they are attached, form a heterocyclyl or heteroaryl;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

$R^v$ is alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$; and J is O, $NR^x$ or S.

Unless stated otherwise specifically described in the specification, it is understood that the substitution can occur on any carbon of the alkyl, alkenyl or alkynyl group.

"Optionally substituted aryl", "optionally substituted cycloalkyl", "optionally substituted heteroaryl" and "optionally substituted heterocyclyl" refers to aryl, cycloalkyl, heterocyclyl and heteroaryl radicals, respectively, that are optionally substituted by one or more substituents selected from the group consisting of nitro, halo, haloalkyl, haloalkenyl, azido, cyano, oxo, thioxo, imino, alkyl, alkenyl, alkynyl, cycloalkyl, cycloalkylalkyl, heterocyclyl, heterocycylalkyl, heteroaryl, heteroaralkyl, —$R''OR^x$, —$R''N(R^y)(R^z)$, —$R''SR^x$, —$R''C(J)R^x$, —$R''C(J)OR^x$, —$R''C(J)N(R^y)(R^z)$, —$R''C(J)SR^x$, —$R''S(O)_tR^w$ (where t is 1 or 2), —$R''OC(J)R^x$, —$R''OC(J)OR^x$, —$R''OC(J)N(R^y)(R^z)$, —$R''OC(J)SR^x$, —$R''N(R^x)C(J)R^x$, —$R''N(R^x)C(J)OR^x$, —$R''N(R^x)C(J)N(R^y)(R^z)$, —$R''N(R^x)C(J)SR^x$, —$R''Si(R^w)_3$, —$R''N(R^x)S(O)_2R^w$, —$R''N(R^x)S(O)_2N(R^y)(R^z)$, —$R''S(O)_2N(R^y)(R^z)$, —$R''P(O)(R^v)_2$, —$R''OP(O)(R^v)_2$, —$R''C(J)N(R^x)S(O)_2R^w$, —$R''C(J)N(R^x)N(R^x)S(O)_2R^w$, —$R''C(R^x)=N(OR^x)$ and —$R''C(R^x)=NN(R^y)(R^z)$, wherein:

each $R''$ is independently alkylene or a direct bond;

each $R^v$ is independently alkyl, alkenyl, alkynyl, cycloalkyl, cycloalkylalkyl, heterocyclyl, heterocyclylalkyl, aryl, aralkyl, heteroaryl, heteroaralkyl, hydroxy, —$OR^x$ or —$N(R^y)(R^z)$;

$R^w$ is alkyl, alkenyl, alkynyl, cycloalkyl, cycloalkylalkyl, heterocyclyl, heterocyclylalkyl, aryl, aralkyl, heteroaryl, or heteroaralkyl;

each $R^x$ is independently hydrogen, alkyl, alkenyl, alkynyl, cycloalkyl, cycloalkylalkyl, heterocycyl, heterocyclylalkyl, aryl, aralkyl, heteroaryl, or heteroaralkyl;

$R^y$ and $R^z$ are each independently hydrogen, alkyl, alkenyl, alkynyl, cycloalkyl, cycloalkylalkyl, heterocyclyl, heterocyclylalkyl; aryl, aralkyl, heteroaryl, or heteroaralkyl;

$R^y$ and $R^z$, together with the nitrogen atom to which they are attached, form a heterocycle or heteroaryl; and J is O, $NR^x$ or S.

Unless stated otherwise specifically described in the specification, it is understood that the substitution can occur on any atom of the cycloalkyl, heterocyclyl, aryl or heteroaryl group.

"Oxo" refers to =O.

"Pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (2005) *Medicinal Chemistry A Biochemical Approach*, Oxford University Press, New York).

"Sulfide" refers to the radical having the formula —SR wherein R is an alkyl or haloalkyl group. An "optionally substituted sulfide" refers to the radical having the formula —SR wherein R is an optionally substituted alkyl as defined herein.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

Unless specifically stated otherwise, where a compound may assume alternative tautomeric, regioisomeric and/or stereoisomeric forms, all alternative isomers are intended to be encompassed within the scope of the claimed subject matter. For example, where a compound is described as having one of two tautomeric forms, it is intended that the both tautomers be encompassed herein.

Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is to be understood that the compounds provided herein may contain chiral centers. Such chiral centers may be of either the (R) or (S) configuration, or may be a mixture thereof.

Optically active (+) and (−), (R)- and (S)-, or (D)- and (L)-isomers may be prepared using chiral synthons or chiral reagents, or resolved using conventional techniques, such as reverse phase HPLC.

As used herein, the term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer.

Where the number of any given substituent is not specified (e.g., haloalkyl), there may be one or more substituents present. For example, "haloalkyl" may include one or more of the same or different halogens.

In the description herein, if there is any discrepancy between a chemical name and chemical structure, the structure preferably controls.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942-944).

B. Compounds

In one embodiment, the compounds provided are of formula (I):

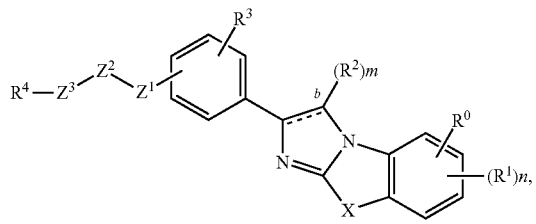

wherein, bond b is a single bond or double bond;

X is —S—, —N(R$^5$)— or —O—;

Z$^1$ and Z$^3$ are each independently —N(R$^5$)—, —(CH$_2$)$_q$, —O—, —S—, or a direct bond;

Z$^2$ is —C(O)— or —C(S)—;

m is an integer from 1 to 2;

n is an integer from 1 to 3;

each q is independently an integer from 1 to 4;

R$^0$ is hydrogen, halo, hydroxy, optionally substituted alkyl, or optionally substituted alkoxy;

each R$^1$ is independently selected from the group consisting of halo, optionally substituted alkyl, optionally substituted alkenyl, optionally substituted alkynyl, optionally substituted heterocyclylalkyl, optionally substituted heterocyclylalkenyl, optionally substituted heteroaralkyl, optionally substituted heteroaralkenyl, —R$^6$OR$^7$, —R$^6$SR$^7$, —R$^6$S(O)$_t$R$^8$ (where t is 1 or 2), —R$^6$N(R$^7$)$_2$, —R$^6$CN, —R$^6$C(O)R$^7$, —R$^6$C(S)R$^7$, —R$^6$C(NR$^7$)R$^7$, —R$^6$C(O)OR$^7$, —R$^6$C(S)OR$^7$, —R$^6$C(NR$^7$)OR$^7$, —R$^6$C(O)N(R$^7$)$_2$, —R$^6$C(S)N(R$^7$)$_2$, —R$^6$C(NR$^7$)N(R$^7$)$_2$, —R$^6$C(O)N(R$^7$)R$^9$N(R$^7$)$_2$, —R$^6$C(O)SR$^8$, —R$^6$C(S)SR$^8$, —R$^6$C(NR$^7$)SR$^8$, —R$^6$S(O)$_t$OR$^7$ (where t is 1 or 2), —R$^6$S(O)$_t$N(R$^7$)$_2$ (where t is 1 or 2), —R$^6$S(O)$_t$N(R$^7$)N(R$^7$)$_2$ (where t is 1 or 2), —R$^6$S(O)$_t$N(R$^7$)N=C(R$^7$)$_2$, —R$^6$S(O)$_t$N(R$^7$)C(O)R$^8$ (where t is 1 or 2), —R$^6$S(O)$_t$N(R$^7$)C(O)N(R$^7$)$_2$ (where t is 1 or 2), —R$^6$S(O)$_t$N(R$^7$)C(NR$^7$)N(R$^7$)$_2$ (where t is 1 or 2), —R$^6$N(R$^7$)C(O)R$^8$, —R$^6$N(R$^7$)C(O)OR$^8$, —R$^6$N(R$^7$)C(O)SR$^8$, —R$^6$N(R$^7$)C(S)SR$^8$, —R$^6$N(R$^7$)C(O)N(R$^7$)$_2$, —R$^6$N(R$^7$)C(NR$^7$)N(R$^7$)$_2$, —R$^6$N(R$^7$)C(S)N(R$^7$)$_2$, —R$^6$N(R$^7$)S(O)$_t$R$^8$ (where t is 1 or 2), —R$^6$OC(O)R$^8$, —R$^6$OC(NR$^7$)R$^8$, —R$^6$OC(S)R$^8$, —R$^6$OC(O)OR$^8$, —R$^6$OC(NR$^7$)OR$^8$, —R$^6$OC(S)OR$^8$, —R$^6$OC(O)SR$^8$, —R$^6$OC(O)N(R$^7$)$_2$, —R$^6$OC(NR$^7$)N(R$^7$)$_2$, —R$^6$OC(S)N(R$^7$)$_2$, —R$^6$OR$^9$N(R$^7$)$_2$, —R$^6$SR$^9$N(R$^7$)$_2$, —R$^6$N(R$^7$)R$^9$N(R$^7$)$_2$, —R$^6$C(O)R$^9$C(O)R$^7$, —R$^6$C(O)R$^9$C(S)R$^7$, —R$^6$C(O)R$^9$C(NR$^7$)R$^7$, —R$^6$C(O)R$^9$C(O)OR$^7$, —R$^6$C(O)R$^9$C(S)OR$^7$, —R$^6$C(O)R$^9$C(NR$^7$)OR$^7$, —R$^6$C(O)R$^9$C(O)N(R$^7$)$_2$, —R$^6$C(O)R$^9$C(S)N(R$^7$)$_2$, —R$^6$C(O)R$^9$C(NR$^7$)N(R$^7$)$_2$, —R$^6$C(O)R$^9$C(O)SR$^8$, —R$^6$C(O)R$^9$C(S)SR$^8$ and —R$^6$C(O)R$^9$C(NR$^7$)SR$^8$;

each R$^2$ is independently selected from hydrogen, halo, nitro, cyano, optionally substituted alkyl, —OR$^{12}$, —SR$^{12}$, —N(R$^{12}$)$_2$, —S(O)$_t$R$^{13}$ (where t is 1 or 2), —C(O)R$^{12}$, —C(O)OR$^{12}$, —C(O)N(R$^{12}$)$_2$, —C(C)SR$^{12}$, or —N(R$^{12}$)S(O)$_t$R$^{13}$ (where t is 1 or 2);

R$^3$ is hydrogen, halo, nitro, cyano, optionally substituted alkyl, —OR$^{12}$, —SR$^{12}$, —N(R$^{12}$)$_2$, —S(O)$_t$R$^{13}$ (where t is 1 or 2), —C(O)R$^{12}$, —C(O)OR$^{12}$, —C(O)N(R$^{12}$)$_2$, —C(O)SR$^{12}$, or —N(R$^{12}$)S(O)$_t$R$^{13}$ (where t is 1 or 2);

R$^4$ is selected from the group consisting of optionally substituted alkyl, optionally substituted heterocyclyl, optionally substituted heteroaryl, optionally substituted cycloalkyl, optionally substituted cycloalkenyl, and optionally substituted aryl;

each R$^5$ is independently hydrogen, or optionally substituted alkyl;

each R$^6$ is independently a direct bond, an optionally substituted straight or branched alkylene chain, or an optionally substituted straight or branched alkenylene chain;

each R$^7$ is independently selected from (i) or (ii) below (i) R$^7$ is selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl, or (ii) two (R$^7$)s together with the atom to which they are attached form an optionally substituted heterocyclyl or optionally substituted heteroaryl;

R$^8$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclalkyl, optionally substituted heteroaryl and optionally substituted heteroaralkyl;

each R$^9$ is independently an optionally substituted straight or branched alkylene chain or an optionally substituted straight or branched alkenylene chain;

each R$^{12}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and R$^{13}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl;

with the proviso that, (i) if —Z$^1$Z$^2$Z$^3$R$^4$ is —NHC(O)Bu then R$^1$ may not be ethoxy;

(ii) if —Z$^1$Z$^2$Z$^3$R$^4$ is —C(O)OR$_p$, where R$_p$=H, methyl, or ethyl, then R$^1$ may not be hydroxyl, methoxy or methoxycarbonyl;

(iii) if Z$^1$Z$^2$Z$^3$R$^4$ is —NHC(O)C(O)OR$_p$, where R$_p$=H, methyl, or ethyl, then R$^1$ may not be methoxy;

(iv) if —Z$^1$Z$^2$Z$^3$R$^4$ is —CH$_2$C(O)OR$_p$, where R$_p$=H, methyl, or ethyl, then R$^1$ may not be methoxy or ethoxy;

(v) if —Z$^1$Z$^2$Z$^3$R$^4$ is —OC(O)CH$_3$, then R$^1$ may not be methyl, methoxy or ethoxy.

In one embodiment, the compound is a single isomer, a mixture of isomers, a racemic mixture of isomers, a solvate, a hydrate or a prodrug; or a pharmaceutically acceptable salt thereof.

In one embodiment, the compound provided herein is a pharmaceutically acceptable salt of the compound of formula (I). In one embodiment, the compounds provided herein is a solvate of the compound of formula (I). In one embodiment, the compounds provided herein is a hydrate of compound of formula (I). In one embodiment, the compound provided herein is a prodrug of the compound of formula (I).

In one embodiment, the —Z$^1$Z$^2$Z$^3$R$^4$ group is attached at a para position on the phenyl ring. In one embodiment, the —Z$^1$Z$^2$Z$^3$R$^4$ group is attached at a meta position on the phenyl ring.

In one embodiment, R$^4$ is optionally substituted heterocyclyl or optionally substituted heteroaryl and other variables are as described elsewhere herein. The substituents on R$^4$, when present, are selected from one or more, in one embodiment, one, two, three or four groups selected from halo, optionally substituted alkyl, optionally substituted cycloalkyl, optionally substituted aryl, optionally substituted heterocyclyl, and optionally substituted heteroaryl. In one embodiment, R$^4$ is 3-12 membered optionally substituted heterocyclyl, wherein the hetero atoms are selected from one or more nitrogen, sulfur or oxygen. In one embodiment, R$^4$ is 5-10 membered optionally substituted heterocyclyl. In one embodiment, R$^4$ is 5-12 membered optionally substituted heteroaryl, wherein the hetero atoms are selected from one or more nitrogen, sulfur or oxygen. In one embodiment, R$^4$ is 5-6 membered optionally substituted heteroaryl.

In another embodiment, R$^4$ is selected from the group consisting of:

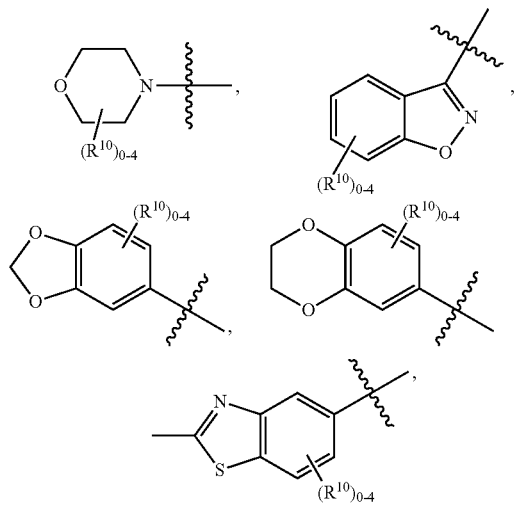

wherein, each R$^{10}$ is independently selected from hydrogen, halo, optionally substituted alkyl, optionally substituted cycloalkyl, optionally substituted aryl, optionally substituted heterocyclyl, and optionally substituted heteroaryl.

In another embodiment, R$^4$ is selected from the group consisting of:

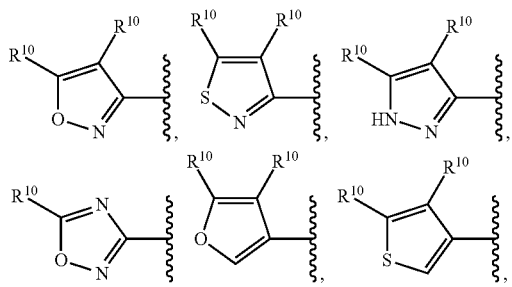

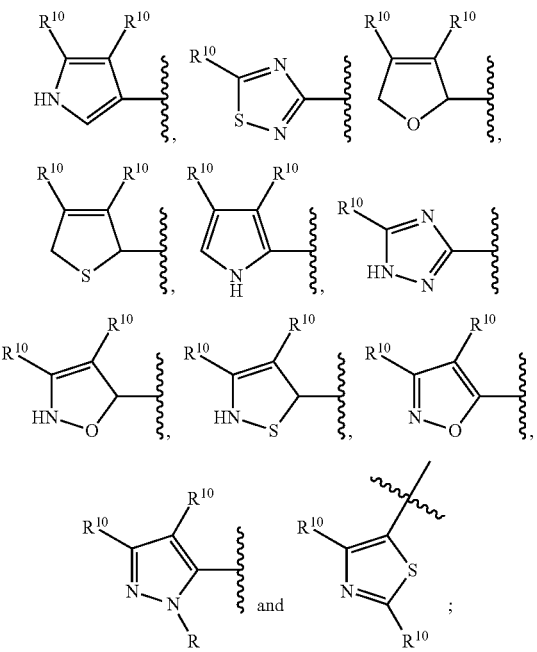

and each R$^{10}$ is independently selected from hydrogen, halo, optionally substituted alkyl, optionally substituted cycloalkyl, optionally substituted aryl, optionally substituted heterocyclyl, and optionally substituted heteroaryl.

In another embodiment, the compounds provided herein have formula (I), wherein R$^4$ is selected from the group consisting of:

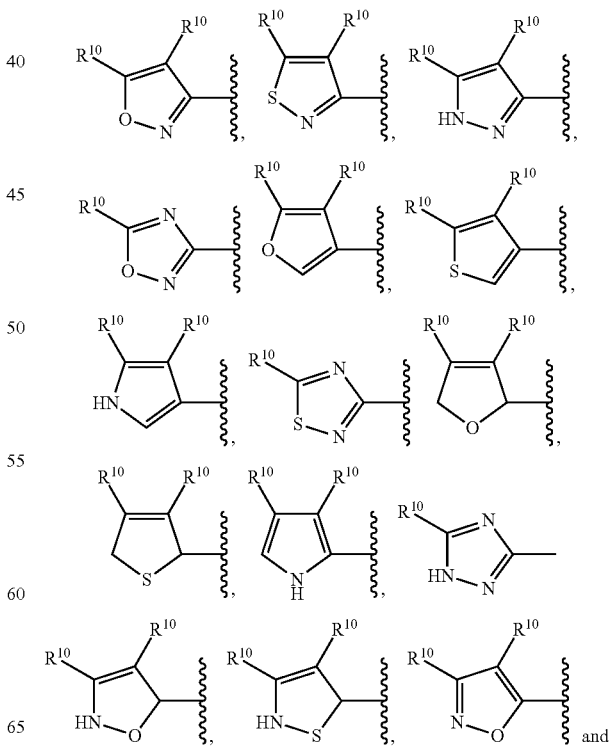

and each $R^{10}$ is independently selected from hydrogen, halo, optionally substituted alkyl, optionally substituted cycloalkyl, optionally substituted aryl, optionally substituted heterocyclyl, and optionally substituted heteroaryl. In one embodiment, $R^{10}$ is hydrogen, alkyl, haloalkyl or haloaryl. In one embodiment, $R^{10}$ is hydrogen, methyl, tert-butyl, trifluoromethyl or p-chlorophenyl. In one embodiment, $R^{10}$ is tert-butyl.

In one embodiment, $R^4$ is where $R^{10}$ is as described elsewhere herein. In one embodiment, $R^{10}$ is alkyl. In one embodiment, $R^{10}$ is hydrogen. In one embodiment, one $R^{10}$ is alkyl and the other $R^{10}$ is hydrogen.

In one embodiment, $R^4$ is

In another embodiment, $R^1$ is —$R^6OR^9N(R^7)_2$, wherein $R^6$ is a direct bond, an optionally substituted straight or branched alkylene chain or an optionally substituted straight or branched alkenylene chain;

two ($R^7$)s together with the nitrogen atom to which they are attached form an optionally substituted heterocyclyl or optionally substituted heteroaryl; and $R^9$ is an optionally substituted straight or branched alkylene chain or an optionally substituted straight or branched alkenylene chain.

In another embodiment, $R^1$ is where K is —C(O)—, —$(CH_2)_q$—, —$(CH_2)_q$—, —$(CH_2)_qO$—, —$(CH_2)_q$—, —$(CH_2)_qC(O)$—, —C(O)NH$(CH_2)_q$—, —C(O)NH$(CH_2)_q$NH$(CH_2)_q$—, —$(CH_2)_qC(O)$NH$(CH_2)_q$—, —O$(CH_2)_q$—, —OC(O)—, —OC(O)$(CH_2)_q$— or a direct bond;

Y is —O—, —S—, —S(O)—, —S(O)$_2$—, —N($R^{14}$)—, —C(H)$R^{15}$—, or —C(O)—;

p is an integer from 0 to 2;

each q is independently an integer from 1 to 4;

$R^{14}$ is hydrogen, optionally substituted alkyl, optionally substituted cycloalkyl, optionally substituted heteroaryl, optionally substituted aryl, S(O)$_tR^{13}$ (where t is 1 or 2), —C(O)$R^{12}$, —C(O)O$R^{12}$, —C(O)N($R^{12}$)$_2$, or —C(O)S$R^{12}$;

$R^{15}$ is hydrogen, halo, nitro, cyano, optionally substituted alkyl, optionally substituted cycloalkyl, optionally substituted heteroaryl, optionally substituted aryl, —O$R^{12}$, —S$R^{12}$, —N($R^{12}$)$_2$, —S(O)$_tR^{13}$ (where t is 1 or 2), —C(O)$R^{12}$, —C(O)O$R^{12}$, —C(O)N($R^{12}$)$_2$, —C(O)S$R^{12}$, or —N($R^{12}$)S(O)$_tR^{13}$ (where t is 1 or 2);

each $R^{12}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl; and each $R^{13}$ is independently selected from the group consisting of optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl.

In another embodiment, $R^1$ is halo, alkyl, —$R^6OR^7$, —$R^6N(R^7)_2$, —$R^6C(O)OR^7$, —$R^6OR^9OR^7$, —$R^6OR^9N(R^7)_2$, —$R^6C(O)N(R^7)R^9N(R^7)_2$, —$R^6C(O)R^9N(R^7)R^9OR^7$ or —$R^6C(O)N(R^7)R^9OR^7$ and $R^7$ is hydrogen, optionally substituted alkyl, optionally substituted alkenyl, optionally substituted alkynyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroaralkyl.

In one embodiment, $R^1$ is fluoro, bromo, methyl, ethyl, hydroxy, methoxy, diethylamino or carboxy.

In one embodiment, q is 1-3. In one embodiment, q is 1, 2, 3 or 4. In one embodiment, K is a direct bond.

In one embodiment, X is —S—. In another embodiment, X is —N($R^5$)—, where $R^5$ is hydrogen or lower alkyl. In another embodiment, X is —O—.

In one embodiment, —$Z^1Z^2Z^3$— is —NHC(O)NH—, —NHC(O)N(CH$_3$)—, —N(CH$_3$)C(O)NH—, —C(O)NH—, —NHC(O)—, —NCH$_2$C(O)NH—. In one embodiment, —$Z^1Z^2Z^3$— is —NHC(O)NH—.

In another aspect, provided herein is a compound of formula (Ia):

wherein the variables are as defined elsewhere herein.

In another aspect, provided herein is a compound of formula (Ia):

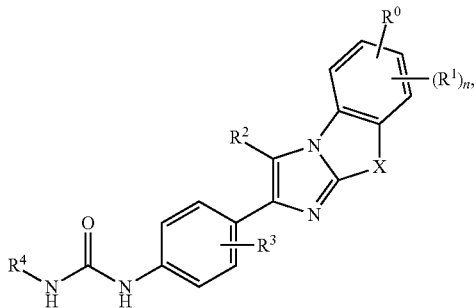

wherein the variables are as defined elsewhere herein.

In another aspect, provided herein is a compound of formula (II):

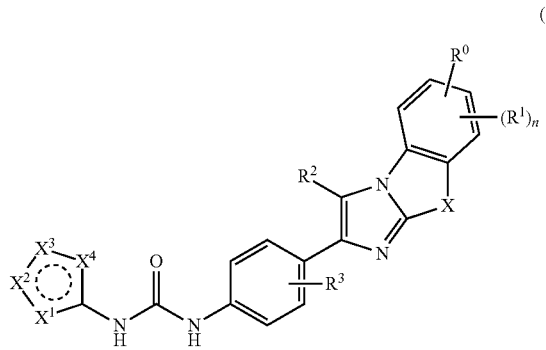

wherein
X is —S—, —N($R^5$)— or —O—;
$X^1$, $X^2$, $X^3$, $X^4$ are each independently selected from —C($R^{10}$)—, —C($R^{10}$)$_2$—, —N—, —N($R^{16}$)—, —O—, and —S—, provided that no more than two of $X^1$, $X^2$, $X^3$ and $X^4$ are heteroatoms and wherein no two adjacent X's are both —O— or —S—;

and each $R^{10}$ is independently selected from hydrogen, halo, optionally substituted alkyl, optionally substituted cycloalkyl, optionally substituted aryl, optionally substituted heterocyclyl, and optionally substituted heteroaryl;

each $R^{16}$ is independently selected from hydrogen, optionally substituted alkyl, optionally substituted cycloalkyl, optionally substituted aryl, optionally substituted heterocyclyl, and optionally substituted heteroaryl; and n, $R^0$, $R^1$, $R^2$, $R^3$, are defined as described above for formula (I);

as a single isomer, a mixture of isomers, a racemic mixture of isomers; a solvate, a hydrate or a prodrug; or as a pharmaceutically acceptable salt thereof.

In one embodiment, the compounds provided herein have formula (II), wherein n is 0-3. In one embodiment, the compounds provided herein have formula (II), wherein n is 0-3.

In another embodiment, the compound provided herein has formula (II) wherein $R^2$ and $R^3$ are independently selected from hydrogen, halo or optionally substituted lower alkyl.

In another aspect, provided herein is a compound of formula (III):

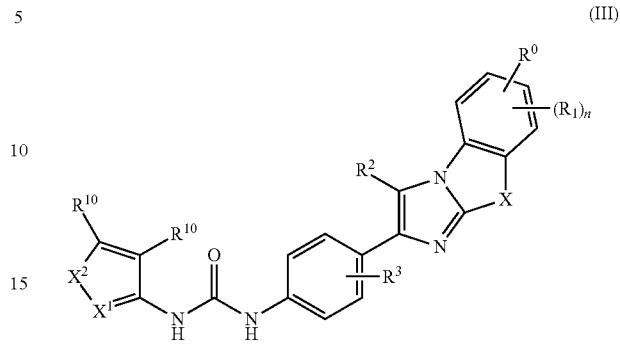

wherein:
X is —S—, —N($R^5$)— or —O—;
$X^1$ is —C($R^{10}$)—, or —N—;
$X^2$ is —O— or —S—;
where each $R^{10}$ is independently selected from hydrogen, halo, optionally substituted alkyl, optionally substituted cycloalkyl, optionally substituted aryl, optionally substituted heterocyclyl, and optionally substituted heteroaryl;
and the remainder of n, $R^0$, $R^1$, $R^2$, $R^3$, $R^5$ and X are as defined above for formula (I);
as a single isomer, a mixture of isomers, a racemic mixture of isomers, a solvate, a hydrate or a prodrug, or as a pharmaceutically acceptable salt thereof.

In another aspect, provided herein is compound of formula (IIIa):

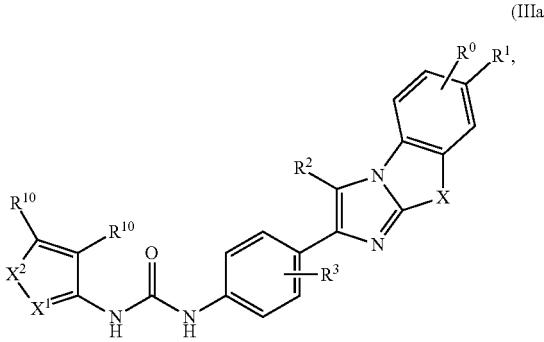

wherein the variables are as described elsewhere herein.

In another embodiment, compounds provided herein have formula (III) wherein $X^1$ is —N— and $X^2$ is —O—.

In another embodiment, compounds provided herein have formula (III) wherein $R^2$ and $R^3$ are independently selected from hydrogen, halo or optionally substituted lower alkyl.

In another aspect, the compound is of formula (III) wherein:
each $R^2$ is independently selected from hydrogen, halo, nitro, cyano, optionally substituted alkyl, —O$R^{12}$, —S$R^{12}$, —N($R^{12}$)$_2$, —S(O)$_t R^{13}$ (where t is 1 or 2), —C(O)$R^{12}$, —C(O)O$R^{12}$, —C(O)N($R^{12}$)$_2$, —C(O)S$R^{12}$, or —N($R^{12}$)S(O)$_t R^{13}$ (where t is 1 or 2);
each $R^3$ is independently selected from hydrogen, halo, nitro, cyano, optionally substituted alkyl;

In one embodiment, the compounds provided herein have formula (II), wherein n is 0-3. In one embodiment, the compounds provided herein have formula (II), wherein n is 0.

In another aspect, provided herein is a compound of formula (IV):

(IV)

wherein:

K is —(CH$_2$)$_q$—, —(CH$_2$)$_q$O—, —(CH$_2$)$_q$O(CH$_2$)$_q$—, —(CH$_2$)$_q$C(O)—, —(CH$_2$)$_q$C(O)NH(CH$_2$)$_q$—, —O(CH$_2$)$_q$—, —OC(O)—, —OC(O)(CH$_2$)$_q$— or a direct bond;

X is —S—, —N(R$^5$)— or —O—;

X$^1$ is —C(R$^{10}$)—, or —N—;

X$^2$ is —O— or —S—;

Y is —O—, —S—, —S(O)—, —S(O)$_2$—, —N(R$^{14}$)—, —C(H)R—, or —C(O)—;

p is an integer from 0 to 2;

each q is independently an integer from 1 to 4;

R$^{10}$ is independently selected from hydrogen, halo, optionally substituted alkyl, optionally substituted cycloalkyl, or optionally substituted aryl;

R$^{14}$ is independently, hydrogen, optionally substituted alkyl, optionally substituted cycloalkyl, optionally substituted heteroaryl, optionally substituted aryl, S(O)$_t$R$^{13}$ (where t is 1 or 2), —C(O)R$^{12}$, —C(O)OR$^{12}$, —C(O)N(R$^{12}$)$_2$, or —C(O)SR$^{12}$;

R$^{15}$ is independently, hydrogen, halo, nitro, cyano, optionally substituted alkyl, optionally substituted cycloalkyl, optionally substituted heteroaryl, optionally substituted aryl, —OR$^{12}$, —SR$^{12}$, —N(R$^{12}$)$_2$, S(O)$_t$R$^{13}$ (where t is 1 or 2), —C(O)R$^{12}$, —C(O)OR$^{12}$, —C(O)N(R$^{12}$)$_2$, —C(O)SR$^{12}$, or —N(R$^{12}$)S(O)$_t$R$^{13}$ (where t is 1 or 2);

and the remainder of R$^0$, R$^2$, R$^3$, R$^5$, R$^{12}$, R$^{13}$ and X are as defined above for formula (I);

as a single isomer, a mixture of isomers, or as a racemic mixture of isomers, or as a solvate, or as a prodrug, or as a pharmaceutically acceptable salt thereof.

In one embodiment, R$^{14}$ is alkyl or —S(O)$_t$R$^{13}$ where t is 1 or 2 and R$^{13}$ is alkyl. In one embodiment, R$^{14}$ is methyl, ethyl or —S(O)$_t$R$^{13}$ where t is 2 and R$^{13}$ is methyl.

In another embodiment, compounds provided herein have formula (IV) wherein X$^1$ is —N— and X$^2$ is —O—.

In another embodiment, compounds provided herein have formula (IV) wherein R$^2$ and R$^3$ are independently selected from hydrogen, halo or optionally substituted lower alkyl.

In another embodiment, compounds provided herein have formula (IV) wherein R$^2$ and R$^3$ are both hydrogen.

In another aspect, provided herein is a compound of formula (IVa):

or a single isomer, a mixture of isomers, a racemic mixture of isomers, a solvate, a prodrug, or as a pharmaceutically acceptable salt thereof, and the variables are as defined elsewhere herein.

In another aspect, provided herein is a compound of formula (IVb):

or a single isomer, a mixture of isomers, a racemic mixture of isomers, a solvate, a prodrug, or as a pharmaceutically acceptable salt thereof, where the variables are as defined elsewhere herein.

In another aspect, the compound provided herein is of formula (V):

(V)

wherein K is —O(CH$_2$)$_q$—, —(CH$_2$)$_q$O—, —(CH$_2$)$_q$O(CH$_2$)$_q$— or —(CH$_2$)$_q$—;

p is an integer from 0 to 2;

each q is independently an integer from 1 to 4;

X$^1$ is —C(R$^{10}$)—, or —N—;

X$^2$ is —O— or —S—;

Y is —O—, —S—, —S(O)—, —S(O)$_2$—, —N(R$^{14}$)—, —C(H)R$^{15}$—, or —C(O)—, and m is 0, 1, or 2;

R$^{10}$ is independently selected from hydrogen, halo, optionally substituted alkyl, optionally substituted cycloalkyl, or optionally substituted aryl;

R$^{14}$ is independently, hydrogen, optionally substituted alkyl, optionally substituted cycloalkyl, optionally substituted heteroaryl, optionally substituted aryl, S(O)$_t$R$^{13}$, —C(O)R$^{12}$, —C(O)OR$^{12}$, —C(O)N(R$^{12}$)$_2$, or —C(O)SR$^{12}$;

$R^{15}$ is independently, hydrogen, halo, nitro, cyano, optionally substituted alkyl, optionally substituted cycloalkyl, optionally substituted heteroaryl, optionally substituted aryl, —$OR^{12}$, —$SR^{12}$, —$N(R^{12})_2$, —$S(O)_tR^{13}$ (where t is 1 or 2), —$C(O)R^{12}$, —$C(O)OR^{12}$, $C(O)N(R^{12})_2$, —$C(O)SR^{12}$, or —$N(R^{12})S(O)_tR^{13}$ (where t is 1 or 2);

and the remainder of, $R^2$, $R^3$, $R^{12}$, $R^{13}$ and X are as defined above for formula (I); as a single isomer, a mixture of isomers, a racemic mixture of isomers, a solvate, a hydrate or a prodrug, or as a pharmaceutically acceptable salt thereof.

In another embodiment, the compounds provided herein have formula (VI):

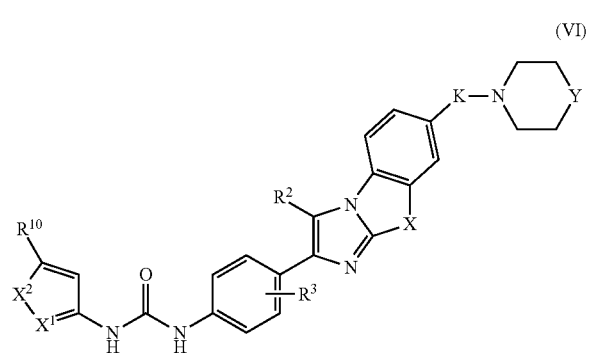

(VI)

wherein K is $O(CH_2)_q$—, —$(CH_2)_qO$—, or —$(CH_2)_qO(CH_2)_q$—;

each q is independently 1 to 4;

Y is —O—, —S—, or —$N(R^{14})$—;

$R^{10}$ is optionally substituted lower alkyl;

$R^{14}$ is hydrogen, optionally substituted lower alkyl, or —$S(O)_tR^{13}$;

$R^{13}$ is lower alkyl; and t is 1 or 2.

In another embodiment, the compounds provided herein have formula (VI):

wherein K is —$(CH_2)_q$—;

each q is independently 1 to 4;

Y is —O—, —S—, or —$N(R^{14})$—; and $R^{14}$ is hydrogen, optionally substituted lower alkyl, or —$S(O)_tR^{13}$ (where t is 1 or 2).

In another embodiment, the compounds provided herein have formula (VIa):

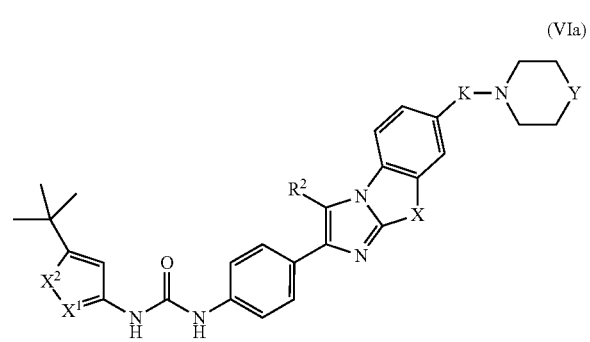

(VIa)

or a single isomer, a mixture of isomers, a racemic mixture of isomers, a solvate, a prodrug, or as a pharmaceutically acceptable salt thereof, where the variables are as defined elsewhere herein.

In another aspect, provided herein is a compound of formula (VII):

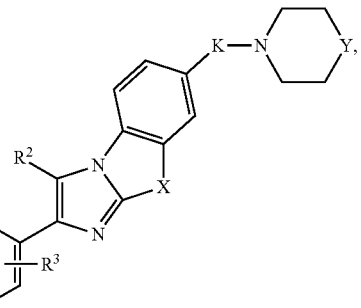

or a single isomer, a mixture of isomers, a racemic mixture of isomers, a solvate, a prodrug, or as a pharmaceutically acceptable salt thereof, where the variables are as defined elsewhere herein.

In one embodiment, —$Z^1Z^2Z^3$—$R^4$ is —NHC(O)NH—$R^4$ or —C(O)NHR$^4$.

In another aspect, provided herein is a compound of formula (VIIa):

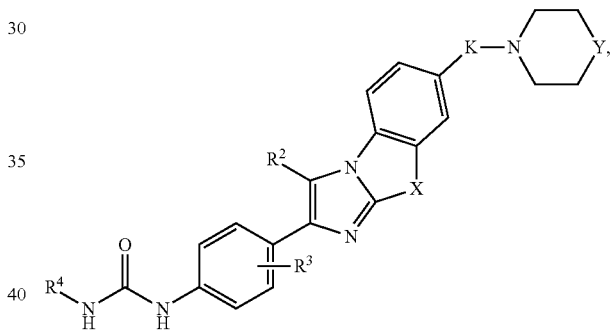

or a single isomer, a mixture of isomers, a racemic mixture of isomers, a solvate, a prodrug, or as a pharmaceutically acceptable salt thereof, where the variables are as defined elsewhere herein.

Also of interest are any pharmaceutically acceptable derivatives of the compounds disclosed herein, including without limitation salts, esters, enol ethers, enol esters, solvates, hydrates, and prodrugs of the compounds described herein.

Certain exemplary compounds are provided in Tables A, B and C below:

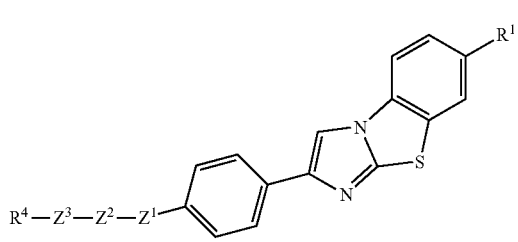

TABLE A

| Compound No. | R⁴ | —Z³—Z²—Z¹— | R¹ |
| --- | --- | --- | --- |
| D2 | 5-tert-butyl-isoxazol-3-yl | —NHC(O)N(CH₃)— | —CH₂CH₂CH₂N(morpholine) |
| E1 | morpholin-4-yl | —C(O)NH— | —CH₂CH₂C(O)N(morpholine) |
| E2 | benzo[d]isoxazol-3-yl | —CH₂C(O)NH— | —OCH₂CH₂N(morpholine) |
| E3 | 2-methyl-4-trifluoromethyl-thiazol-5-yl | —C(O)NH— | —OCH₂CH₂N(morpholine) |
| E4 | 2-(4-chlorophenyl)-4-methyl-thiazol-5-yl | —C(O)NH— | —OCH₂CH₂N(morpholine) |
| F1 | 2,3-dihydro-benzo[1,4]dioxin-6-yl | —NHC(O)NH— | —OCH₂CH₂N(morpholine) |
| F2 | 4-tert-butyl-phenyl | —NHC(O)NH— | —OCH₂CH₂N(morpholine) |
| F3 | benzo[1,3]dioxol-5-yl | —NHC(O)NH— | —OCH₂CH₂N(morpholine) |
| F8 | 2-methyl-benzothiazol-5-yl | —NHC(O)NH— | —OCH₂CH₂N(morpholine) |

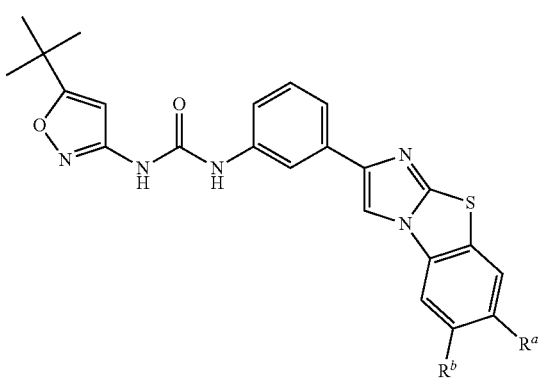
TABLE B
| Compound No. | R<sup>a</sup> | R<sup>b</sup> |
|---|---|---|
| B13 | —OCH₂CH₂N(morpholine) | H |
| B14 | —C(O)OCH₂CH₃ | H |
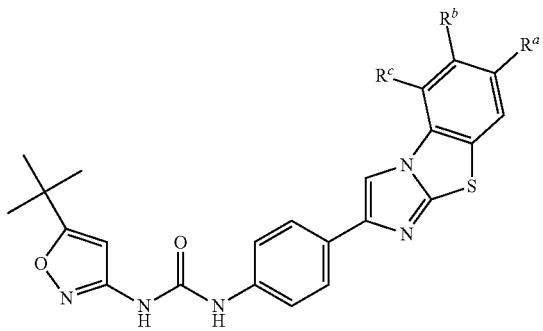
TABLE C
| Compound | R$^a$ | R$^b$ (at 6 position) | R$^c$ (at 5 position) |
|---|---|---|---|
| A1 | H | H | H |
| A2 | F | H | H |
| A3 | Me | H | H |
| A4 | —OH | H | H |
| A5 | —OCH3 | H | H |
| A6 | morpholin-4-yl | H | H |
| A7 | 4-methylpiperazin-1-yl | H | H |
| B1 | —OCH₂CH₂N(morpholine) | H | H |
| B2 | —OCH₂CH₂N(CH₂CH₃)₂ | H | H |
| B3 | —OCH₂CH₂N(piperidine) | H | H |
| B4 | —OCH₂CH₂N(N-methylpiperazine) | H | H |
| B5 | valine ester (—O-C(O)-CH(NH₂)-CH(CH₃)₂) | H | H |

TABLE C-continued

| Compound | R$^a$ | R$^b$ (at 6 position) | R$^c$ (at 5 position) |
|---|---|---|---|
| B6 | pyrrolidine-2-carboxylate ester (HN-pyrrolidinyl-C(O)O-) | H | H |
| B7 | —OCH$_2$CH$_2$CH$_2$N(morpholine) | H | H |
| B8 | —OCH$_2$CH$_2$CH$_2$N(thiomorpholine) | H | H |
| B9 | —OCH$_2$CH$_2$CH$_2$N(piperazine)N— | H | H |
| B10 | —OCH$_2$CH$_2$CH$_2$N(piperazine)NSO$_2$CH$_3$ | H | H |
| B11 | H | H | —OCH$_2$CH$_2$N(morpholine) |
| B12 | H | —OCH$_2$CH$_2$N(morpholine) | H |
| C1 | —CH$_2$C(O)OCH$_2$CH$_3$ | H | H |
| C2 | —CH$_2$C(O)OH | H | H |
| C3 | —CH$_2$CH$_2$C(O)OCH$_2$CH$_3$ | H | H |
| C4 | —CH$_2$CH$_2$C(O)OH | H | H |
| C5 | —CH$_2$CH$_2$C(O)N(piperazine)NCH$_2$CH$_3$ | H | H |
| C6 | —CH$_2$CH$_2$C(O)N(piperidine) | H | H |
| C7 | —CH$_2$CH$_2$C(O)N(morpholine) | H | H |
| C8 | —CH$_2$CH$_2$C(O)N(CH$_2$CH$_3$)$_2$ | H | H |
| C9 | —CH$_2$CH$_2$C(O)NHCH$_2$CH$_2$N(morpholine) | H | H |
| C10 | —CH$_2$CH$_2$C(O)NHCH$_2$CH$_2$N(piperidine) | H | H |
| C11 | —CH$_2$CH$_2$C(O)NHCH$_2$CH$_2$N(pyrrolidine) | H | H |
| C12 | —CH$_2$CH$_2$C(O)NHCH$_2$CH$_2$N(Et)$_2$ | H | H |

TABLE C-continued

| Compound | R$^a$ | R$^b$ (at 6 position) | R$^c$ (at 5 position) |
|---|---|---|---|
| C13 | —CH$_2$C(O)NHCH$_2$CH$_2$N(morpholine) | H | H |
| C14 | —CH$_2$C(O)NHCH$_2$CH$_2$N(piperidine) | H | H |
| C15 | —CH$_2$C(O)NHCH$_2$CH$_2$N(pyrrolidine) | H | H |
| C16 | —CH$_2$C(O)NHCH$_2$CH$_2$N(Et)$_2$ | H | H |
| C17 | —CH$_2$C(O)N(piperazine)NCH$_2$CH$_3$ | H | H |
| C18 | —CH$_2$C(O)N(morpholine) | H | H |
| C19 | —C(O)NHCH$_2$CH$_2$N(morpholine) | H | H |
| C20 | —C(O)NHCH$_2$CH$_2$N(piperidine) | H | H |
| C21 | —C(O)NHCH$_2$CH$_2$N(pyrrolidine) | H | H |
| C22 | —C(O)NHCH$_2$CH$_2$N(Et)$_2$ | H | H |
| C23 | —C(O)N(piperazine)NCH$_2$CH$_3$ | H | H |
| C24 | —C(O)N(piperazine)NH | H | H |
| C25 | —C(O)N(piperazine)NCH$_3$ | H | H |
| C26 | —C(O)OCH$_2$CH$_3$ | H | H |
| C27 | —C(O)OH | H | H |
| D1 | —CH$_2$CH$_2$CH$_2$N(piperazine)NCH$_2$CH$_3$ | H | H |
| D3 | —CH$_2$CH$_2$CH$_2$N(morpholine) | H | H |
| D4 | —CH$_2$CH$_2$CH$_2$N(piperidine) | H | H |

TABLE C-continued

| Compound | $R^a$ | $R^b$ (at 6 position) | $R^c$ (at 5 position) |
|---|---|---|---|
| D5 |  | H | H |
| D6 | 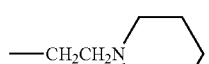 | H | H |
| D7 | 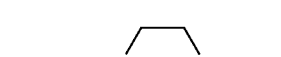 | H | H |
| D8 | 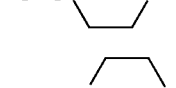 | H | H |
| D9 | 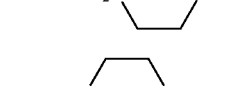 | H | H |
| D10 | 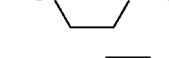 | H | H |

Exemplary compounds provided also include:

3-(2-{4-[3-(5-tert-Butyl-isoxazol-3-yl)-ureido]-phenyl}-benzo[d]imidazo[2,1-b]thiazol-7-yl)-N-(2-morpholin-4-yl-ethyl)-propionamide;

3-(2-{4-[3-(5-tert-Butyl-isoxazol-3-yl)-ureido]-phenyl}-benzo[d]imidazo[2,1-b]thiazol-7-yl)-N-(2-piperidin-1-yl-ethyl)-propionamide;

3-(2-{4-[3-(5-tert-Butyl-isoxazol-3-yl)-ureido]-phenyl}-benzo[d]imidazo[2,1-b]thiazol-7-yl)-N-(2-pyrrolidin-1-yl-ethyl)-propionamide;

3-(2-{4-[3-(5-tert-Butyl-isoxazol-3-yl)-ureido]-phenyl}-benzo[d]imidazo[2,1-b]thiazol-7-yl)-N-(2-diethylamino-ethyl)-propionamide;

1-(5-tert-Butyl-isoxazol-3-yl)-3-{4-[7-(4-methyl-piperazin-1-yl)-benzo[d]imidazo[2,1-b]thiazol-2-yl]-phenyl}-urea;

1-(5-tert-Butyl-isoxazol-3-yl)-3-(4-{7-[2-(4-methyl-piperazin-1-yl)-ethoxy]-benzo[d]imidazo[2,1-b]thiazol-2-yl}-phenyl)-urea;

1-(5-tert-Butyl-isoxazol-3-yl)-3-{4-[7-(2-piperidin-1-yl-ethoxy)-benzo[d]imidazo[2,1-b]thiazol-2-yl]-phenyl}-urea;

1-(5-tert-Butyl-isoxazol-3-yl)-3-{4-[7-(3-morpholin-4-yl-propoxy)-benzo[d]imidazo[2,1-b]thiazol-2-yl]-phenyl}-urea;

1-(5-tert-Butyl-isoxazol-3-yl)-3-(4-{7-[3-(4-methyl-piperazin-1-yl)-propoxy]-benzo[d]imidazo[2,1-b]thiazol-2-yl}-phenyl)-urea;

1-(5-tert-Butyl-isoxazol-3-yl)-3-(4-{7-[3-(4-methanesulfonyl-piperazin-1-yl)-propoxy]-benzo[d]imidazo[2,1-b]thiazol-2-yl}-phenyl)-urea;

N-(5-tert-Butyl-isoxazol-3-yl)-N'-(4-{7-[3-(4-ethyl-piperazin-1-yl)propyl]imidazo[2,1-b][1,3]benzothiazol-2-yl}phenyl)-urea;

1-(5-tert-Butyl-isoxazol-3-yl)-3-{4-[7-(3-morpholin-4-yl-3-oxo-propyl)-benzo[d]imidazo[2,1-b]thiazol-2-yl]-phenyl}-urea;

3-(5-tert-Butyl-isoxazol-3-yl)-1-methyl-1-{4-[7-(3-morpholin-4-yl-propyl)-benzo[d]imidazo[2,1-b]thiazol-2-yl]-phenyl}-urea;

1-(5-tert-Butyl-isoxazol-3-yl)-3-{4-[7-(3-morpholin-4-yl-propyl)-benzo[d]imidazo[2,1-b]thiazol-2-yl]-phenyl}-urea;

N-(5-tert-Butyl-isoxazol-3-yl)-N'-{4-[7-(2-morpholin-4-yl-ethoxy)imidazo[2,1-b]benzothiazol-2-yl]phenyl}urea;

1-(5-tert-Butyl-isoxazol-3-yl)-3-[4-(7-morpholin-4-yl-benzo[d]imidazo[2,1-b]thiazol-2-yl)-phenyl]-urea;

N-(5-tert-Butyl-isoxazol-3-yl)-N'-{4-[7-(3-piperidin-1-yl-propyl)imidazo[2,1-b][1,3]benzothiazol-2-yl]phenyl}urea;

N-(5-tert-butyl-isoxazol-3-yl)-N'-{4-[5-(2-morpholin-4-yl-ethoxy)imidazo[2,1-b][1,3]benzothiazol-2-yl]phenyl}urea;

2-(2-{4-[3-(5-tert-Butyl-isoxazol-3-yl)-ureido]-phenyl}-benzo[d]imidazo[2,1-b]thiazol-7-yl)-N-(2-morpholin-4-yl-ethyl)-acetamide;

2-(2-{4-[3-(5-tert-Butyl-isoxazol-3-yl)-ureido]-phenyl}-benzo[d]imidazo[2,1-b]thiazol-7-yl)-N-(2-piperidin-1-yl-ethyl)-acetamide;

2-(2-{4-[3-(5-tert-Butyl-isoxazol-3-yl)-ureido]-phenyl}-benzo[d]imidazo[2,1-b]thiazol-7-yl)-N-(2-pyrrolidin-1-yl-ethyl)-acetamide;

1-(5-tert-Butyl-isoxazol-3-yl)-3-(4-{7-[2-(4-ethyl-piperazin-1-yl)-2-oxo-ethyl]-benzo[d]imidazo[2,1-b]thiazol-2-yl}-phenyl)-urea;

1-(5-tert-Butyl-isoxazol-3-yl)-3-[4-(7-hydroxy-benzo[d]imidazo[2,1-b]thiazol-2-yl)-phenyl]-urea;

1-(5-tert-Butyl-isoxazol-3-yl)-3-[4-(7-methoxy-benzo[d]imidazo[2,1-b]thiazol-2-yl)-phenyl]-urea;

1-(5-tert-Butyl-isoxazol-3-yl)-3-{4-[7-(2-diethylamino-ethoxy)-benzo[d]imidazo[2,1-b]thiazol-2-yl]-phenyl}-urea;

ethyl {2-[4-({[(5-tert-Butylisoxazol-3-yl)amino]carbonyl}amino)phenyl]imidazo[2,1-b][1,3]benzothiazol-7-yl}acetate;

3-{2-[4-({[(5-tert-Butylisoxazol-3-yl)amino]carbonyl}amino)phenyl]imidazo[2,1-b][1,3]benzothiazol-7-yl}acetic acid;

pyrrolidine-2-carboxylic acid 2-{4-[3-(5-tert-butyl-isoxazol-3-yl)-ureido]-phenyl}-benzo[d]imidazo[2,1-b]thiazol-7-yl ester;
ethyl 3-{2-[4-({[(5-tert-Butylisoxazol-3-yl)amino]carbonyl}amino)phenyl]imidazo[2,1-b][1,3]benzothiazol-7-yl}propanoate;
3-{2-[4-({[(5-tert-Butylisoxazol-3-yl)amino]carbonyl}amino)phenyl]imidazo[2,1-b][1,3]benzothiazol-7-yl}propanoic acid;
3-(2-{4-[3-(5-tert-Butyl-isoxazol-3-yl)-ureido]-phenyl}-benzo[d]imidazo[2,1-b]thiazol-7-yl)-N, N-diethyl-propionamide;
2-(2-{4-[3-(5-tert-Butyl-isoxazol-3-yl)-ureido]-phenyl}-benzo[d]imidazo[2,1-b]thiazol-7-yl)-N-(2-diethylaminoethyl)-acetamide;
2-Amino-3-methyl-butyric acid 2-{4-[3-(5-tert-butyl-isoxazol-3-yl)-ureido]-phenyl}-benzo[d]imidazo[2,1-b]thiazol-7-yl ester;
1-(4-Benzo[d]imidazo[2,1-b]thiazol-2-yl-phenyl)-3-(5-tert-butyl-isoxazol-3-yl)-urea;
1-(5-tert-Butyl-isoxazol-3-yl)-3-[4-(7-fluoro-benzo[d]imidazo[2,1-b]thiazol-2-yl)-phenyl]-urea; and
1-(5-tert-Butyl-isoxazol-3-yl)-3-[4-(7-methyl-benzo[d]imidazo[2,1-b]thiazol-2-yl)-phenyl]-urea.

In one embodiment, compounds and compositions provided herein are effective in methods of modulating the activity of the platelet derived growth factor receptor (PDGFR) subfamily, which includes PDGFR α, PDGFR β, CSF-1R, c-kit and Flt3.

In one embodiment, compounds and compositions provided herein are effective to modulate the activity the fetus liver kinase ("flk") receptor subfamily, which includes kinase insert domain-receptor fetal liver kinase-1 (KDR/FLK-1), flk-1R, flk-4 and fms-like tyrosine kinase 1 (flt-1).

In another aspect, compounds and compositions provided herein are effective to modulate the activity of the "HER" receptor tyrosine kinase subfamily, which includes EGFR (epithelial growth factor receptor), HER2, HER3 and HER4.

In another aspect, compounds and compositions provided herein are effective to modulate the activity of the insulin receptor (IR) sub family which includes insulin-like growth factor I receptor (IGF-1R).

In one embodiment, compounds and compositions provided herein are effective to modulate the activity of the vascular endothelial growth factor ("VEGF") receptor subgroup.

In one embodiment, compounds and compositions provided herein are effective to modulate the activity of the fibroblast growth factor ("FGF") receptor subgroup, which includes the receptors FGFR1, FGFR 2, FGFR3, and FGFR4, and the ligands, FGF1, FGF2, FGF3, FGF4, FGF5, FGF6, and FGF7.

In another aspect, compounds and compositions provided herein are effective to modulate the activity of the c-Met receptor family.

In another aspect, compounds and compositions provided herein are effective to modulate the activity of the Abl protein tyrosine family.

In one embodiment, compounds and compositions provided herein are effective to modulate the activity of the fms-like tyrosine kinase 3 receptor kinase (FLT-3 kinase).

In one embodiment, compounds and compositions provided herein are effective to modulate the activity of the Src subfamily, which includes Src, Yes, Fyn, Lyn, Lck, Blk, Hck, Fgr and Yrk.

In one embodiment, compounds and compositions provided herein are effective to modulate the activity of one or more kinases selected from the group consisting of sterile 20, sterile 11, sterile, the camk sub family (calmodulin regulated kinases and related kinases), the AGC sub family (protein kinase A, protein kinase G and protein kinase C), the CMGC sub family (cdk, map kinase, glycogen synthetase kinase and elk), the sterile 20 sub family, and Frk, Btk, Csk, Abl, Zap70, Fes, Fps, Fak, Jak and Ack, (and their respective subfamilies).

In another embodiment, provided herein are methods of using the disclosed compounds and compositions, or pharmaceutically acceptable salts, solvates, hydrates or prodrugs thereof, for the local or systemic treatment or prophylaxis of human and veterinary diseases, disorders and conditions modulated or otherwise affected mediated via kinase activity.

C. Formulation of Pharmaceutical Compositions

The pharmaceutical compositions provided herein contain therapeutically effective amounts of one or more of compounds provided herein that are useful in the prevention, treatment, or amelioration of protein kinase mediated diseases or one or more of the symptoms thereof.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art.

In the compositions, effective concentrations of one or more compounds or pharmaceutically acceptable salt, solvate, hydrate or prodrug is (are) mixed with a suitable pharmaceutical carrier or vehicle. The concentrations of the compounds in the compositions are effective for delivery of an amount, upon administration, that treats, prevents, or ameliorates one or more of the symptoms of protein kinase mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of protein kinase mediated diseases.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 1 mg, 20 mg, 25 mg, 50 mg, 100 mg, 250 mg, 500 mg, 1000 mg or 2000 mg of the essential active ingredient. In certain embodiments, the pharmaceutical dosage unit forms are prepared to provide about 50 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing protein kinase mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as protein kinase mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. In one embodiment, the composition is administered as an aqueous solution with hydroxypropyl-beta-cyclodextrin (HPBCD) as an excipient. In one embodiment, the aqueous solution contains about 1% to about 50% HPBCD. In one embodiment, the aqueous solution contains about 1%, 3%, 5%, 10% or about 20% HPBCD.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, hydroxypropyl-beta-cyclodextrin (HPBCD) or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, 100-500 mg, 10-500 mg, 50-250 mg or 25-100 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used. In another embodiment, polymeric materials can be used. In yet another embodiment, a controlled release system can be placed in proximity of the therapeutic target, i.e., thus requiring only a fraction of the systemic dose. In some embodiments, a controlled release device is introduced into a subject in proximity of the site of inappropriate immune activation or a tumor. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

D. Evaluation of the Activity of the Compounds

Standard physiological, pharmacological and biochemical procedures are available for testing the compounds to identify those that possess biological activities that selectively modulate the activity of kinases.

Such assays include, for example, biochemical assays such as binding assays, radioactivity incorporation assays, fluorescence polarization assays, fluorescence resonance energy transfer (FRET) based assays (see generally Glickman et al., *J. Biomolecular Screening*, 7 No. 1 3-10 (2002)), as well as a variety of cell based assays.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

In one embodiment, inhibition is determined in vitro. In a specific embodiment, inhibition is assessed by phosphorylation assays. Any suitable phosphorylation assay can be employed. For example, membrane autophosphorylation assays, receptor autophosphorylation assays in intact cells, and ELISA's can be employed. See, e.g., Gazit, et al., *J. Med. Chem.* (1996) 39:2170-2177, Chapter 18 in CURRENT PROTOCOLS IN MOLECULAR BIOLOGY (Ausubel, et al., eds. 2001).

In addition a variety of cell based assay methodologies can be successfully used in screening assays to identify and profile the specificity of compounds provided herein. Cells useful in such assays include cells with wildtype or mutated forms. In one embodiment, the wildtype is a kinase that is not constitutively active, but is activated with upon dimerization. For example, the mutant FLT3 kinase is constitutively active via internal tandem duplication mutations or point mutations in the activation domain. Suitable cells include those derived through cell culture from patient samples as well as cells derived using routine molecular biology techniques, e.g., retroviral transduction, transfection, mutagenesis, etc. Exemplary cells include Ba/F3 or 32Dc13 cells transduced with, e.g., MSCV retroviral constructs FLT3-ITD (Kelly et al., 2002); Molm-13 and Molm14 cell line (Fujisaki Cell Center, Okayama, Japan); HL60 (AML-M3), AML193 (AML-M5), KG-1, KG-Ia, CRL-1873, CRL-9591, and THP-1 (American Tissue Culture Collection, Bethesda, Md.); or any suitable cell line derived from a patient with a hematopoietic malignancy.

In some embodiments, the compounds described herein significantly inhibit receptor tyrosine kinases. A significant inhibition of a receptor tyrosine kinase activity refers to an $IC_{50}$ of less than or equal to 100 µM. In one embodiment, the compound can inhibit activity with an $IC_{50}$ of less than or equal to 50 µM, in other embodiment, less than or equal to 10 µM, in other embodiment, less than 1 µM, less than 100 nM or less than 50 nM. Lower $IC_{50}$'s are preferred because the $IC_{50}$ provides an indication as to the in vivo effectiveness of the compound. Other factors known in the art, such as compound half-life, biodistribution, and toxicity should also be considered for therapeutic uses. Such factors may enable a compound with a lower $IC_{50}$ to have greater in vivo efficacy than a compound having a higher $IC_{50}$. In one embodiment, a compound that inhibits activity is administered at a dose where the effective tyrosine phosphorylation, i.e., $IC_{50}$, is less than its cytotoxic effects, $LD_{50}$.

Compound binding may also be determined using phage display of fusion proteins exposed on the outer surface of the phage head, for example using an affinity based phage display screening system as described in Fabian et al., (*Nat Biotechnol.* 2005 23(3):329-36). This approach employs a competition binding assay to determine the relative affinity of a compound of interest to a protein expressed as a fusion protein on the surface of the T7 bacteriophage. The assay uses phage tagged with a kinase of interest and an immobilized bait which are combined with the compound to be tested. A test compound which binds to the kinase directly or indirectly competes with the immobilized bait and prevents the binding of the phage-tagged kinase to the solid support. If the compound does not bind to the kinase, the tagged phage can bind to the solid support through the interaction between the kinase and the immobilized bait. The results can be read out by quantifying the amount of fusion protein bound to the solid support, which can be accomplished by either traditional plaque assays or by quantitative PCR (QPCR) using the phage genome as a template.

E. Methods of Use of the Compounds and Compositions

Also provided herein are methods of using the disclosed compounds and compositions, or pharmaceutically acceptable salts, solvates, hydrates or prodrugs thereof, for the treatment, prevention, or amelioration of a disease or disorder that is mediated or otherwise affected via protein kinase activiy or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7:334-339 (1994)). Consistent with the description above, such diseases or disorders include without limitation:

1) carcinomas include Kit-mediated carcinomas, adenocarcinoma, squamous cell carcinoma, adenosquamous carcinoma, teratocarcinoma, head and neck cancer, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including flt-3 and/or Kit-mediated small cell lung cancer, stomach/gastric cancer, gastrointestinal cancer, gastrointestinal stromal tumors (GIST) including Kit-mediated GIST and PDGFRα-mediated GIST, colon cancer, colorectal cancer, pancreatic cancer, islet cell carcinoma, hepatic/liver cancer, metastases to the liver, bladder cancer, renal cell cancer including PDGFR-mediated renal cell cancer, cancers of the genitourinary tract, ovarian cancer including Kit-mediated and/or PDGFR-mediated ovarian cancer, endometrial cancer including CSF-1R-mediated endometrial cancer, cervical cancer, breast cancer including Flt-3-mediated and/or PDGFR-mediated breast cancer, prostate cancer including Kit-mediated prostate cancer, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF-1R-mediated bone metastases, metastatic tumors including VEGFR-mediated tumors, stromal tumors, neuroendocrine tumors, tumor angiogenesis including VEGFR-mediated tumor angiogenesis, mixed mesodermal tumors;

b) sarcomas including PDGFR-mediated sarcomas, osteosarcoma, osteogenic sarcoma, bone cancer, glioma including PDGFR-mediated and/or CSF-1R-mediated glioma, astrocytoma, vascular tumors including VEGFR-mediated vascular tumors, Kaposi's sarcoma, carcinosarcoma, hemangiosarcomas including VEGFR3-mediated hemangiosarcomas, lymphangiosarcoma including VEGFR3-mediated lymphangiosarcoma;

c) myeloma, leukemia, myeloproliferative diseases, acute myelogenous leukemia (AML) including flt-3 mediated and/or KIT-mediated and/or CSF1R-mediated acute myeloid leukemia, chronic myelogenous leukemias (CML) including Flt-3-mediated and/or PDGFR-mediated chronic myeloid leukemia, myelodysplastic leukemias including Flt-3-mediated myelodysplastic leukemia, myelodysplastic syndrome, including Flt-3 mediated and/or Kit-mediated myelodysplastic syndrome, idiopathic hypereosinophilic syndrome (HES) including PDGFR-mediated HES, chronic eosinophilic leukemia (CEL) including PDGFR-mediated CEL, chronic myelomonocytic leukemia (CMML), mast cell leukemia including Kit-mediated mast cell leukemia, or systemic mastocytosis including Kit-mediated systemic mastocytosis; and d) lymphoma, lymphoproliferative diseases, acute lymphoblastic leukemia (ALL), B-cell acute lymphoblastic leukemias, T-cell acute lymphoblastic leukemias, natural killer (NK) cell leukemia, B-cell lymphoma, T-cell lymphoma, and natural killer (NK) cell lymphoma, any of which may be Flt-3 mediated and/or PDGFR-mediated, Langerhans cell histiocytosis including CSF-1R-mediated and flt-3-mediated Langerhans cell histiocytosis, mast cell tumors and mastocytosis;

2) Nonmalignant proliferation diseases; atherosclerosis including PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated;

3) Inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), including any of the aforementioned diseases which are flt-3-mediated and/or CSF-1R-mediated; and 4) Infectious diseases mediated either via viral or bacterial pathogens and sepsis, including KIT-mediated sepsis.

Also provided are methods of modulating the activity, or subcellular distribution, of kinases in a cell, tissue or whole organism, using the compounds and compositions provided herein, or pharmaceutically acceptable derivatives thereof.

Kinases of high interest, i.e. those that mediate one or more of the aforementioned diseases or disorders, include without limitation the following enzymes:

1) The platelet derived growth factor receptor (PDGFR) subfamily, which includes PDGFR α, PDGFR β, CSF-1R, Kit and Flt3;
2) The vascular endothelial growth factor (VEGF) receptor subfamily, which includes VEGFR1 (Flt1), VEGFR2 (KDR or Flk1) and VEGFR3 (Flt4);
3) The insulin receptor (IR) subfamily which includes insulin-like growth factor I receptor (IGF-1R);
4) Ret;
5) The HER (EGFR) subfamily;
6) The FGFR subfamily;
7) The HGFR (Met) subfamily;
8) The Abl protein tyrosine subfamily;
9) The Src subfamily, which includes Src, Yes1, Fyn, Lyn, Lck, Blk, Hck, Fgr and Yrk;
10) Frk, Btk, Csk, Abl, Syk, Fes, Fps, Fak, Jak and Ack, (and their respective subfamilies);
11) A kinase selected form the group consisting of prostate-derived sterile 20, sterile 11 and sterile 7;
12) the cam kinase subfamily (calmodulin regulated kinases and related kinases);
13) the AGC subfamily; and
14) the CMGC sub family (cdk, map kinase, glycogen synthetase kinase and elk).

F. Combination Therapy

Furthermore, it will be understood by those skilled in the art that the compounds, isomers, prodrugs and pharmaceutically acceptable derivatives provided herein, including pharmaceutical compositions and formulations containing these compounds, can be used in a wide variety of combination therapies to treat the conditions and diseases described above. Thus, also contemplated herein is the use of compounds, isomers, prodrugs and pharmaceutically acceptable derivatives provided herein in combination with other active pharmaceutical agents for the treatment of the disease/conditions described herein.

In one embodiment, such additional pharmaceutical agents include without limitation anti-cancer agents, and anti-inflammatory agents.

The compound or composition provided herein, or pharmaceutically acceptable derivative thereof, may be administered simultaneously with, prior to, or after administration of one or more of the above agents.

Pharmaceutical compositions containing a compound provided herein or pharmaceutically acceptable derivative thereof, and one or more of the above agents are also provided.

Also provided is a combination therapy that treats or prevents the onset of the symptoms, or associated complications of cancer and related diseases and disorders comprising the administration to a subject in need thereof, of one of the compounds or compositions disclosed herein, or pharmaceutically acceptable derivatives thereof, with one or more anticancer agents.

G. Preparation of the Compounds

Starting materials in the synthesis examples provided herein are either available from commercial sources or via literature procedures (e.g., March *Advanced Organic Chemistry: Reactions, Mechanisms, and Structure*, (1992) 4th Ed.; Wiley Interscience, New York). All commercially available compounds were used without further purification unless otherwise indicated, $CDCl_3$ (99.8% D, Cambridge Isotope Laboratories) was used in all experiments as indicated. Proton ($^1H$) nuclear magnetic resonance (NMR) spectra were recorded on a Bruker Avance 300 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Shimadzu HPLC/MS instrument using reverse-phase conditions (acetonitrile/water, 0.05% acetic acid). HPLC was performed using Varian HPLC systems and columns. Flash chromatography was performed using Merck Silica Gel 60 (230-400 mesh) following standard protocol (Still et al. (1978) *J. Org. Chem.* 43:2923).

It is understood that in the following description, combinations of substituents and/or variables of the depicted formulae are permissible only if such contributions result in stable compounds under standard conditions.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that the compounds provided herein could exist as one or more isomers, that is E/Z isomers, enantiomers and/or diastereomers.

Compounds of formula (I) may be generally prepared as depicted in the following schemes, unless otherwise noted, the various substituents $R^1$-$R^3$, X, $Z^1$, $Z^2$, $Z^3$ and $R^4$ are as defined in the Summary section.

GENERAL SYNTHETIC SCHEMES AND EXAMPLES

Various embodiments are further illustrated by the following synthetic schemes and examples, which should not be construed as limiting in any way. The experimental procedures to generate the data shown are discussed in more detail below. For all formulations herein, multiple doses may be proportionally compounded as is known in the art. The coatings, layers and encapsulations are applied in conventional ways using equipment customary for these purposes.

The subject matter has been described in an illustrative manner, and it is to be understood that the terminology used is intended to be in the nature of description rather than of limitation. Thus, it will be appreciated by those of skill in the art that conditions such as choice of solvent, temperature of reaction, volumes, reaction time may vary while still producing the desired compounds. In addition, one of skill in the art will also appreciate that many of the reagents provided in the following examples may be substituted with other suitable reagents. See, e.g., Smith & March, *Advanced Organic Chemistry*, $5^{th}$ ed (2001).

General Synthesis of Urea Derivatives

Scheme 1

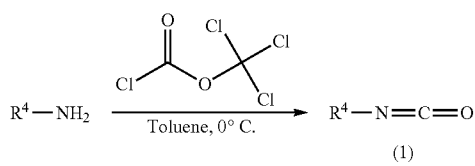

(1)

Certain ureas may be formed via the creation of isocyanato-intermediates followed by their reaction with aniline derivatives. The initial creation of the isocyanato intermediate (1) can be achieved via reaction of the corresponding amine derivative in dry toluene at 0° C. via the dropwise addition of trichloromethyl chloroformate (1.1 eq). Typically the reaction is stirred at 0° C. and allowed to warm to room temperature over night. The solvent may then be removed and the resulting mixture recrystallized in a suitable solvent system, for example ethyl acetate.

Intermediate (1) may then reacted with an appropriately substituted aniline derivative to form the corresponding urea.

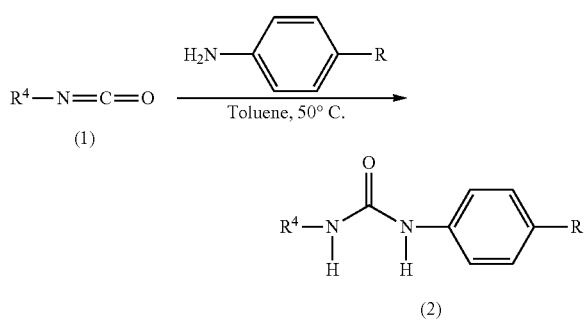

Generally the corresponding isocyanate derivative (1) is reacted with an appropriately substituted aniline (1 eq) dissolved in toluene at an elevated temperature. The reaction is typically allowed to stir at 50° C. for three to six hours. After completion of the reaction, the solvent is removed and the mixture purified by HPLC.

Conversion of Ureas to Thioureas

Scheme 2

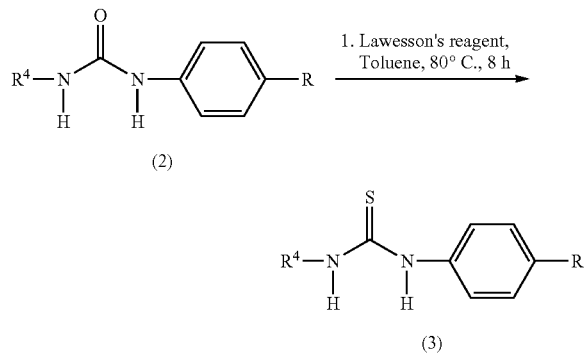

Ureas may be converted to thioureas via the use of Lawesson's reagent. In general, Lawesson's reagent is added to the starting urea in toluene and the reaction heated to 100° C. for 8 hours, then cooled, the solvent removed in vacuo and the thiourea purified by HPLC.

Synthesis of N-Substituted Ureas

Scheme 3

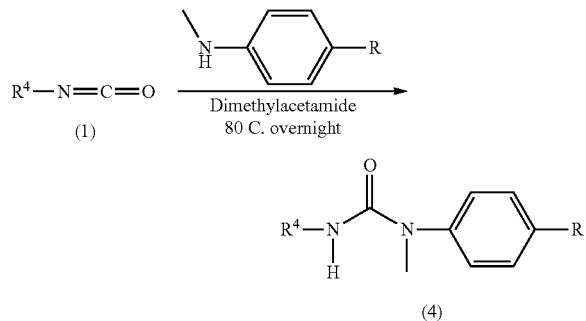

N-substituted ureas may be generated, provided that R does not contain reactive primary or secondary amines. Generally a solution of the corresponding isocyanate in dimethylacetamide is added to a solution of a corresponding N-alkylbenzenamine derivative, and the mixture is heated at 80° C. overnight. After cooling to room temperature, water is added and the mixture is extracted with EtOAc. The combined organic phases are washed with brine, dried over magnesium sulfate, and evaporated. Purification of the product may be accomplished by Flash chromatography (for example via silica gel, and using hexanes, 0-50% EtOAc as the solvent system).

General Synthesis of Benzothiazole and Benzoxazole Derivatives

Scheme 4

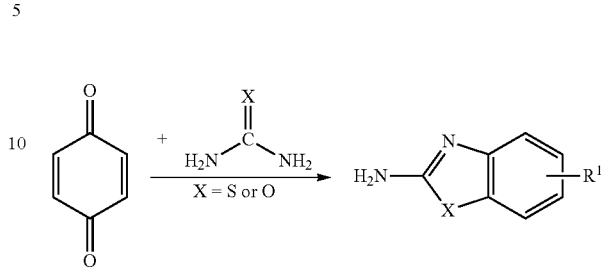

Appropriate 2-Amino-6-hydroxybenzo derivatives may be prepared according to a slightly modified literature procedure by Lau and Gompf: *J. Org. Chem.* 1970, 35, 4103-4108. Generally a stirred solution of thiourea or urea in a mixture of ethanol and concentrated hydrochloric acid was added a solution of 1,4-benzoquinone in hot ethanol. The reaction is typically stirred for 24 hours at room temperature and then concentrated to dryness. The residue is triturated with hot acetonitrile and the resulting solid filtered and dried. The free base is obtained by dissolving the hydrochloride salt in water, neutralizing with sodium acetate, and collecting the solid by filtration. The resulting compound is used below to form the corresponding benzyl derivative.

General Synthesis of Benzothiazole Isomers

Scheme 5

Two benzothiazole isomers shown below (2-amino-benzothiazol-4-ol and 2-amino-benzothiazol-6-ol) are commercially available.

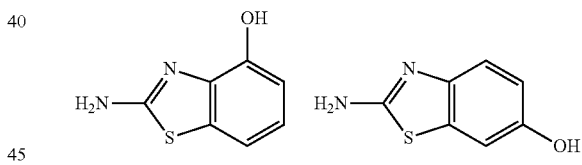

The two derivatives that are not commercially available (2-amino-benzothiazol-5-ol and 2-amino-benzothiazol-7-ol) can be obtained by cyclization of 3-methoxyaniline with ammoniumthiocyanate followed by demethylation with boron tribromide as outlined in the scheme below:

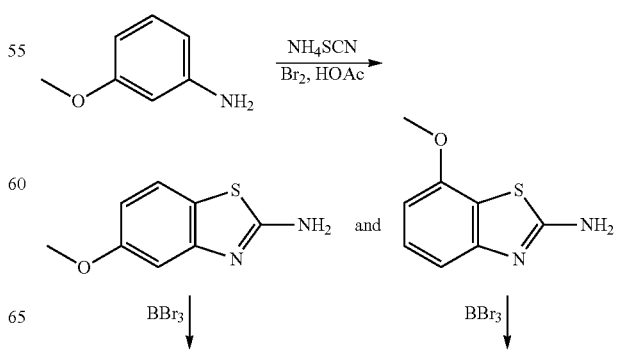

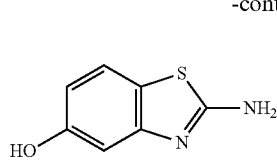
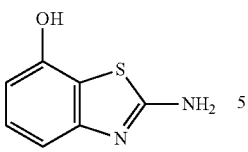

Ester substitutions on the benzothiazole can be obtained by cyclization of (4-amino)-phenyl acetic acid with ammoniumthiocyanate followed by methylation with the dropwise addition of concentrated sulfuric acid in methanol as outlined below:

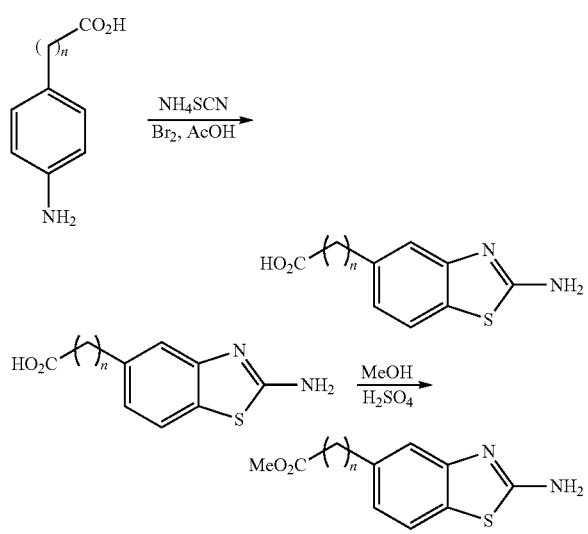

General Synthesis of Benzyl Derivatives

Scheme 6

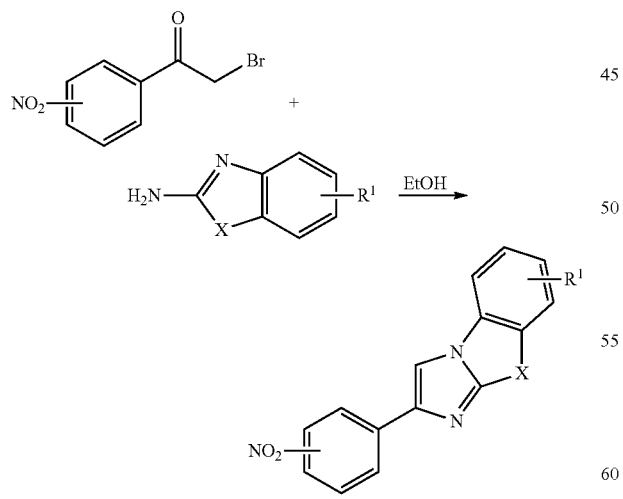

The product of the reaction from schemes 4 and 5 is reacted with 2'-bromo-4-nitroacetophenone dissolved in ethanol and typically heated to reflux overnight. The solution is then cooled to 0° C. in an ice-water bath and the product collected by vacuum filtration. After drying under vacuum with $P_2O_5$, the product may be isolated.

General Reduction Step

Scheme 7

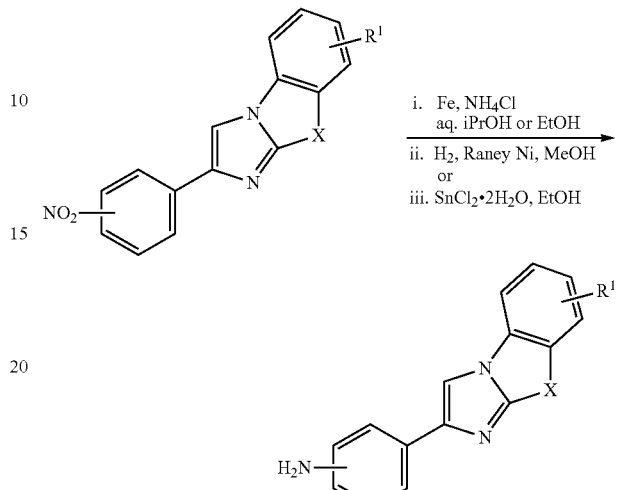

Any standard transition metal-mediated reactions as indicated in i, ii, or iii may be used to reduce the nitro group to the amine. Sulfur-mediated reductions or any other reduction methods known to those skilled in the art may also be used to reduce the nitro group. Typically, ammonium chloride and iron powder (i) are added to a suspension of the intermediate from Scheme 6 in an appropriate solvent (isopropyl alcohol/water (3:1) or 70% ethanol), then heated to reflux for 3 hours to overnight with vigorous stirring. The resulting mixture is filtered through Celite, and the filtercake washed with hot isopropyl alcohol (150 mL). The filtrate is concentrated, poured into saturated sodium bicarbonate, and extracted 3 times with dichloromethane. The combined organic phases are dried over $MgSO_4$ and concentrated to give the reduced intermediate. In an alternative reaction sequence where R1 group is modified into a solubilizing group in the final step, a suspension of the intermediate from Scheme 6 in ethanol can be mixed with tin chloride (iii) and heated to about 95° C. overnight. The mixture is then diluted with water, pH adjusted to about pH8 with $NaHCO_3$, and extracted three times with dichloromethane. The combined organic phases are dried over $MgSO_4$ and concentrated to give the reduced intermediate.

General Amine Coupling Reactions

Scheme 8

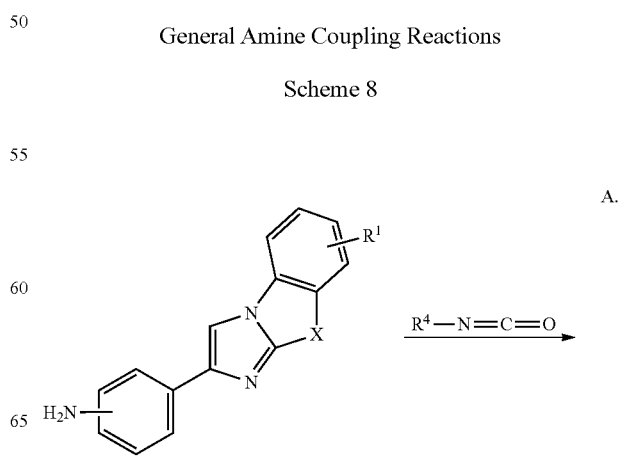

-continued

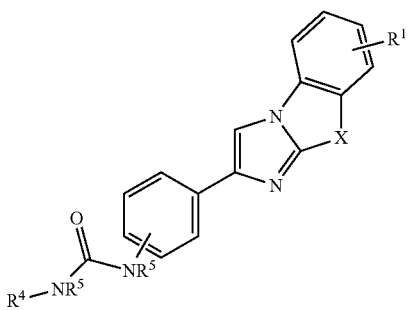

A. To form the urea, a suspension of the intermediate above is typically reacted with an appropriate isocyanate in toluene or an equivalent aprotic solvent and heated at 40-120° C. overnight. The reaction is quenched by pouring into a mixture of methylene chloride and water containing a little MeOH and neutralized with saturated aqueous NaHCO$_3$ solution. The aqueous phase is extracted twice with methylene chloride, the combined organic extracts are dried over MgSO$_4$ and filtered. The filtrate is concentrated and ethyl ether added to precipitate the product. The precipitate is collected by filtration, washed with ethyl ether, and dried under vacuum to give the free base.

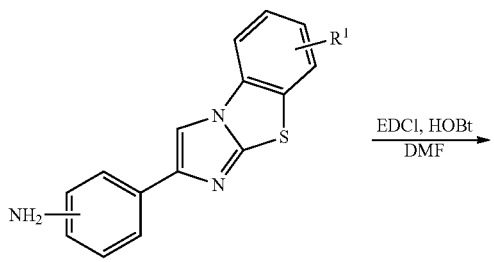

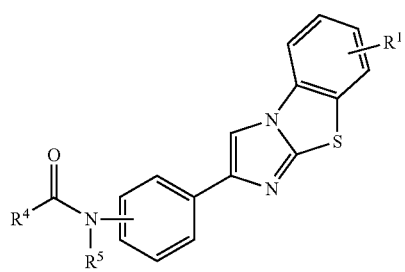

B. To form phenyl amides as shown above, generally, an appropriately substituted carboxylic acid is reacted under HOBt (1-hydroxybenzotriazole hydrate) and EDCl (N-(3-dimethylaminopropyl)-N'-ethylcarbodiimide hydrochloride) conditions in anhydrous DMF with the appropriately substituted benzo[d]imidazo[2,1-b]thiazol-2-yl-phenylamine.

Synthesis of Ether Derivatives

Scheme 9

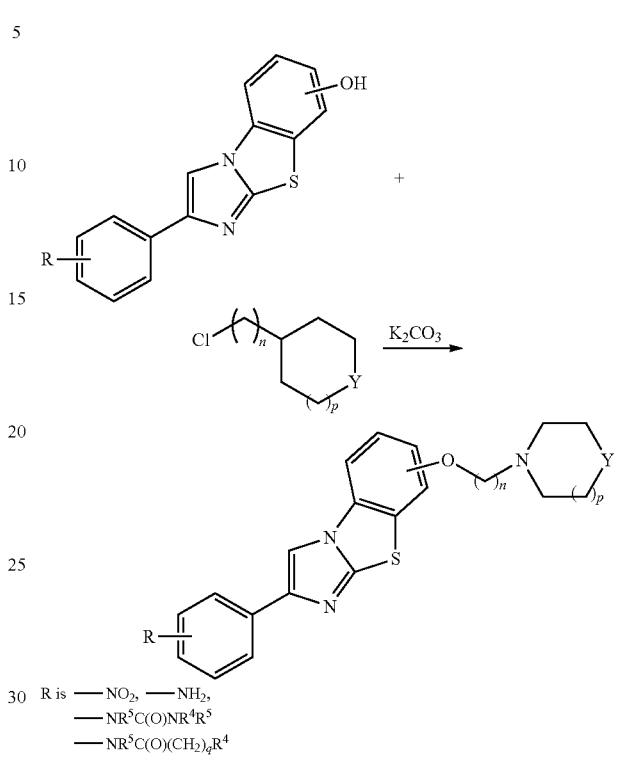

Generally the benzyl derivative is reacted with the appropriate chloroalkyl derivative in dry DMF. To this mixture is added potassium carbonate and optionally tetrabutyl ammonium iodide. The suspension is then heated to 80-90° C. for 5 to 8 hours or until the reaction is complete as determined by LCMS. The mixture is cooled to room temperature, poured into water, and allowed to sit for 1-3 hours. The resulting precipitate is collected by vacuum filtration and dried under vacuum. The resulting intermediate after reduction may then be coupled to a urea or amide derivative as depicted in Scheme 7 or 8. In an alternative synthetic sequence, this derivatization occurs after the coupling step to form the urea or amide.

General Scheme for Adding Carbon Chains Substituents

Scheme 10

The length of the carbon chain of the substituent on the benzo-portion of the imidazobenzothiazole ring may be adjusted by using the appropriate 4-amino phenyl carboxylic acid at the step of the benzothiazole formation (Scheme 5). After the second cyclicization step with 2'-bromo-4-nitroacetophenone (Scheme 6), reduction of the nitro group (Scheme 7) and coupling to form the amide or urea (Scheme 8), the resulting intermediate may be reacted with an amine to produce the amide analogs as shown below, which can then be reduced to amine analogs.

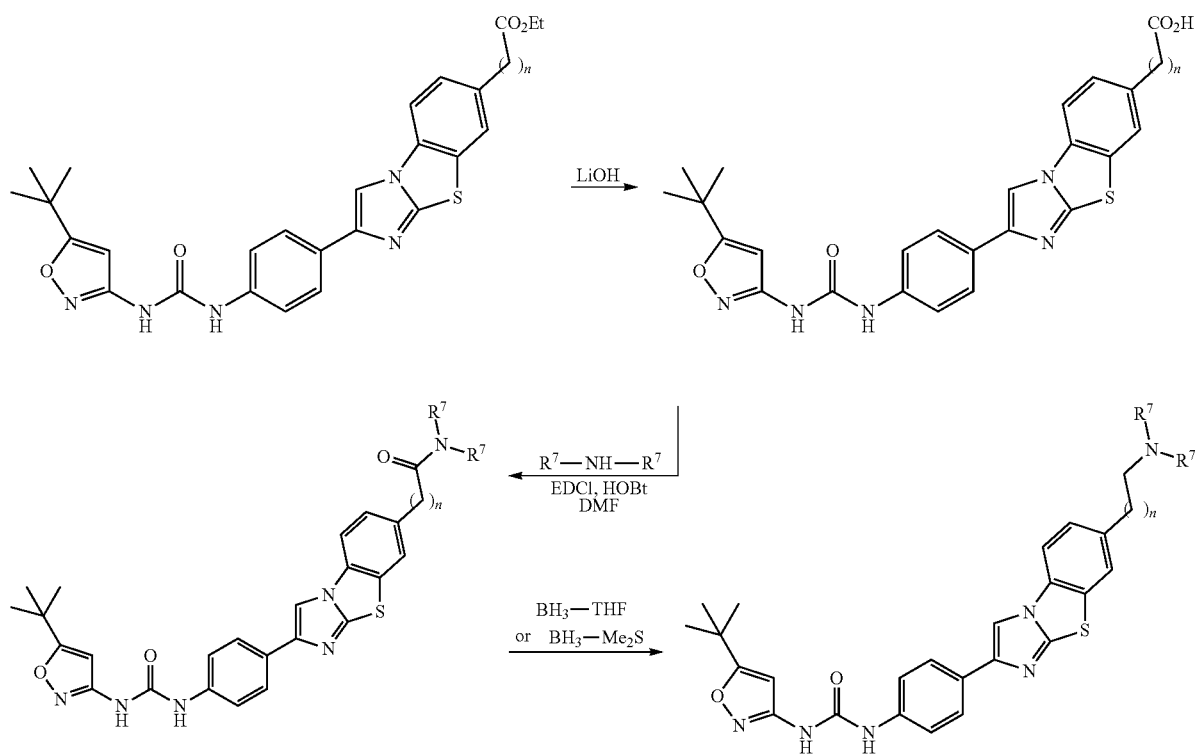

Alternatively, at the point of synthesis of [2-(4-nitro-phenyl)-imidazo[2,1b][1,3]benzothiazol-7-yl]acetate as shown below, the suspension of acetate may be reacted with lithium hydroxide, then reacted with the amine to form an amide analog, reduced with any number of reducing agents such as borane dimethylsulfide to afford an alkylamine substitutent and coupled finally with the appropriate isocyanate to produce the urea,

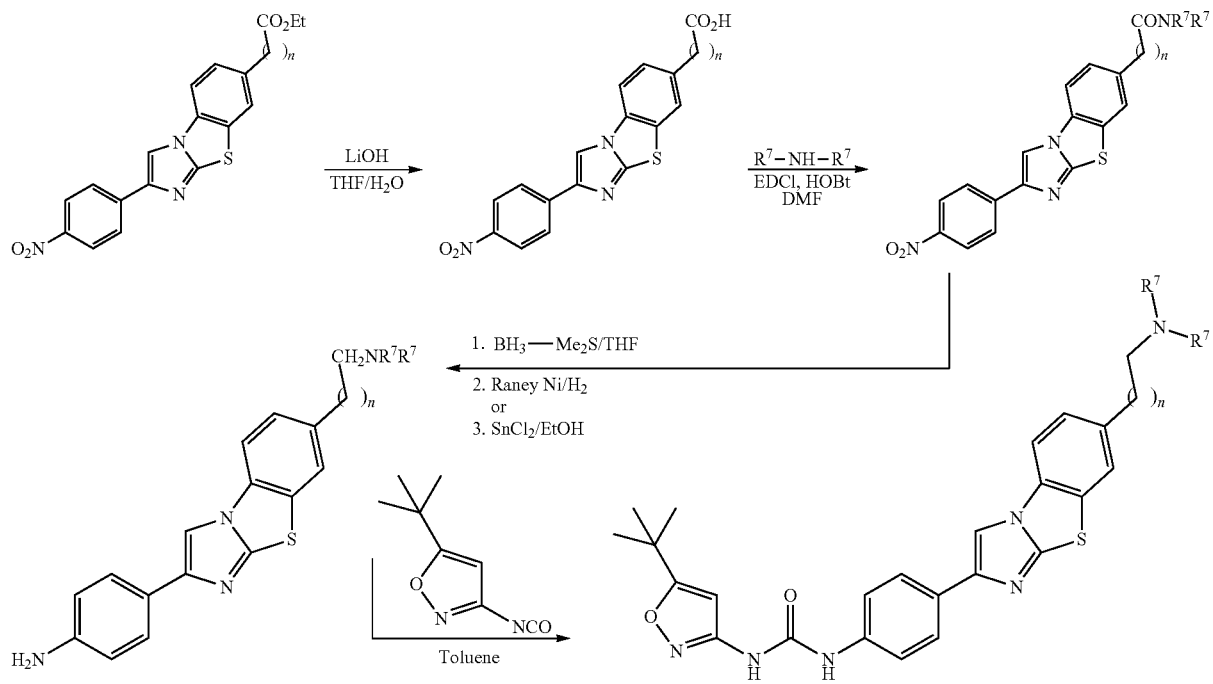

General Scheme for Alternative Urea Derivatives

Scheme 10

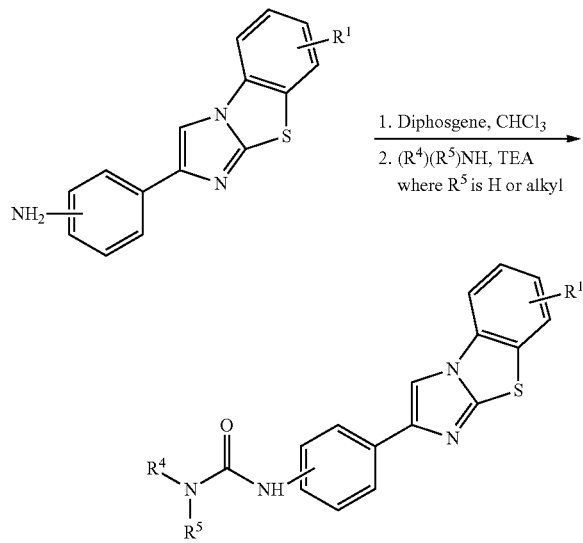

To introduce variations on the R⁴ position, ureas may be prepared in the following manner: An appropriately substituted benzo[d]imidazo[2,1-b]thiazol-2-yl]-phenylamine (1 eq.) is dissolved in 10 mL aprotic solvent (for example, anhydrous $CHCl_3$) and cooled to 0° C. Diphosgene or any phosgene equivalent (1.5 eq.) is added and the mixture stirred for 3 h while allowing to warm to room temperature. After evaporation of the solvent under vacuum at 20° C., the residue is dissolved in 10 mL anhydrous THF, and 1.4 eq. amine is added and the mixture stirred at between 25° C.-125° C. overnight. The solvent is evaporated under vacuum and the crude product purified by HPLC.

Preparation of 3-isocyanato-5-tert-butyl isoxazole from 3-amino-5-tert-butyl isoxazole

Scheme 11

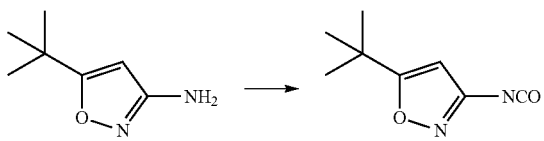

3-Amino-5-tert-butyl isoxazole in toluene and $CH_2Cl_2$ is cooled to −20° C. When the temperature reaches <10° C., triphosgene is added in one portion. Cooling is continued to <−20° C. Triethylamine in toluene is added drop-wise over 60 minutes at −20° C. to −15° C. The reaction mixture is stirred for 30 minutes at −20° C. to −15° C. after completion of the addition. The reaction is monitored by TLC: TLC should indicate ~80% isocyanate formation.

In certain embodiment, acid salts of the compounds provided herein can be prepared by addition of acid, including excess acid, to the free base prepared as described herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

Example 1

Preparation of N-(5-tert-Butyl-isoxazol-3-yl)-N'-imidazo[2,1-b][1,3]benzothiazol-2-yl]pheny}urea [Compound A1]

A. To prepare the intermediate 2-(4-nitrophenyl)imidazo[2,1-b][1,3]benzothiazole, 2-aminobenzothiazole (751 mg, 5 mmol) and 2-bromo-4'-nitroacetophenone (1.22 g, 5 mmol) were dissolved in ethanol and heated to reflux overnight. The solution was then cooled at room temperature for 24 hours. The precipitate was collected by filtration, washed with methanol and dried under vacuum.

B. To prepare the 2-(4-amino-phenyl)imidazo[2,1-b][1,3]benzothiazole, the intermediate from step A (428 mg, 1.5 mmol) was prepared as a suspension in isopropyl alcohol, and to it was added iron powder (419 mg, 7.5 mmol). The suspension was heated to reflux overnight with vigorous stirring. Completion of the reaction was confirmed by LCMS. 1N HCl was added to the mixture and allowed to cool to room temperature. The precipitate was collected by filtration and washed with several volumes of methanol to dissolve all organic material. The filtrates were evaporated and azeotroped with toluene. The resulting oil was added to cold saturated $NaHCO_3$ solution (20 mL) and sonicated. The suspension was diluted with toluene and azeotroped. The resulting residue was triturated with $CHCl_3$, and the precipitate filtered and washed with $CHCl_3$. The filtrates were concentrated and purified via Flash chromatography ($CH_2Cl_2$/5% MeOH/0.5% $Et_3N$)

C. To prepare the title compound, a suspension of the intermediate from Step B (133 mg, 0.5 mmol) and 5-tert-butylisoxazole-3-isocyanate (83 mg, 0.5 mmol) in methylene chloride was heated to 90° C. for two hours. The resulting suspension was concentrated and purified via Flash chromatography ($CH_2Cl_2$/MeOH). $^1$H NMR (DMSO-$d_6$) δ 9.65 (s, 1H), 8.9 (s, 1H), 8.7 (s, 1H), 8.05 (d, 1H), 7.95 (d, 1H), 7.8 (d, 2H), 7.65 (m, 3H), 7.4 (t, 1H), 6.55 (s, 1H), 1.3 (s, 9H); LC-MS (ESI) 432 (M+H)⁺

D. The following compounds were prepared from the appropriately functionalized 2-aminobenzothiazoles by cyclization with 2-bromo-4'-nitro acetophenone, followed by reduction and coupling with isoxazole isocyanate under reaction conditions described in Steps B and C.

1-(5-tert-butyl-isoxazol-3-yl)-3-[4-(7-fluoro-benzo[d]imidazo[2,1-b]thiazol-2-yl)-phenyl]-urea; LC-MS (ESI) 450 (M+H)⁺; [Compound A2]

1-(5-tert-butyl-isoxazol-3-yl)-3-[4-(7-methyl-benzo[d]imidazo[2,1-b]thiazol-2-yl)-phenyl]-urea; LC-MS (ESI) 445 (M+H)⁺; [Compound A3]

1-(5-tert-butyl-isoxazol-3-yl)-3-[4-(7-hydroxy-benzo[d]imidazo[2,1-b]thiazol-2-yl)-phenyl]-urea; $^1$H NMR (CDCl$_3$) 10.0 (s, 1H); 9.6 (s, 1H); 8.9 (s, 1H); 8.6 (s, 1H); 7.9 (m, 3H); 7.6 (m, 2H); 7.4 (s, 1H); 6.7 (s, 1H); 1.4 (s, 9H); and [Compound A4]

1-(5-tert-butyl-isoxazol-3-yl)-3-[4-(7-methoxy-benzo[d] imidazo[2,1-b]thiazol-2-yl)-phenyl]-urea; $^1$H NMR (methanol-$d_4$) 8.3 (s, 1H); 7.8 (d, 3H); 7.5 (m, 4H); 7.2 (d, 1H); 6.4 (s, 1H); 3.8 (s, 3H); 1.4 (s, 9H). [Compound A5]

Example 2

Preparation of 1-(5-tert-Butyl-isoxazol-3-yl)-3-[4-(7-morpholin-4-yl-benzo[d]imidazo[2,1-b]thiazol-2-yl)-phenyl]-urea; [Compound A6]

A. Preparation of the intermediate 6-morpholin-4-yl-benzothiazol-2-amine: To a solution of 4-N-morpholinoaniline (1.78 g, 10 mmol) in acetic acid (20 mL) was added NH$_4$SCN (2.28 g, 30 mmol) in small amounts several times. After stirring the mixture for 30 minutes, a solution of bromine in acetic acid (1.6 g in 5 mL) was added to the mixture and stirred overnight at room temperature. The mixture was then heated at 90° C. for 30 minutes, and then was cooled and neutralized with saturated NaHCO$_3$, and then extracted three times with CH$_2$Cl$_2$. The combined organic phases were dried over MgSO$_4$ and concentrated to dryness. To the residue was added 30 mL of 10% HCl and neutralized with saturated NaHCO$_3$, to give a brown solid (1.541 g, 66%).

B. Preparation of the intermediate 7-morpholin-4-yl-2-(4-nitro-phenyl)-imidazo[2,1-b][1,3]benzothiazole: A mixture of the intermediate from Step A (0.300 g, 1.27 mmol) and 2-bromo-4'-nitroacetophenone (0.341 g, 1.4 mmol) was combined in ethanol (10 mL) and heated to reflux overnight. The reaction was quenched with saturated NaHCO$_3$ and extracted with ethylacetate. The extract was concentrated and purified by SiO$_2$-Flash chromatography using 0-100% ethylacetate/hexane to give a brown solid (0.211 g, 44%).

C. Preparation of 4-(7-morpholin-4-yl-imidazo[2,1-b][1,3]benzothiazol-2-yl)phenylamine: A mixture of the intermediate from Step B (0.200 g, 0.53 mmol) and SnCl$_2$.2H$_2$O (0.600 g, 2.65 mmol) in ethanol (10 mL) was heated at 95° C. overnight. Completion of the reaction was confirmed by LCMS. The mixture was poured into 40 mL water and the pH was adjusted to 8 using saturated NaHCO$_3$, and then extracted three times with CH$_2$Cl$_2$. The combined organic phases were dried over MgSO$_4$ and concentrated. The residue was purified by SiO$_2$-Flash chromatography using methanol/ethyl acetate as eluants to give the reduced intermediate (0.112 g, 61%).

D. Preparation of the title compound: To a suspension of the intermediate in Step B (0.110 g, 0.3 mmol), was added 5-(tert-butyl) isoxazole-3-isocyanate (0.052 g, 0.3 mmol) in THF (10 mL) and heated to reflux overnight. Completion of the reaction was confirmed by LCMS. After removal of THF, the residue was purified by SiO$_2$-Flash chromatography using methanol/ethyl acetate as eluants to give the title compound as a solid (0.042 g, 27%); $^1$H NMR (CDCl$_3$) δ 9.3 (br, 1H), 7.84 (d and s, 3H), 7.60 (d, 2H), 7.50 (d and s, 2H), 7.19 (s, 1H), 7.04 (d, 1H), 5.84 (s, 1H), 3.90 (t, 4H), 3.19 (t, 4H), 1.36 (s, 9H).

E. 1-(5-tert-butyl-isoxazol-3-yl)-3-{4-[7-(4-methyl-piperazin-1-yl)-benzo[d]imidazo[2,1-b]thiazol-2-yl]-phenyl}-urea. was prepared in a manner similar to Steps A-D, except that in Step A, 6-morpholin-4-ylbenzothiazol-2-ylamine was substituted with 6-(4-methylpiperazin-1-yl)-1,3-benzothiazol-2-amine. $^1$H NMR (CDCl$_3$) δ 9.3 (br, 1H), 7.84 (d and s, 3H), 7.59 (br, 1H), 7.56 (d, 2H), 7.49 (d, 1H), 7.20 (d, 1H), 7.05 (dd, 1H), 5.86 (s, 1H), 3.250 (t, 4H), 2.62 (t, 4H), 2.38 (s, 3H), 1.36 (s, 9H). [Compound A7]

Example 3

Preparation of N-(5-tert-Butyl-isoxazol-3-yl)-N'-{4-[7-(2-morpholin-4-yl-ethoxy)imidazo[2,1-b][1,3]benzothiazol-2-yl]phenyl}urea [Compound B1]

A. The intermediate 2-amino-1,3-benzothiazol-6-ol was prepared according to a slightly modified literature procedure by Lau and Gompf: *J. Org. Chem.* 1970, 35, 4103-4108. To a stirred solution of thiourea (7.6 g, 0.10 mol) in a mixture of 200 mL ethanol and 9 mL concentrated hydrochloric acid was added a solution of 1,4-benzoquinone (21.6 g, 0.20 mol) in 400 mL of hot ethanol. The reaction was stirred for 24 hours at room temperature and then concentrated to dryness. The residue was triturated with hot acetonitrile and the resulting solid was filtered and dried.

The free base was obtained by dissolving the hydrochloride salt in water, neutralizing with sodium acetate, and collecting the solid by filtration. The product (2-amino-1,3-benzothiazol-6-ol) was obtained as a dark solid that was pure by LCMS (M+H=167) and NMR. Yield: 13.0 g (78%). NMR (DMSO-d$_6$) δ7.6 (m, 2H), 6.6 (d, 1H).

B. To prepare the intermediate 2-(4-nitrophenyl)imidazo[2,1-b][1,3]benzothiazol-7-ol, 2-amino-1,3-benzothiazol-6-ol, (20.0 g, 0.12 mol) and 2-bromo-4'-nitroacetophenone (29.3 g, 0.12 mol) were dissolved in 600 mL ethanol and heated to reflux overnight. The solution was then cooled to 0° C. in an ice-water bath and the product was collected by vacuum filtration. After drying under vacuum with P$_2$O$_5$, the intermediate (2-(4-nitrophenyl)imidazo[2,1-b][1,3]benzothiazol-7-ol) was isolated as a yellow solid. Yield: 17.0 g (46%) NMR (DMSO-d$_6$) δ 10 (s, 1H) 8.9 (s, 1H), 8.3 (d, 2H), 8.1 (d, 2H), 7.8 (d, 1H), 7.4 (s, 1H), 6.9 (d, 1H).

C. To make the 7-(2-morpholin-4-yl-ethoxy)-2-(4-nitro-phenyl)imidazo[2,1-b][1,3]benzothiazole intermediate: 2-(4-nitrophenyl)imidazo[2,1-b][1,3]benzothiazol-7-ol, (3.00 g, 9.6 mmol) was suspended in 100 mL dry DMF. To this mixture was added potassium carbonate (4.15 g, 30 mmol, 3 eq), chloroethyl morpholine hydrochloride (4.65 g, 25 mmol, 2.5 eq) and optionally tetrabutyl ammonium iodide (7.39 g, 2 mmol). The suspension was then heated to 90° C. for 5 hours or until complete by LCMS. The mixture was cooled to room temperature, poured into 800 mL water, and allowed to stand for 1 hour. The resulting precipitate was collected by vacuum filtration and dried under vacuum. The intermediate, (7-(2-morpholin-4-yl-ethoxy)-2-(4-nitro-phenyl)imidazo[2,1-b][1,3]benzothiazole) was carried on without further purification. Yield: 3.87 g (95%) NMR (DMSO-d$_6$) δ 8.97 (s, 1H), 8.30 (d, 2H), 8.0 (d, 2H), 7.9 (d, 1H), 7.7 (s, 1H), 7.2 (d, 1H), 4.1 (t, 2H), 5.6 (m, 4H), 2.7 (t, 2H).

D. To make the intermediate 7-(2-morpholin-4-yl-ethoxy)-2-(4-amino-phenyl)imidazo[2,1-b][1,3]benzothiazole: To a suspension of 7-(2-morpholin-4-yl-ethoxy)-2-(4-nitro-phenyl)imidazo[2,1-b][1,3]benzothiazole (3.87 g, 9.1 mmol) in 100 mL isopropyl alcohol/water (3:1) was added ammonium chloride (2.00 g, 36.4 mmol) and iron powder (5.04 g, 90.1 mmol). The suspension was heated to reflux overnight with vigorous stirring, completion of the reaction was confirmed by LCMS. The mixture was filtered through Celite, and the filtercake was washed with hot isopropyl alcohol (150 mL). The filtrate was concentrated to approximately ⅓ of the original volume, poured into saturated sodium bicarbonate, and extracted 3 times with dichloromethane. The combined organic phases were dried over MgSO$_4$ and concentrated to give the product as an orange solid containing a small amount (4-6%) of starting material. (Yield: 2.75 g 54%). 80% ethanol/water may be used in the place of isopropyl alcohol/ water—in which case the reaction is virtually complete after 3.5 hours and only traces of starting material are observed in the product obtained. NMR (DMSO-$d_6$) δ 8.4 (s, 1H), 7.8 (d, 1H), 7.65 (d, 1H), 7.5 (d, 2H), 7.1 (d, 1H), 6.6 (d, 2H), 4.1 (t, 2H), 3.6 (m, 4H), 2.7 (t, 2H).

E. A suspension of 7-(2-morpholin-4-yl-ethoxy)-2-(4-amino-phenyl)imidazo[2,1-b][1,3]benzothiazole (4.06 g, 10.3 mmol) and 5-tert-butylisoxazole-3-isocyanate (1.994 g, 12 mmol) in toluene was heated at 120° C. overnight. The reaction was quenched by pouring into a mixture of methylene chloride and water containing a little methanol and neutralized with saturated aqueous NaHCO$_3$ solution. The aqueous phase was extracted twice with methylene chloride, the combined organic extracts were dried over MgSO$_4$ and filtered. The filtrate was concentrated to about 20 ml volume and ethyl ether was added resulting in the formation of a solid. The precipitate was collected by filtration, washed with ethyl ether, and dried under vacuum to give the free base. Yield: 2.342 g (41%) NMR (DMSO-$d_6$) δ9.6 (br, 1H), 8.9 (br, 1H), 8.61 (s, 1H), 7.86 (d, 1H), 7.76 (d, 2H), 7.69 (d, 1H), 7.51 (d, 2H), 7.18 (dd, 1H), 6.52 (s, 1H), 4.16 (t, 2H), 3.59 (t, 4H), 3.36 (overlapping, 4H), 2.72 (t, 2H), 1.30 (s, 9H). NMR (CDCl$_3$) δ 9.3 (br, 1H), 7.84 (m, 4H), 7.59 (d, 2H), 7.49 (d, 1H), 7.22 (d, 1H), 7.03 (dd, 1H), 5.88 (s, 1H), 4.16 (t, 2H), 3.76 (t, 4H), 2.84 (t, 2H), 2.61 (t, 4H), 1.37 (s, 9H).

F. For the preparation of the hydrochloride salt, N-(5-tert-butyl-isoxazol-3-yl)-N'-{4-[7-(2-morpholin-4-yl-ethoxy)imidazo[2,1-b][1,3]benzothiazol-2-yl]phenyl}urea hydrochloride, the free base was dissolved in a mixture of 20 ml methylene chloride and 1 ml methanol. A solution of 1.0 M HCl in ethyl ether (1.1 eq.) was added dropwise, followed by addition of ethyl ether. The precipitate was collected by filtration or centrifugation and washed with ethyl ether to give the hydrochloride salt. Yield: 2.44 g (98%) NMR (DMSO-$d_6$) δ 11.0 (br, 1H), 9.68 (s, 1H), 9.26 (s, 1H), 8.66 (s, 1H), 7.93 (d, 1H), 7.78 (m, 3H), 7.53 (d, 2H), 7.26 (dd, 1H), 6.53 (s, 1H), 4.50 (t, 2H), 3.97 (m, 2H), 3.81 (t, 2H), 3.6 (overlapping, 4H), 3.23 (m, 2H), 1.30 (s, 9H).

G. Alternatively, Compound B1 may be made by taking the intermediate from Example 4B and reacting it with chloroethyl morpholine hydrochloride under conditions described in Step C.

H. N-(5-tert-butyl-isoxazol-3-yl)-N'-{4-[5-(2-morpholin-4-yl-ethoxy)imidazo[2,1-b][1,3]benzothiazol-2-yl]phenyl}urea hydrochloride, a compound having the general formula (I) where $R^1$ is substituted on the 5 position of the tricyclic ring, was prepared in the manner described in Steps A-F but using the cyclization product 2-amino-benzothiazol-4-ol with 2-bromo-4'-nitroacetophenone in Step A. $^1$H NMR (DMSO-$d_6$) δ 11.6 (br, 1H), 9.78 (br, 1H), 9.56 (br, 1H), 8.64 (s, 1H), 7.94 (d, 2H), 7.70 (s, 1H), 7.56 (d, 2H), 7.45 (t, 1H), 7.33 (d, 1H), 6.54 (s, 1H), 4.79 (t, 2H), 3.87 (m, 6H), 3.60 (m, 2H), 3.34 (m, 2H), 1.30 (s, 9H); LC-MS: ESI 561 (M+H)+. [Compound B11]

I. N-(5-tert-butyl-isoxazol-3-yl)-N'-{4-[6-(2-morpholin-4-yl-ethoxy)imidazo[2,1-b][1,3]benzothiazol-2-yl]phenyl}urea hydrochloride [Compound B12] was also prepared by first preparing the benzothiazole starting material, 5 methoxy-benzothiazol-2yl-amine:

To prepare the 5-methoxy-benzothiazol-2-ylamine starting material: To a suspension of (3-methoxy-phenyl)-thiourea (1.822 g, 10 mmol) in CH$_2$Cl$_2$ (20 mL) at 0° C. was added dropwise a solution of bromine (1.76 g, 11 mmol) in 10 ml of trichloromethane over a period of thirty minutes. The reaction was stirred for 3 hours at room temperature then heated to 3 hours to reflux for one hour. The precipitate was filtered and washed with dichloromethane. The solid was suspended in saturated NaHCO$_3$ and extracted with CH$_2$Cl$_2$. The extract was dried over MgSO$_4$ and concentrated to give a white solid (1.716 g, 95%).

To prepare the 2-amino-benzothiazol-5-ol: To a suspension of 5-methoxy-benzothiazol-2-ylamine in 16 mL of 48% HBr/H2O was heated to 105° C. in an oil bath for 10 hours. After the reaction was cooled to room temperature, the precipitate was collected by filtration and washed with acetone. The filtrate was suspended in saturated NaHCO$_3$ and extracted with CH$_2$Cl$_2$. The extract was dried over MgSO$_4$ and concentrated to give a white solid (0.986 g, 63%).

N-(5-tert-butyl-isoxazol-3-yl)-N'-{4-[6-(2-morpholin-4-yl-ethoxy)imidazo[2,1-b][1,3]benzothiazol-2-yl]phenyl}urea hydrochloride 2-amino-benzothiazol-5-ol from the previous step and following the method described in $^1$H NMR (DMSO-$d_6$) δ 11.1 (br, 1H), 9.69 (br, 1H), 9.28 (br, 1H), 8.71 (s, 1H), 7.97 (d, 1H), 7.79 (d and s, 3H), 7.56 (d, 2H), 7.13 (dd, 1H), 6.53 (s, 1H), 4.56 (t, 2H), 3.98 (m, 2H), 3.82 (t, 2H), 3.65 (m, 2H), 3.55 (m, 2H), 3.25 (m, 2H), 1.31 (s, 9H); LC-MS: ESI 561 (M+H)+, [Compound B12]

J. N-(5-tert-butyl-isoxazol-3-yl)-N'-{3-[7-(2-morpholin-4-yl-ethoxy)imidazo[2,1-b][1,3]benzothiazol-2-yl]phenyl}urea was prepared in a manner described in Steps A-E, but in which 2-bromo-3'-nitroacetophenone replaced 2-bromo-4'-nitroacetophenone in Step B; $^1$H NMR (DMSO-$d_6$) δ 11.1 (br, 1H), 9.76 (s, 1H), 9.34 (s, 1H), 8.76 (s, 1H), 8.01 (s, 1H), 8.05 (d, 1H), 7.79 (d, 1H), 7.50 (d, 1H), 7.37 (t, 1H), 7.32 (s, 1H), 7.27 (dd, 1H), 6.55 (s, 1H), 4.51 (t, 2H), 3.98 (m, 2H), 3.83 (t, 2H), 3.61 (m, 4H), 3.24 (m, 2H), 1.31 (a, 9H); LC-MS ESI: MH+ 561. [Compound B13]

K. 2-{3-[3-(5-tert-Butyl-isoxazol-3-yl)-ureido]-phenyl}-imidazo[2,1-b][1,3]benzothiazole-7-carboxylic acid ethyl ester was prepared in a manner described in Steps A-E, but in which Step B is carried out in the following manner: A mixture of 2-amine-benzothiazole-6-carboxylic acid ethyl ester (0.889 g, 4 mmol) and 2-bromo-3'-nitroacetophenone (1.220 g, 5 mmol) in DME (15 mL) was stirred at room temperature overnight. After the removal of DME, 2-methoxyethanol was added and heated at 140° C. for 4 hours. A yellow solid was formed, which was filtered, washed with ethanol and diethylether, and dried under vacuum (0.964 g, 66%); $^1$H NMR (DMSO-$d_6$) δ 9.60 (s, 1H), 8.96 (s, 1H), 8.64 (s, 1H), 8.70 (d, 1H), 8.14 (s, 3H), 7.52 (dd, 1H), 7.36 (t, 1H), 7.39 (t, 1H), 6.54 (s, 1H), 4.36 (q, 2H), 1.36 (t, 3H), 1.31 (s, 9H); LC-MS ESI: MH+ 504. [Compound B14]

Example 4

Preparation of 1-(5-tert-Butyl-isoxazol-3-yl)-3-{4-[7-(2-diethylamino-ethoxy)-benzo[d]imidazo[2,1-b]thiazol-2-yl]-phenyl}-urea [Compound B2]

A. To a suspension of the intermediate 2-(4-Nitrophenyl)imidazo[2,1-b][1,3]benzothiazol-7-ol from Example 3B (2.24 g, 7.2 mmol) in ethanol (40 mL) was added SnCl$_2$.H$_2$O (7.90 g, 35 mmol) and heated to reflux. Concentrated HCl was added to the reaction mixture and the precipitate formed gradually. The reaction mixture was heated to reflux for 20 hours and then allowed to cool to room temperature. The solution was poured into ice and neutralized with 10% NaOH and adjusted to approximately pH 6. The organic phase was extracted three times with ethylacetate (80 mL×3). Extracts were dried over MgSO$_4$ and concentrated to give a yellow solid. (1.621 g, 80%).

B. To a suspension of the intermediate from Step A (1.00 g, 3.55 mmol) in THF (20 mL) was added 5-tert-butylisoxazole-3-isocyanate (0.650 g, 3.9 mmol) and heated to reflux overnight in an oil bath at 90° C. Completion of reaction was verified by LC-MS. The solvent was removed and the resulting mixture was dissolved in methanol which was removed to give the second intermediate as a solid (1.103 g, 69%).

C. To a solution of 1-(5-tert-butyl-isoxazol-3-yl)-3-[4-(7-hydroxy-benzo[d]imidazo[2,1-b]thiazol-2-yl)-phenyl]-urea (0.25 g, 0.56 mmol) from Step B, 2-diethylamino-ethanol (0.094 g, 0.8 mmol), and triphenylphosphine (0.168 g, 0.8 mmol) in THF (6 mL) was dropped a solution of diisopropyl azodicarboxylate (0.162 g, 0.8 mmol) in THF (3 mL). The mixture was stirred at room temperature overnight. After solvent was evaporated, the residue was purified by preparative HPLC (C18 column eluting with MeCN/$H_2O$ containing 0.05% AcOH). The appropriate fractions were combined, neutralized with saturated $NaHCO_3$ solution, and extracted with $CH_2Cl_2$. Extracts were dried over $MgSO_4$ and concentrated to give the product as solid. $^1H$ NMR ($CDCl_3$) δ 9.3 (br, 1H), 8.3 (br, 1H), 7.83 (s, 1H), 8.81 (d, 2H), 7.56 (d, 2H), 7.47 (d, 1H), 7.20 (d, 1H), 7.0 (dd, 1H), 5.94 (s, 1H), 4.09 (t, 2H), 2.91 (t, 2H), 2.67 (q, 4H), 1.37 (s, 9H), 1.07 (t, 6H).

D. The free base from Step C (0.020 g) was dissolved in $CH_2Cl_2$ (0.5 mL) and to the solution was added dropwise 1.0 M HCl/dioxane. A solid was formed and the solvent was removed to afford the hydrochloride salt (0.020 g). $^1H$ NMR (DMSO-$d_6$) δ 10.1 (br, 1H), 9.67 (br, 1H), 9.24 (br, 1H), 8.66 (s, 1H), 7.93 (d, 1H), 7.76 (d and s, 3H), 7.54 (d, 2H), 7.24 (dd, 1H), 6.53 (s, 1H), 4.44 (t, 2H), 3.24 (m, 6H), 1.29 (s, 9H), 1.24 (t, 6H).

E. Alternative reaction sequence for Compound B2: To a suspension of the intermediate 2-(4-Nitrophenyl)imidazo[2,1-b][1,3]benzothiazol-7-ol from Example 3B (1.00 g, 3.2 mmol) in DMF (15 mL) was added potassium carbonate (1.38 g, 10 mmol) and (2-chloro-ethyl)diethylamine hydrochloride (0.826 g, 4.8 mmol) was heated to 80° C. overnight. Completion of the reaction was confirmed by LC-MS. 80 mL of water was added to the mixture, filtered and washed with water and diethylether to give the first intermediate as a yellow solid. The yellow solid intermediate was moved to a flask, and ammonium chloride (0.513 g, 9.6 mmol) and 80% ethanol (30 mL) was added and the mixture was heated to reflux at 100° C., at which point iron powder (1.787 g, 32 mmol) was added and the mixture continued to reflux at 100° C. for 3 hours. Completion of the reaction was confirmed by LC-MS. Ethanol (30 mL) was added to the mixture and heated. The precipitate was filtered and washed with hot ethanol. Saturated $NaHCO_3$ was added to the solution and the organic layer was extracted with $CH_2Cl_2$ and dried over $MgSO_4$ and concentrated to give the second intermediate as a solid (1.089 g). A suspension of this second intermediate (1.08 g, 2.8 mmol) in toluene (20 mL) was added 5-tert-butylisoxazole-3-isocyanate (0.605 g, 3.64 mmol) and the reaction was heated to 120° C. overnight. The reaction was quenched with $CH_2Cl_2$ and water with methanol, and basified with saturated $NaHCO_3$ to pH of about 8. The aqueous layer was extracted twice with $CH_2Cl_2$. The organic layers were combined, dried over $MgSO_4$ and concentrated to give the final product [Compound B2]. To the residue was purified by preparative HPLC (C18 column eluting with 35-65% $CH_3CN/H_2O$ containing 0.05% AcOH). The appropriate fractions were combined, the acetonitrile removed, and extracted with $CH_2Cl_2$. The extracts were dried over $MgSO_4$ and concentrated to give a white solid (0.894 g).

F. The compounds below were prepared in the manner described in Steps A-D:

1-(5-tert-Butyl-isoxazol-3-yl)-3-{4-[7-(2-piperidin-1-yl-ethoxy)-benzo[d]imidazo[2,1-b]thiazol-2-yl]-pheny}-urea hydrochloride; $^1H$ NMR ($CDCl_3$) δ 9.3 (br, 1H), 8.9 (br, 1H), 8.84 (s, 1H), 8.82 (d, 2H), 7.57 (d, 2H), 7.47 (d, 1H), 7.20 (d, 1H), 7.0 (dd, 1H), 5.89 (s, 1H), 4.15 (t, 2H), 2.81 (t, 2H), 2.53 (t, 4H), 1.63 (m, 4H), 1.5 (m, 2H), 1.37 (s, 9H). [Compound B3]

and 1-(5-tert-Butyl-isoxazol-3-yl)-3-(4-{7-[2-(4-methyl-piperazin-1-yl)-ethoxy]-benzo[d]imidazo[2,1-b]thiazol-2-yl}-phenyl)-urea hydrochloride; $^1H$ NMR ($CDCl_3$) δ 9.3 (br, 1H), 7.85 (s, 1H), 7.81 (d, 2H), 7.75 (br, 1H), 7.59 (d, 2H), 7.48 (d, 1H), 7.22 (d, 1H), 7.0 (dd, 1H), 5.87 (s, 1H), 4.16 (t, 2H), 2.87 (t, 2H), 2.65 (br, 4H), 2.5 (br, 4H), 2.31 (s, 3H), 1.37 (s, 9H). [Compound B4]

Example 5

Preparation of (2R)-2-amino-3-methyl-butyric acid 2-{4-[3-(5-tert-butyl-isoxazol-3-yl)-ureido]-phenyl}-benzo[d]imidazo[2,1-b]thiazol-7-yl ester [Compound B5]

A. The title compound was prepared in a manner similar to Example 3, but where the phenolic urea (0.125 g, 0.3 mmoles) was dissolved in anhydrous DMF (3 mL). To this solution was added potassium carbonate (0.082 g, 0.6 mmoles) and the Boc-L-valine N-hydroxysuccinimide (0.6 mmoles). The solution was stirred overnight at room temperature and then concentrated to dryness. The resulting solid was purified using HPLC with the appropriate fractions collected. These were concentrated to dryness and the resulting solid dissolved in methanol, and the solution treated with 4 M HCl in dioxane (2 mL). When cleavage of the Boc protecting group was complete by mass spectroscopy, the solution was concentrated to dryness. The solid was again dissolved in a minimal volume of methanol, and the hydrochloride precipitated by the addition of ethyl ether. NMR (DMSO-$d_6$) 8.2 (s, 1H); 7.8 (s, 1H); 7.7 (d, 1H); 7.6 (d, 2H); 7.5 (s, 2H); 7.4 (s, 1H); 7.2 (d, 2H); 6.6 (s, 1H); 6.3 (s, 1H); 4.2 (s, 1H); 2.2 (m, 1H); 1.3 (s, 9H); 1.0 (m, 6H). LC-MS: ESI 582 (M+H)$^+$.

B. In a manner similar to Step A, (2S)-pyrrolidine-2-carboxylic acid 2-{4-[3-(5-tert-butyl-isoxazol-3-yl)-ureido]-phenyl}-benzo[d]imidazo[2,1-b]thiazol-7-yl ester was made using Boc-L-proline N-hydroxysuccinimide; LC-MS: ESI 545 (M+H)$^+$. [Compound B6]

Example 6

Preparation of 1-(5-tert-butyl-isoxazol-3-yl)-3-{4-[7-(3-morpholin-4-yl-propoxy)-benzo[d]imidazo[2,1-b]thiazol-2-yl]-phenyl}-urea hydrochloride; [Compound B7]

A. The title compound was prepared in the manner described in Example 4A-D, but in which 2-diethylamino-ethanol was replaced with 3-morpholin-4-yl-propan-1-ol at Step C. $^1H$ NMR ($CDCl_3$) δ 9.35 (br, 1H), 7.87 (s, 1H), 7.83 (d, 2H), 7.59 (d, 2H), 7.51 (d, 1H), 7.45 (s, 1H), 7.22 (d, 1H), 7.02 (dd, 1H), 5.84 (s, 1H), 4.08 (t, 2H), 3.74 (t, 4H), 2.53 (m, 6H), 2.01 (m, 2H), 1.37 (s, 9H), LC-MS: ESI 575 (M+H)$^+$.

Example 7

Preparation of 1-(5-tert-butyl-isoxazol-3-yl)-3-(4-{7-[3-(4-methanesulfonyl-piperazin-1-yl)-propoxy]-benzo[d]imidazo[2,1-b]thiazol-2-yl}-phenyl)-urea. [Compound B10]

A. To prepare the intermediate 7-(3-chloro-propoxy)-2-(4-nitro-phenyl)-imidazo[2,1-b][1,3}benzothiazole, the intermediate from Example 3B (0.500 g, 1.6 mmol) was suspended in DMF, and to the suspension was added potassium carbonate (0.221 g, 1.6 mmol) and 1-bromo-4-chloropropane (0.756 g, 4.8 mmol). The suspension was then heated to 80° C. overnight. The mixture was concentrated to dryness and the crude product purified by Flash chromatography with silica gel using ethanol/hexane (0.440 g, 85%).

B. To prepare the intermediate 7-[3-(4-methanesulfonyl-piperazin-1-yl)-propoxy]-2-(4-nitro-phenyl)-imidazo[2,1-b][1,3]benzothiazole, the intermediate from Step A (1.37 g, 3.5 mmol) was suspended in DMF, and to the suspension was added tetrabutylammonium iodide (0.150 g) and 1-methane sulfonyl piperazine (1.20 g, 7.0 mmol). The suspension was then heated to 90° C. overnight. After the reaction was completed the mixture was poured into water, and filtered.

C. For reduction of the nitro intermediate from Step B to the amine: to the suspension of the intermediate from Step B in isopropyl alcohol (45 mL) was added 10% HCl, (5 mL) and iron powder (1.82 g). The suspension was heated to reflux for 2 hours and the completion of the reaction was verified by LCMS. The mixture was filtered and washed with methanol and DCM. The filtrate was concentrated, poured into saturated sodium bicarbonate and extracted three times with dichloromethane, (Yield: 1.00 g, 2.6 mmol).

D. Preparation of the title compound: to the intermediate from the Step C was dissolved in chloroform, was added 5-tert-butylisoxazole-3-isocyanate (0.431 g, 2.6 mmol) and the mixture was heated to reflux for approximately 3 hours. The crude product was purified by Flash chromatography with silica gel using a 5-20% methanol/DCM with 0.5% triethylamine. $^1$H NMR (DMSO-d$_6$) 9.8 (s, 1H); 9.5 (s, 1H); 8.8 (s, 1H); 8.0 (d, 1H); 7.7 (m, 3H); 7.6 (d, 2H); 7.2 (d, 1H); 6.5 (s, 1H); 4.3 (m, 3H); 3.7 (m, 5H); 3.4 (m, 4H); 3.2 (m, 1H); 3.0 (s, 3H); 2.3 (m, 2H); 1.3 (s, 9H).

E. The following compounds were made in the manner described in Steps A-D but using the appropriate secondary amine in Step B.

1-(5-tert-Butyl-isoxazol-3-yl)-3-{4-[7-(3-thiomorpholin-4-yl-propoxy)-benzo[d]imidazo[2,1-b]thiazol-2-yl]-phenyl}-urea; $^1$H NMR (DMSO-d$_6$) 11 (s, 1H); 9.7 (s, 1H); 9.3 (s, 1H); 8.7 (s, 1H); 7.9 (d, 2H); 7.8 (m, 3H); 7.5 (m, 2H); 7.2 (d, 1H); 6.5 (s, 1H); [Compound B8] and 1-(5-tert-Butyl-isoxazol-3-yl)-3-(4-{7-[3-(4-methyl-piperazin-1-yl)-propoxy]-benzo[d]imidazo[2,1-b]thiazol-2-yl}-phenyl)-urea; $^1$H NMR (methanol-d$_4$) 8 (s, 1H); 7.7 (d, 2H); 7.6 (d, 1H); 7.5 (d, 2H); 6.9 (m, 1H); 6.4 (s, 1H); 3.9 (m, 1H); 3.3 (s, 3H); 2.5 (m, 8H); 2.3 (s, 3H); 1.8 (m, 2H); 1.3 (s, 9H); [Compound B9]

Example 8

Preparation of Ethyl 2-{2-[4-({[(5-tert-Butylisoxazol-3-yl)amino]carbonyl}amino)phenyl]imidazo[2,1-b][1,3]benzothiazol-7-yl}acetate [Compound C1]

A. To prepare the intermediate (2-amino-1,3-benzothiazol-6-yl)acetic acid,
a solution of bromine (2.3 mL) in 10 mL acetic acid was added dropwise over 30 min to a solution of (4-aminophenyl) acetic acid (7.00 g, 46.3 mmol) and NH$_4$SCN (7.00 g, 92 mmol) in 90% acetic acid (100 mL) at 0° C. After addition was completed, the cold bath was removed and the reaction mixture was stirred at room temperature for 4 hours. Water (300 mL) was added to the mixture followed by sodium carbonate until pH 5. The resulting yellow precipitate was collected by filtration, washed with water and ether, and dried under vacuum with P$_2$O$_5$ to give the product as yellow solid. Yield: 7.89 g (82%)

$^1$H NMR (DMSO-d$_6$) δ 7.51 (s, 1H), 7.40 (br, 2H), 7.24 (d, 1H), 7.07 (d, 1H), 3.50 (s, 2H); LC-MS: ESI 209 (M+H)$^+$.

B. To prepare the intermediate methyl (2-amino-benzothiazol-6-yl)acetate, 2 mL concentrated H$_2$SO$_4$ was added dropwise to a solution of (2-amino-1,3-benzothiazol-6-yl) acetic acid (7.89 g, 37.9 mmol) in 200 mL methanol and the reaction mixture was heated at 50° C. for 90 minutes. After evaporation of most of the methanol, dichloromethane (150 mL) was added and the mixture was neutralized with saturated NaHCO$_3$ solution. The aqueous phase was extracted with dichloromethane. The organic extracts were combined, dried over MgSO$_4$, and concentrated to give the product as a yellow solid (6.51 g, 77%). $^1$H NMR (DMSO-d$_6$) δ 7.54 (s, 1H), 7.44 (br, 2H), 7.27 (d, 1H), 7.09 (d, 1H), 3.66 (s, 2H), 3.61 (s, 3H); LC-MS: ESI 223 (M+H)$^+$.

C. To prepare the intermediate methyl[2-(4-nitrophenyl) imidazo[2,1-b][1,3]benzothiazol-7-yl]acetate, a mixture of methyl (2-amino-1,3-benzothiazol-6-yl)acetate (6.26 g, 28 mmol) and 2-bromo-4'-nitroacetophenone (8.786 g, 36 mmol) in absolute ethanol (80 mL) was heated at 90° C. for 12 hours. A yellow solid was formed, collected by filtration, washed with ethanol, and dried under vacuum to give the product as yellow solid (5.01 g, 48%). $^1$H NMR (DMSO-d$_6$) δ 9.07 (s, 1H), 8.32 (d, 2H), 8.12 (d, 2H), 7.97 (s, 1H and d, 2H), 7.50 (d, 1H), 3.84 (s, 2H), 3.65 (s, 3H); LC-MS: ESI 368 (M+H)$^+$.

D. To make ethyl[2-(4-aminophenyl)imidazo[2,1-b][1,3]benzothiazol-7-yl]acetate intermediate: a mixture of methyl [2-(4-nitrophenyl)imidazo[2,1-b][1,3]benzothiazol-7-yl]acetate (5.00 g, 13.6 mmol) and tin(II) chloride dihydrate (15.795 g, 70 mmol) in ethanol (150 mL) was heated at 95 for 8 hours. Additional tin(II) chloride dihydrate was added and stirred at 95 over night. The reaction was quenched with water (200 mL) and dichloromethane (500 mL), and the pH was adjusted to about 7 with 10% sodium hydroxide. The aqueous phase was extracted with dichloromethane, the combined organic extracts were dried over MgSO$_4$ and concentrated. The residue was taken up in dichloromethane and ether and allowed to stand overnight to form a yellow solid which was filtered off and dried to give the product as yellow solid (2.55 g, 53%). $^1$H NMR (DMSO-d$_6$) δ 8.4 (s, 1H), 7.87 (m, 2H), 7.49 (d, 2H), 7.40 (d, 1H), 6.60 (d, 2H), 5.19 (s, 2H), 4.07 (q, 2H), 3.79 (s, 2H), 1.18 (t, 3H); LC-MS: ESI 352 (M+H)$^+$.

E. To prepare the title compound, a mixture of ethyl[2-(4-aminophenyl)imidazo[2,1-b][1,3]benzothiazol-7-yl]acetate (2.50 g, 7.1 mmol) and 5-tert-butyl-3-isocyanatoisoxazole (1.412 g, 8.5 mmol) in toluene (60 mL) was heated at 110° C. over night. The precipitate was collected by filtration, washed with ether, and dried under vacuum to give the product as white solid (3.592 g, 98% NMR (DMSO-d$_6$) δ 9.54 (s, 1H), 8.89 (s, 1H), 8.67 (s, 1H), 7.93 (s, 1H), 7.90 (d, 1H), 7.80 (d, 2H), 7.53 (d, 2H), 7.47 (d, 1H), 6.53 (s, 1H), 4.11 (q, 2H), 3.81 (s, 2H), 1.31 (s, 9H), 1.20 (t, 3H); LC-MS: ESI 518 (M+H)$^+$.

Example 9

Preparation of 2-{2-[4-({[(5-tert-Butylisoxazol-3-yl) amino]carbonyl}amino)phenyl]imidazo[2,1-b][1,3]benzothiazol-7-yl}acetic acid [Compound C2]

A. To a suspension of ethyl 2-{2-[4-({[(5-tert-butylisoxazol-3-yl)amino]carbonyl}amino)phenyl]imidazo[2,1-b][1,3]benzothiazol-7-yl}acetate from Example 8, (2.00 g, 3.86 mmol) in 30 mL THF was added lithium hydroxide monohydrate (0.966 g, 23 mmol) and 15 mL water. The reaction mixture was stirred at room temperature over night. After evaporation of THF, the aqueous mixture was acidified with 10% HCl solution to pH 6. A white solid was formed, collected by filtration, washed with water and ether, and dried under vacuum with $P_2O_5$ to give the product as white solid (1.815 g, 96%). $^1$H NMR (DMSO-$d_6$) δ 12.4 (br, 1H), 9.58 (s, 1H), 8.94 (s, 1H), 8.68 (s, 1H), 7.92 (s, 1H), 7.90 (d, 1H), 7.80 (d, 2H), 7.54 (d, 2H), 7.45 (d, 1H), 6.53 (s, 1H), 3.72 (s, 2H), 1.30 (s, 9H); LC-MS: ESI 490 (M+H)$^+$.

B. To prepare its sodium salt: to a solution of 2-{2-[4-({[(5-tert-butylisoxazole-3-yl)amino]carbonyl}amino)phenyl]imidazo[2,1-b][1,3]benzothiazole-7-yl}acetic acid (0.13 g, 0.27 mmol) in MeOH (20 mL) and water (1 mL) was added sodium methoxide (0.017 g, 0.031 mmol). After MeOH was evaporated, to the residue was added EtOH, and then was evaporated for three times to give the product as a white solid (0.112 g). $^1$H NMR (DMSO-$d_6$) δ 11.1 (br, 1H), 10.25 (br, 1H), 8.45 (s, 1H), 7.74 (m, 2H), 7.44 (d, 3H), 7.1 (d, 2H), 6.44 (s, 1H), 3.34 (s, 2H), 1.23 (s, 9H).

Example 10

Preparation of Ethyl 3-{2-[4-({[(5-tert-Butylisoxazol-3-yl)amino]carbonyl}amino)phenyl]imidazo[2,1-b][1,3]benzothiazol-7-yl}propanoate [Compound C3]

A. To prepare the intermediate 3-(2-amino-1,3-benzothiazol-6-yl)propanoic acid, a solution of bromine (3 mL) in 10 mL acetic acid was added dropwise over 30 min to a solution of 3-(4-aminophenyl)propanoic acid (10.00 g, 60.5 mmol) and NH$_4$SCN (9.21 g, 121 mmol) in 120 mL acetic acid at 0° C. After the addition was completed the cold bath was removed and the reaction mixture was stirred at room temperature for 4 hours. Water (300 mL) was added to the mixture followed by sodium carbonate until pH 5. The resulting yellow precipitate was collected by filtration, washed with water and ether, and dried under vacuum with $P_2O_5$. Yield: 13.425 g (99%)$^1$H NMR (DMSO-$d_6$) δ 12.11 (br, 1H), 7.49 (s, 1H), 7.37 (br, 2H), 7.23 (d, 1H), 7.06 (d, 1H), 2.82 (t, 2H), 2.5 (t, 2H, overlap with solvent); LC-MS: ESI 223 (M+H)$^+$.

B. In preparing the intermediate methyl 3-(2-amino-1,3-benzothiazol-6-yl)propanoate), 2 mL concentrated $H_2SO_4$ was added dropwise to a solution of 3-(2-amino-1,3-benzothiazol-6-yl)propanoic acid from Step A (13.42 g, 60.4 mmol) in methanol (150 mL) and the reaction mixture was stirred at room temperature over night. After evaporation of most of the solvent, dichloromethane (200 mL) was added and the mixture was neutralized with saturated NaHCO$_3$ solution. The aqueous phase was extracted with dichloromethane, the combined organic extracts dried over MgSO$_4$ and concentrated to give the product as yellow solid (9.762 g, 68%). $^1$H NMR (CDCl$_3$) δ 7.37 (s, 1H and d, 1H), 7.15 (d, 1H), 5.30 (br, 2H), 3.68 (s, 3H), 3.00 (t, 2H), 2.17 (t, 2H); LC-MS: ESI 237 (M+H)$^+$.

C. To prepare the intermediate methyl 3-[2-(4-nitrophenyl)imidazo[2,1-b][1,3]benzothiazol-7-yl]propanoate: A mixture of methyl 3-(2-amino-1,3-benzothiazol-6-yl)propanoate (9.76 g, 41.3 mmol) from Step A and 2-bromo-4'-nitroacetophenone (13.178 g, 54 mmol) in absolute ethanol (150 mL) was heated at 90° C. for 12 hours. A yellow solid was formed, collected by filtration, washed with ethanol, and dried under vacuum to give the product as yellow solid (6.015 g, 38%). $^1$H NMR (DMSO-$d_6$) δ 9.05 (s, 1H), 8.30 (d, 2H), 8.11 (d, 2H), 7.92 (s, 1H), 7.90 (d, 1H), 7.45 (d, 1H), 3.60 (s, 3H), 3.09 (t, 2H), 2.68 (t, 2H); LC-MS: ESI 382 (M+H)$^+$.

D. To prepare the intermediate ethyl 3-[2-(4-aminophenyl)imidazo[2,1-b][1,3]benzothiazol-7-yl]propanoate: A mixture of methyl 3-[2-(4-nitrophenyl)imidazo[2,1-b][1,3]benzothiazol-7-yl]propanoate (6.01 g, 15.8 mmol) from Step B and tin(II) chloride dehydrate (18.05 g, 80 mmol) in ethanol (200 mL) was heated at 90° C. for 12 hours. The reaction was quenched with 400 mL water and 400 mL dichloromethane and the pH was adjusted to about 7 with sodium carbonate. The aqueous phase was extracted with dichloromethane, the combined organic extracts were dried over MgSO$_4$ and concentrated. The crude product was purified by Flash chromatography with silica gel using a 0-100% hexane/ethyl acetate gradient to give the product as a yellow solid (3.824 g, 66%). $^1$H NMR (CDCl$_3$) δ 7.86 (s, 1H), 7.61 (d, 2H), 7.53 (s, 1H), 7.48 (d, 1H), 7.29 (d, 1H), 6.75 (d, 2H), 4.14 (q, 2H), 3.73 (br, 2H), 3.06 (t, 2H), 2.67 (t, 2H), 1.23 (t, 3H); LC-MS: ESI 366 (M+H)$^+$.

E. A mixture of ethyl 3-[2-(4-aminophenyl)imidazo[2,1-b][1,3]benzothiazol-7-yl]propanoate (3.80 g, 10.4 mmol) from Step C and 5-tert-butyl-3-isocyanatoisoxazole (2.08 g, 12.5 mmol) in toluene (80 mL) was heated at 110° C. over night. A precipitate was formed, collected by filtration, washed with ether, and dried under high vacuum to give the title compound as a white solid (5.056 g, 91%). $^1$H NMR (DMSO-$d_6$) δ 9.62 (s, 1H), 9.08 (s, 1H), 8.70 (s, 1H), 7.91 (s, 1H), 7.89 (d, 1H), 7.79 (d, 2H), 7.54 (d, 2H), 7.46 (d, 1H), 6.53 (s, 1H), 4.06 (q, 2H), 2.98 (t, 2H), 2.70 (t, 2H), 1.30 (s, 9H), 1.15 (t, 3H); LC-MS: ESI 532 (M+H)$^+$.

F. Preparation of 3-{2-[4-({[(5-tert-butylisoxazol-3-yl)amino]carbonyl}amino)phenyl]imidazo[2,1-b][1,3]benzothiazol-7-yl}propanoic acid: To a suspension of ethyl 3-{2-[4-({[(5-tert-butylisoxazol-3-yl)amino]carbonyl}amino)phenyl]imidazo[2,1-b][1,3]benzothiazol-7-yl}propanoate from Step E (3.00 g, 5.6 mmol) in THF (30 mL) was added lithium hydroxide monohydrate (1.428 g, 34 mmol) and 20 mL water. The reaction mixture was stirred at room temperature overnight. After evaporation of the organic solvent, the aqueous phase was acidified with 10% HCl solution to pH 6. A white solid was formed, collected by filtration, washed with water and ether, and dried under vacuum with $P_2O_5$ to give the product as a white solid (2.791 g, 99%). $^1$H NMR (DMSO-$d_6$) δ 9.66 (s, 1H), 9.21 (s, 1H), 8.68 (s, 1H), 7.90 (s, 1H), 7.88 (d, 1H), 7.79 (d, 2H), 7.54 (d, 2H), 7.46 (d, 1H), 6.53 (s, 1H), 2.95 (t, 2H), 2.62 (t, 2H), 1.31 (s, 9H); LC-MS: ESI 503 (M+H)$^+$. [Compound C4]

G. The corresponding sodium salt of the product in Step F was prepared in the manner described in Example 9B; $^1$H NMR (DMSO-$d_6$) δ 12.2 (br, 1H), 11.2 (br, 1H), 8.58 (s, 1H), 7.9 (d, 1H), 7.81 (s, 1H), 7.5 (d, 1H), 7.46 (d, 2H), 7.21 (d, 2H), 6.49 (s, 1H), 2.9 (t, 2H), 2.45 (t, 2H), 1.29 (s, 9H).

Example 11

Preparation of 2-{4-[3-(5-tert-Butyl-isoxazol-3-yl)-ureido]-phenyl}-imidazo[2,1-b][1,3]benzothiazole-7-carboxylic acid ethyl ester [Compound C26]

A, To prepare the intermediate 2-(4-nitro-phenyl)-benzo[d]imidazo[2,1-b]thiazole-7-carboxylic acid ethyl ester, 2-aminobenzothiazole-6-carboxylic acid ethyl ester and 2-bromo-4'-nitroacetophenone were combined in 2-methoxy ethanol and stirred at 40° C. for 24 hours. Formation of the intermediate was confirmed by LCMS. The reaction was heated further at 140° C. for 18 hours, filtered, washed with ethanol and dried under high vacuum to produce a yellow solid.

B. To prepare the intermediate 2-(4-aminophenyl)-benzo[d]imidazo[2,1-b]thiazole-7-carboxylic acid ethyl ester, SnCl$_2$.H$_2$O (6.770 g, 30 mmol) was added to the intermediate from Step A (2.204 g, 6 mmol) in ethanol (40 mL), and heated to reflux for 20 hours. The reaction was quenched with water, neutralized with saturated NaHCO$_3$ and extracted with CH$_2$Cl$_3$ with some methanol. The extract was dried over MgSO$_4$ and concentrated to give a yellow solid (1.518 g, 75%).

C. To prepare the title compound, a mixture of the intermediate from Step B (1.51 g, 4.48 mmol) and 5-tert-butyl-3-isocyanatoisoxazole (997 mg, 6 mmol) in toluene (40 mL) was heated at 100° C. overnight. The formation of the product was confirmed by LC-MS. The precipitate was collected by filtration and washed with CH$_2$Cl$_2$ and dried under high vacuum to produce a gray solid (2.245 g, 99.5%). $^1$H NMR (DMSO-d$_6$) δ 9.5 (br, 2H), 8.76 (s, 1H), 8.70 (d, 1H), 8.1 (dd, 1H), 8.08 (d, 1H), 7.80 (d, 2H), 7.55 (d, 2H), 6.53 (s, 1H), 4.37 (q, 2H), 1.36 (t, 3H), 1.30 (s, 9H); LC-MS: ESI 504 (M+H)$^+$.

D. The intermediate from Step C underwent base hydrolysis as described in Example 10F to produce the carboxylic acid.

E. Sodium 2-{4-[3-(5-tert-butyl-isoxazol-3-yl)-ureido]-phenyl}-benzo[d]imidazo[2,1-b]thiazole-7-carboxylate was prepared in the manner described in Example 9B, using the compound from Step D; $^1$H NMR (DMSO-d$_6$) δ 8.67 (s, 1H), 8.47 (d, 1H), 8.10 (dd, 1H), 8.87 (d, 1H), 7.78 (d, 2H), 7.67 (d, 2H), 6.55 (s, 1H), 1.31 (s, 9H); LC-MS: ESI 476 (M+H)$^+$. [Compound C27]

Example 12

Preparation of N-(5-tert-Butyl-isoxazol-3-yl)-N'-(4-{7-[3-(4-ethyl-piperazin-1-yl)-3-oxo-propyl]imidazo[2,1-b][1,3]benzothiazol-2-yl}phenyl)urea [Compound C5]

A. To a solution of 3-{2-[4-({[(5-tert-butylisoxazol-3-yl)amino]carbonyl}amino)phenyl]imidazo[2,1-b][1,3]benzothiazol-7-yl}propanoic acid from Example 10F (0.310 g, 0.61 mmol) in DMF (8 mL) at room temperature was added N-(3-dimethylaminopropyl)-N'-ethylcarbodiimide hydrochloride (0.173 g, 0.9 mmol) and 1-hydroxybenzotriazole hydrate (0.122 g, 0.9 mmol). After stirring 1 hour, 1-ethylpiperazine (0.5 mL) was added and the mixture was stirred at room temperature over night. The reaction was quenched with 60 mL water, the precipitate was collected by filtration, washed with water and ether, and dried under vacuum with P$_2$O$_5$ to give the product as a white solid (0.174 g, 48%. $^1$H NMR (CDCl$_3$) δ 9.54 (s, 1H), 8.88 (s, 1H), 8.65 (s, 1H), 7.88 (s, 1H), 7.85 (d, 1H), 7.79 (d, 2H), 7.52 (d, 2H), 7.45 (d, 1H), 6.50 (s, 1H), 3.49 (m, 6H, overlapping with solvent), 2.89 (m, 2H), 2.71 (m, 2H), 2.25 (m, 4H), 1.30 (s, 9H), 0.97 (t, 3H); LC-MS: ESI 600 (M+H)$^+$.

B. To prepare its hydrochloride salt, the product in Step A was treated in the manner described in Example 3F. $^1$H NMR (DMSO-d$_6$) δ 10.85 (br, 1H), 9.69 (br, 1H), 9.41 (br, 1H), 8.71 (s, 1H), 7.88 (d and s, 2H), 7.73 (d, 2H), 7.51 (d, 2H), 7.45 (d, 1H), 6.47 (s, 1H), 4.41 (m, 2H), 4.05 (m, 1H), 3.35 (m, 3H), 2.69-3.10 (m, 8H), 1.24 (s, 9H), 1.17 (t, 3H).

C. The following compounds were made in a manner similar to Step A, but replacing 1-ethylpiperazine with other amines such as piperidine, morpholine and N,N-diethylamine. The corresponding hydrochloride salt was prepared in the same manner as described in step B.

N-(5-tert-butyl-isoxazol-3-yl)-N'-{4-[7-(3-oxo-3-piperidin-1-yl-propyl)imidazo[2,1-b][1,3]benzothiazol-2-yl]phenyl}urea; (0.381 g, 84%). $^1$H NMR (DMSO-d$_6$) δ 9.65 (s, 1H), 9.00 (s, 1H), 8.65 (s, 1H), 7.90 (s, 1H), 7.86 (d, 1H), 7.78 (d, 2H), 7.54 (d, 2H), 7.46 (d, 1H), 6.53 (s, 1H), 3.41 (m, 4H), 2.93 (t, 2H), 2.68 (t, 2H), 1.54 (m, 2H), 1.42 (m, 4H), 1.30 (s, 9H); LC-MS: ESI 571 (M+H)$^+$; [Compound C6]

N-(5-tert-butyl-isoxazol-3-yl)-N'-{4-[7-(3-morpholino-4-yl-3-oxo-propyl)imidazo[2,1-b][1,3]benzothiazol-2-yl]phenyl}urea; $^1$H NMR (DMSO-d$_6$) δ 9.56 (s, 1H), 8.90 (s, 1H), 8.66 (s, 1H), 7.89 (s, 1H), 7.85 (d, 1H), 7.79 (d, 2H), 7.52 (d, 2H), 7.45 (d, 1H), 6.52 (s, 1H), 3.52 (m, 4H), 3.50 (m, 4H), 2.94 (t, 2H), 2.70 (t, 2H), 1.30 (s, 9H); LC-MS: ESI 573 (M+H)$^+$; [Compound C7]

3-(2-{4-[3-(5-tert-butyl-isoxazol-3-yl)-ureido]-phenyl}-benzo[d]imidazo[2,1-b]thiazol-7-yl)-N,N-diethyl-propionamide; $^1$H NMR (DMSO-d$_6$) δ 9.7 (br, 1H), 9.23 (br, 1H), 8.65 (s, 1H), 7.87 (d and s, 2H), 7.76 (d, 2H), 7.53 (d, 2H), 7.45 (d, 1H), 6.52 (s, 1H), 3.25 (m, 6H), 2.94 (m, 2H), 2.65 (m, 2H), 1.30 (s, 9H), 1.02 (m, 6H); [Compound C8]

3-(2-{4-[3-(5-tert-butyl-isoxazol-3-yl)-ureido]-phenyl}-benzo[d]imidazo[2,1-b]thiazol-7-yl)-N-(2-morpholin-4-yl-ethyl)-propionamide hydrochloride; $^1$H NMR (DMSO-d$_6$) δ 10.6 (br, 1H), 9.61 (br, 1H), 9.17 (br, 1H), 8.64 (s, 1H), 8.20 (t, 1H), 7.82 (d and s, 2H), 7.71 (d, 2H), 7.48 (d, 2H), 7.36 (d, 1H), 6.46 (s, 1H), 3.86 (m, 2H), 3.71 (t, 2H), 3.77 (m, 4H), 2.88-3.07 (m, 6H), 2.45 (m, 2H), 1.23 (s, 9H); [Compound C9]

3-(2-{4-[3-(5-tert-butyl-isoxazol-3-yl)-ureido]-phenyl}-benzo[d]imidazo[2,1-b]thiazol-7-yl)-N-(2-piperidin-1-yl-ethyl)-propionamide hydrochloride; $^1$H NMR (DMSO-d$_6$) δ 10.04 (br, 1H), 9.70 (br, 1H), 9.36 (br, 1H), 8.72 (s, 1H), 8.29 (t, 1H), 7.88 (d and s, 2H), 7.76 (d, 2H), 7.53 (d, 2H), 7.42 (d, 1H), 6.50 (s, 1H), 3.39 (m, 4H), 3.95 (m, 4H), 2.77 (m, 2H), 2.47 (m, 2H), 1.69 (m, 5H), 1.27 (s and m, 10H); [Compound C10]

3-(2-{4-[3-(5-tert-butyl-isoxazol-3-yl)-ureido]-phenyl}-benzo[d]imidazo[2,1-b]thiazol-7-yl)-N-(2-pyrrolidin-1-yl-ethyl)-propionamide hydrochloride; $^1$H NMR (DMSO-d$_6$) δ 10.4 (br, 1H), 9.71 (br, 1H), 9.34 (br, 1H), 8.73 (s, 1H), 8.26 (t, 1H), 7.90 (d and s, 2H), 7.78 (d, 2H), 7.55 (d, 2H), 7.45 (d, 1H), 6.53 (s, 1H), 3.52 (m, 2H), 3.40 (m, 2H), 3.15 (m, 2H), 2.8-3.00 (m, 4H), 2.5 (2H), 1.93 (m, 2H), 1.85 (m, 2H), 1.30 (s, 9H); [Compound C11]; and 3-(2-{4-[3-(5-tert-butyl-isoxazol-3-yl)-ureido]-phenyl}-benzo[d]imidazo[2,1-b]thiazol-7-yl)-N-(2-diethylamino-ethyl)-propionamide hydrochloride; $^1$H NMR (DMSO-d$_6$) δ 9.95 (br, 1H), 9.64 (br, 1H), 9.25 (br, 1H), 8.66 (s, 1H), 8.23 (t, 1H), 7.83 (d and s, 2H), 7.72 (d, 2H), 7.48 (d, 2H), 7.38 (d, 1H), 6.46 (s, 1H), 3.34 (m, 2H), 2.88-3.07 (m, 8H), 2.5 (2H), 1.24 (s, 9H), 1.10 (t, 6H) [Compound C12].

D. The following compounds were made in a manner similar to Step A, but replacing the propanoic acid with 3-{2-[4-({[(5-tert-butylisoxazol-3-yl)amino]carbonyl}amino)phenyl]imidazo[2,1-b][1,3]benzothiazol-7-yl}acetic acid from Example 9A and using the appropriately substituted amines. The corresponding hydrochloride salts were prepared in the manner described in Example 3F.

2-(2-{4-[3-(5-tert-butyl-isoxazol-3-yl)-ureido]-phenyl}-benzo[d]imidazo[2,1-b]thiazol-7-yl)-N-(2-morpholin-4-yl-ethyl)-acetamide hydrochloride; $^1$H NMR (DMSO-d$_6$) δ 10.76 (br, 1H), 9.65 (br, 1H), 9.24 (br, 1H), 8.70 (s, 1H), 8.51 (br, 1H), 7.91 (d and s, 2H), 7.76 (d, 2H), 7.50 (m, 3H), 6.50 (s, 1H), 3.90 (m, 2H), 3.76 (t, 2H), 3.59 (s, 2H), 3.40 (m, 4H), 3.14 (m, 2H), 2.99 (m, 2H), 1.27 (s, 9H); [Compound C13]

2-(2-{4-[3-(5-tert-butyl-isoxazol-3-yl)-ureido]-phenyl}-benzo[d]imidazo[2,1-b]thiazol-7-yl)-N-(2-piperidin-1-yl-ethyl)-acetamide hydrochloride; $^1$H NMR (DMSO-d$_6$) δ 9.8 (br, 1H), 9.60 (br, 1H), 9.15 (br, 1H), 8.64 (s, 1H), 8.47 (t, 1H), 7.86 (d and s, 2H), 7.72 (d, 2H), 7.48 (d, 2H), 7.42 (d, 1H), 6.46 (s, 1H), 3.54 (s, 2H), 3.37 (m, 4H), 3.05 (m, 2H), 2.81 (m, 2H), 1.64 (m, 6H), 1.24 (s, 9H); [Compound C14]

2-(2-{4-[3-(5-tert-butyl-isoxazol-3-yl)-ureido]-phenyl}-benzo[d]imidazo[2,1-b]thiazol-7-yl)-N-(2-pyrrolidin-1-yl-ethyl)-acetamide hydrochloride; $^1$H NMR (DMSO-d$_6$) δ 9.95 (br, 1H), 9.70 (br, 1H), 9.26 (br, 1H), 8.67 (s, 1H), 8.35 (t, 1H), 7.90 (d and s, 2H), 7.78 (d, 2H), 7.54 (d, 2H), 7.46 (d, 1H), 6.53 (s, 1H), 3.59 (s, 2H), 3.34 (2H), 2.86 (m, 6H), 1.80 (m, 4H), 1.30 (s, 9H); [Compound C15]

2-(2-{4-[3-(5-tert-butyl-isoxazol-3-yl)-ureido]-phenyl}-benzo[d]imidazo[2,1-b]thiazol-7-yl)-N-(2-diethylamino-ethyl)-acetamide hydrochloride; $^1$H NMR (DMSO-d$_6$) δ 9.85 (br, 1H), 9.65 (br, 1H), 9.18 (br, 1H), 8.70 (s, 1H), 8.49 (t, 1H), 7.93 (d and s, 2H), 7.79 (d, 2H), 7.54 (d, 2H), 7.48 (d, 1H), 6.53 (s, 1H), 3.61 (s, 2H), 3.43 (m, 2H), 3.14 (m, 6H), 1.30 (s, 9H), 1.18 (t, 6H); [Compound C16], and 1-(5-tert-butyl-isoxazol-3-yl)-3-(4-{7-[2-(4-ethyl-piperazin-1-yl)-2-oxo-ethyl]benzo[d]imidazo[2,1-b]thiazol-2-yl}-phenyl)-urea hydrochloride; $^1$H NMR (DMSO-d$_6$) δ 10.9 (br, 1H), 9.78 (br, 1H), 9.40 (br, 1H), 8.81 (s, 1H), 8.01 (d, 1H), 7.95 (s, 1H), 7.86 (d, 2H), 7.63 (d, 2H), 7.50 (d, 1H), 6.60 (s, 1H), 4.55 (d, 1H), 4.3 (d, 1H), 4.00 (s, 2H), 3.57 (m, 3H), 3.21 (m, 3H), 3.00 (m, 2H), 1.37 (s, 9H), 1.35 (t, 3H); [Compound C17]; and 1-(5-tert-butyl-isoxazol-3-yl)-3-{4-[7-(2-morpholin-4-yl-2-oxo-ethyl)-imidazo[2,1-b][1,3]benzothiazol-2yl]-phenyl}-urea; $^1$H NMR (DMSO-d$_6$) δ 9.55 (s, 1H), 8.88 (s, 1H), 8.66 (s, 1H), 7.88 (d, 1H), 7.85 (s, 1H), 7.78 (d, 2H), 7.53 (d, 2H), 7.41 (dd, 1H), 6.53 (s, 1H), 3.86 (s, 2H), 3.55 (m, 6H), 3.47 (m, 2H), 1.30 (s, 9H) [Compound C18].

E. The following compounds were made in a manner similar to Step A, but replacing the propanoic acid with 2-{4-[3-(5-tert-butyl-isoxazol-3-yl)-ureido]-phenyl}-benzo[d]imidazo[2,1-b]thiazole-7-carboxylic acid from Example 11D and using the appropriately substituted amines. The corresponding hydrochloride salts were prepared in the manner described in Example 3F.

2-{4-[3-(5-tert-butyl-isoxazol-3-yl)-ureido]-phenyl}imidazo[2,1-b][1,3]benzothiazole-7-carboxylic acid (2-morpholin-4-yl-ethyl)-amide hydrochloride; $^1$H NMR (DMSO-d$_6$) δ 10.5 (br, 1H), 9.65 (s, 1H), 9.17 (s, 1H), 9.02 (t, 1H), 8.76 (s, 1H), 8.59 (s, 1H), 8.09 (m, 2H), 7.79 (d, 2H), 7.56 (d, 2H), 6.53 (s, 1H), 4.00 (m, 2H), 3.82 (m, 4H), 3.57 (m, 2H), 3.35 (m, 2H), 3.17 (m, 2H), 1.31 (s, 9H); LC-MS: ESI 588 (M+H)$^+$; [Compound C19];

2-{4-[3-(5-tert-butyl-isoxazol-3-yl)-ureido]-phenyl}-imidazo[2,1-b][1,3]benzothiazole-7-carboxylic Acid (2-Piperidin-1-yl-ethyl)-amide hydrochloride $^1$H NMR (DMSO-d$_6$) δ 9.8 (br, 1H), 9.66 (s, 1H), 9.20 (s, 1H), 9.03 (t, 1H), 8.76 (s, 1H), 8.59 (d, 1H), 8.09 (m, 2H), 7.79 (d, 2H), 7.56 (d, 2H), 6.53 (s, 1H), 3.72 (m, 2H), 3.56 (m, 2H), 3.26 (m, 2H), 2.96 (m, 2H), 1.80 (m, 5H), 1.4 (m, 1H), 1.30 (s, 9H); LC-MS: ESI 586 (M+H)$^+$; [Compound C20];

2-{4-[3-(5-tert-butyl-isoxazol-3-yl)-ureido]-phenyl}-imidazo[2,1-b][1,3]benzothiazole-7-carboxylic Acid (2-Pyrrolidin-1-yl-ethyl)-amide hydrochloride, $^1$H NMR (DMSO-d$_6$) δ 10.2 (br, 1H), 9.68 (s, 1H), 9.24 (s, 1H), 8.99 (t, 1H), 8.77 (s, 1H), 8.60 (d, 1H), 8.09 (m, 2H), 7.79 (d, 2H), 7.56 (d, 2H), 6.53 (s, 1H), 3.67 (m, 4H), 3.37 (m, 2H), 3.06 (m, 2H), 2.00 (m, 4H), 1.31 (s, 9H); LC-MS: ESI 572 (M+H)$^+$; [Compound C21];

2-{4-[3-(5-tert-butyl-isoxazol-3-yl)-ureido]-phenyl}-imidazo[2,1-b][1,3]benzothiazole-7-carboxylic acid (2-diethylamino-ethyl)-amide hydrochloride; $^1$H NMR (DMSO-d$_6$) δ 9.8 (br, 1H), 9.62 (s, 1H), 9.13 (s, 1H), 8.98 (t, 1H), 8.74 (s, 1H), 8.55 (s, 1H), 8.07 (m, 2H), 7.77 (d, 2H), 7.53 (d, 2H), 6.51 (s, 1H), 3.66 (m, 2H), 3.22 (m, 6H), 1.28 (s, 9H), 1.22 (t, 6H); LC-MS: ESI 574 (M+H)$^+$; [Compound C22];

1-(5-tert-butyl-isoxazol-3-yl)-3-{4-[7-(4-ethyl-piperazine-1-carbonyl)-imidazo[2,1-b][1,3]benzothiazol-2-yl]-phenyl}-urea hydrochloride; $^1$H NMR (DMSO-d$_6$) δ 10.7 (br, 1H), 9.73 (s, 1H), 9.27 (s, 1H), 8.84 (s, 1H), 8.27 (s, 1H), 8.12 (d, 1H), 7.86 (d, 2H), 7.76 (d, 1H), 7.64 (d, 2H), 6.60 (s, 1H), 3.54 (m, 4H), 3.16 (m, 6H), 1.37 (s, 9H), 1.33 (l, 3H); LC-MS: ESI 572 (M+H)$^+$; [Compound C23];

1-(5-tert-butyl-isoxazol-3-yl)-3-{4-[7-(piperazine-1-carbonyl)-imidazo[2,1-b][1,3]benzothiazol-2-yl]-phenyl}-urea hydrochloride, $^1$H NMR (DMSO-d$_6$) δ 9.63 (s, 1H), 9.10 (s, 1H), 9.06 (br, 2H), 8.76 (s, 1H), 8.19 (s, 1H), 8.04 (d, 1H), 7.80 (d, 2H), 7.69 (d, 1H), 7.55 (d, 2H), 6.52 (s, 1H), 3.73 (m, 4H), 3.21 (m, 4H), 1.30 (s, 9H); LC-MS: ESI 544 (M+H)$^+$, [Compound C24]; and 1-(5-tert-butyl-isoxazol-3-yl)-3-{4-[7-(4-methyl-piperazine-1-carbonyl)-imidazo[2,1-b][1,3]benzothiazol-2-yl]-phenyl}-urea hydrochloride, $^1$H NMR (DMSO-d$_6$) δ 10.8 (br, 1H), 9.63 (s, 1H), 9.22 (s, 1H), 8.72 (s, 1H), 8.13 (s, 1H), 8.00 (d, 1H), 7.72 (d, 2H), 7.62 (d, 1H), 7.49 (d, 2H), 6.46 (s, 1H), 3.33 (m, 4H), 3.06 (m, 4H), 2.74 (s, 3H), 1.24 (s, 9H); LC-MS: ESI 558 (M+H)$^+$ [Compound C25].

Example 13

Preparation of N-(5-tert-Butyl-isoxazol-3-yl)-N'-(4-{7-[3-(4-ethyl-piperazin-1-yl)propyl]imidazo[2,1-b][1,3]benzothiazol-2-yl}phenyl)urea hydrochloride [Compound D1]

To a suspension of N-(5-tert-butyl-isoxazol-3-yl)-N'-(4-{7-[3-(4-ethyl-piperazin-1-yl)-3-oxo-propyl]imidazo[2,1-b][1,3]benzothiazol-2-yl}phenyl)urea from Example 12A (0.17 g, 0.28 mmol) in THF (10 mL) at room temperature was added 2.0 M solution of BH$_3$/Me$_2$S in THF (1 mL). The mixture was heated to reflux for 4 hours. The reaction was quenched by dropwise addition of 10% HCl solution and stirred at room temperature for 15 min. The mixture was basified with saturated NaHCO$_3$ solution and was extracted with dichloromethane. The combined organic extracts were dried over MgSO$_4$ and concentrated. The crude product was purified by Flash chromatography with silica gel using a 30-100% hexane/ethyl acetate gradient followed by a 0-20% methanol/ethyl acetate gradient. The appropriate fractions were collected, combined, and concentrated to give free base, N-(5-tert-butyl-isoxazol-3-yl)-AP-(4-{7-[3-(4-ethyl-piperazin-1-yl)propyl]imidazo[2,1-b][1,3]benzothiazol-2-yl}phenyl)urea. The free base was dissolved in dichloromethane (about 1 mL) and methanol (a few drops). To this solution was added dropwise a 1.0 M solution of HCl/ether (1.3 equivalents) and a precipitate was formed. After evaporation of the solvents, the residue was taken up in ether, filtered, and washed with ether to give the product as a white solid (0.011 g, 6%). $^1$H NMR (DMSO-d$_6$) δ 9.6 (s, 1H), 9.07 (s, 1H), 8.69 (s, 1H), 7.92 (m, 2H), 7.78 (d, 2H), 7.54 (d, 2H), 7.48 (d, 1H), 6.53 (s, 1H), 3.50 (4H, overlapping with solvent), 3.22 (m, 6H), 2.75 (m, 4H), 2.10 (m, 2H), 1.30 (s, 9H), 1.24 (t, 3H); LC-MS: ESI 586 (M+H)$^+$.

Example 14

Preparation of 3-(5-tert-Butyl-isoxazol-3-yl)-1-methyl-1 {4-[7-(3-morpholin-4-yl-propyl)-benzo[d]imidazo[2,1-b]thiazol-2-yl]-phenyl}-urea [Compound D2] and 1-(5-tert-Butyl-isoxazol-3-yl)-3-{4-[7-(3-morpholin-4-yl-propyl)-benzo[d]imidazo[2,1-b]thiazol-2-yl]-phenyl}-urea [Compound D3]

A. To a suspension of N-(5-tert-butyl-isoxazol-3-yl)-N'-{4-[7-(3-morpholino-4-yl-3-oxo-propyl)imidazo[2,1-b][1, 3]benzothiazol-2-yl]phenyl}urea (0.38 g, 0.66 mmol) from Example 120 in THF (10 mL) at room temperature was dropped 2.0 M solution of BH$_3$/Me$_2$S in THF (1.5 mL). The reaction mixture was heated to reflux overnight. To the mixture was added 10% HCl solution to destroy excess BH$_3$/Me$_2$S, quenched with CH$_2$Cl$_2$, neutralized with saturated NaHCO$_3$ solution. The organic layer was dried over MgSO$_4$ and concentrated to give a mixture of two compounds; methyl-{4-[7-(3-morpholin-4-yl-propyl)-benzo[d]imidazo [2,1-b]thiazol-2-yl]-phenyl}-amine and 4-[7-(3-morpholin-4-yl-propyl)-benzo[d]imidazo[2,1-b]thiazol-2-yl]-phenylamine.

B. To the mixture was added toluene and 5-tert-butyl-3-isocyanato-isoxazole (150 mg) and heated at 110° C. overnight. It was quenched with CH$_2$Cl$_2$ and saturated NaHCO$_3$ solution. The organic layer was dried over MgSO$_4$ and concentrated. The crude mixture was separated by Flash chromatography with 0-10% MeOH/CH$_2$Cl$_2$ as eluant to give two compounds: 3-(5-tert-butyl-isoxazol-3-yl)-1-methyl-1-{4-[7-(3-morpholin-4-yl-propyl)-benzo[d]imidazo[2,1-b]thiazol-2-yl]-phenyl}-urea and 1-(5-tert-butyl-isoxazol-3-yl)-3-{4-[7-(3-morpholin-4-yl-propyl)-benzo[d]imidazo[2,1-b]thiazol-2-yl]-phenyl}-urea.

C. The corresponding hydrochloride salts were prepared in a manner described in Example 3F:

3-(5-tert-Butyl-isoxazol-3-yl)-methyl-1-{4-[7-(3-morpholin-4-yl-propyl)-benzo[d]imidazo[2,1-b]thiazol-2-yl]-phenyl}-urea hydrochloride; $^1$H NMR (DMSO-d$_6$) δ 10.7 (br, 1H), 9.31 (br, 1H), 8.81 (s, 1H), 7.94 (m, 2H), 7.88 (d, 2H), 7.49 (m, 1H), 7.38 (d, 2H), 6.50 (s, 1H), 3.94 (m, 2H), 3.76 (m, 6H), 3.30 (s, 3H), 3.09 (m, 4H), 2.77 (m, 4H), 2.08 (m, 2H), 1.28 (s, 9H); and 1-(5-tert-Butyl-isoxazol-3-yl)-3-{4-[7-(3-morpholin-4-yl-propyl)-benzo[d]imidazo[2,1-b]thiazol-2-yl]-phenyl}-urea hydrochloride; $^1$H NMR (DMSO-d$_6$) δ 10.4 (br, 1H), 9.64 (br, 1H), 9.1 (br, 1H), 8.70 (s, 1H), 7.91 (d and s, 2H), 7.79 (d, 2H), 7.54 (d, 2H), 7.45 (d, 1H), 6.53 (s, 1H), 3.93 (m, 2H), 3.73 (m, 6H), 3.09 (m, 4H), 2.78 (m, 4H), 2.1 (m, 2H), 1.30 (s, 9H).

Example 15

Preparation of N-(5-tert-Butyl-isoxazol-3-yl)-N'-{4-[7-(3-piperidin-1-yl-propyl)imidazo[2,1-b][1,3]benzothiazol-2-yl]phenyl}urea hydrochloride [Compound D4]

To a suspension of N-(5-tert-butyl-isoxazol-3-yl)-N'-{4-[7-(3-oxo-3-piperidin-1-yl-propyl)imidazo[2,1-b][1,3]benzothiazol-2-yl]phenyl}urea from Example 12C (0.36 g, 0.63 mmol) in THF (10 mL) at room temperature was added 1.0 M solution of BH$_3$/THF in THF (10 mL). The mixture was heated to reflux over night, but LC-MS showed the reaction was not complete. Therefore, additional 5.0 mL of 1.0 M BH$_3$/THF solution was added and heated to reflux for 8 hours. The reaction was quenched by dropwise addition of 10% HCl solution and stirred at room temperature for 20 min. The mixture was basified with saturated NaHCO$_3$ solution and extracted with dichloromethane. The combined organic extracts were dried over MgSO$_4$ and concentrated. The crude product was purified by Flash chromatography with silica gel using a 0-10% methanol/dichloromethane gradient. The appropriate fractions were collected, combined, and concentrated to give free base, N-(5-tert-butyl-isoxazol-3-yl)-N'-{4-[7-(3-piperidin-1-yl-propyl)imidazo[2,1-b][1,3]benzothiazol-2-yl]phenyl}urea (0.182 g). $^1$H NMR (DMSO-d$_6$) δ 9.54 (s, 1H), 8.88 (s, 1H), 8.67 (s, 1H), 7.90 (s, 1H), 7.88 (d, 1H), 7.79 (d, 2H), 7.53 (d, 2H), 7.45 (d, 1H), 6.53 (s, 1H), 2.75 (m, 8H), 2.05 (m, 2H), 1.67 (m, 2H), 1.47 (m, 4H), 1.30 (s, 9H); $^{13}$C NMR (DMSO-d$_6$) δ 180.55, 158.75, 151.65, 146.97, 146.42, 138.99, 138.38, 130.52, 129.59, 128.77, 127.27, 125.58, 124.70, 119.05, 113.37, 108.58, 92.81, 65.28, 57.96, 32.90, 28.72, 24.93, 22.55, 20.24, 15.53; LC-MS: ESI 557 (M+H)$^+$.

The free base was dissolved in 2 mL dichloromethane and 0.5 mL methanol. A 1.0 M solution of HCl/ether (0.4 mL, 1.2 equivalent) was added dropwise. After standing for several minutes, a white solid was formed, collected by filtration, washed with ether, and dried under vacuum to give the product as a white solid (0.120 g, 32%).

$^1$H NMR (DMSO-d$_6$) δ 9.6 (s, 1H), 9.05 (s, 1H), 8.70 (s, 1H), 7.92 (s, 1H), 7.9 (d, 1H), 7.78 (d, 2H), 7.55 (d, 2H), 7.45 (d, 1H), 6.53 (s, 1H), 2.74 (m, 8H), 2.05 (m, 2H), 1.65 (m, 2H), 1.5 (m, 4H), 1.30 (s, 9H); LC-MS: ESI 557 (M+H)$^+$.

Example 16

Preparation of 1-(5-tert-Butyl-isoxazol-3-yl)-3-{4-[7-(2-morpholin-4-yl-ethyl)-imidazo[2,1-b][1,3]benzothiazol-2-yl]-phenyl}-urea hydrochloride [Compound D5]

A. Preparation of the intermediate methyl[2-(4-nitro-phenyl)-imidazo[2,1-b][1,3]benzothiazol-7-yl]-acetic acid: To a suspension of methyl[2-(4-Nitrophenyl)imidazo[2,1-b][1,3] benzothiazol-7-yl]acetate from Example 8C (4.51 g, 12.28 mmol) in THF (60 mL) was added LiOH.H$_2$O (2.727 g, 65 mmol) and water (30 mL). The mixture was stirred at room temperature for two hours. After removal of THF, the aqueous phase was acidified with 10% HCl solution to pH 6. A yellow solid was collected by trituration, and washed with water and dried under high vacuum with P$_2$O$_5$ (4.249 g, 98%). $^1$H NMR (DMSO-d$_6$) δ 9.02 (s, 1H), 8.27 (d, 2H), 8.09 (d, 2H), 8.88 (s and d, 2H), 7.43 (d, 1H), 3.56 (s, 2H).

B. Preparation of the intermediate 1-morpholin-4-yl-2-[2-(4-nitro-phenyl)-imidazo[2,1-b][1,3]benzothiazol-7-yl]-ethanone: To the intermediate from step A (883 mg, 2.5 mmol) in DMF (14 mL) at room temperature was added N-(3-dimethylaminopropyl)-N'-ethylcarbodiimide hydrochloride (0.767 g, 4 mmol) and 1-hydroxybenzotriazole hydrate (0.540 g, 4 mmol). After stirring for 30 minutes, morpholine (1 mL) was added and stirred at room temperature for 5 hours. The reaction was quenched with 100 mL of water, and the precipitate was collected by filtration, washed with water and dried under vacuum with P$_2$O$_5$ to give a yellow solid (0.908 g, 86%). $^1$H NMR (DMSO-d$_6$) δ 9.05 (s, 1H), 8.31 (d, 2H), 8.12 (d, 2H), 7.94 (d, 1H), 7.88 (s, 1H), 7.43 (d, 1H), 3.87 (s, 2H), 3.56 (m, 6H), 3.48 (m, 2H).

C. To prepare the intermediate 4-[7-(2-morpholin-4-yl-ethyl)-imidazo[2,1-b][1,3]benzothiazol-2-yl]-phenylamine: to a suspension of 1-morpholin-4-yl-2-[2-(4-nitro-phenyl)-benzo[d]imidazo[2,1-b]thiazol-7-yl]-ethanone (0.905 g, 2.14 mmol) in THF (30 mL) at room temperature was dropped a 2.0 M solution of BH$_3$-Me$_2$S in THF (5 mL), and then it was heated at 90° C. for 4 hours. To the reaction was carefully dropped 10% HCl (15 mL) and stirred at room temperature for 10 minutes. It was neutralized with saturated NaHCO$_3$ and extracted with CH$_2$Cl$_2$. Extracts were combined, dried over MgSO$_4$, and concentrated to give a yellow solid.

The yellow solid was suspended in methanol (30 mL) and to it was added Raney nickel (~1.0 g wet). The reaction mixture was shacked under hydrogen (50 psi) for 6 hours. It was filtered with Celite and washed with methanol. The filtration was concentrated to give the product as a solid. $^1$H NMR (DMSO-d$_6$) δ 8.40 (s, 1H), 7.85 (s, 1H), 7.82 (d, 1H), 7.52 (d, 2H), 7.40 (d, 1H), 6.61 (d, 2H), 5.19 (s, 2H), 3.58 (t, 4H), 2.85 (t, 2H), 2.56 (t, 2H), 2.43 (t, 4H).

D. The coupling reaction was performed in the manner described in Example 3E to form the title product and its hydrochloride salt was prepared in the manner described in Example 3F; $^1$H NMR (DMSO-d$_6$) δ 10.8 (br, 1H), 9.66 (s, 1H), 9.20 (s, 1H), 8.71 (s, 1H), 7.97 (d and s, 2H), 7.79 (d, 2H), 7.55 (d, 2H), 7.49 (d, 1H), 6.53 (s, 1H), 4.01 (m, 2H), 3.77 (t, 2H), 3.54 (t, 2H), 3.41 (m, 2H), 3.18 (m, 4H), 1.30 (s, 9H); LC-MS: ESI 545 (M+H)$^+$.

E. The following compounds were made in the manner described in Steps A-D above, using the appropriate amine in Step B:

1-(5-tert-Butyl-isoxazol-3-yl)-3-{4-[7-(2-piperidin-1-yl-ethyl)-imidazo[2,1-b][1,3]benzothiazol-2-yl]-phenyl}urea hydrochloride: $^1$H NMR (DMSO-d$_6$) δ 10.0 (br, 1H), 9.68 (s, 1H), 9.24 (s, 1H), 8.71 (s, 1H), 7.96 (d and s, 2H), 7.78 (d, 2H), 7.55 (d, 2H), 7.49 (d, 1H), 6.53 (s, 1H), 3.52 (m, 2H), 3.33 (m, 2H), 3.17 (m, 2H), 2.92 (m, 2H), 1.77 (m, 5H), 1.45 (m, 1H), 1.30 (s, 9H); LC-MS: ESI 544 (M+H)$^+$. [Compound D6]

1-(5-tert-Butyl-isoxazol-3-yl)-3-(4-{7-[2-(4-ethyl-piperazin-1-yl)-ethyl]-imidazo[2,1-b][1,3]benzothiazol-2-yl}-phenyl)-urea hydrochloride: $^1$H NMR (DMSO-d$_6$) δ 11.3 (br, 1H), 9.64 (s, 1H), 9.14 (s, 1H), 8.69 (s, 1H), 7.96 (d and s, 2H), 7.78 (d, 2H), 7.51 (m, 3H), 6.52 (s, 1H), 3.75 (m, 4H), 3.21 (m, 6H), 2.53 (m, 4H), 1.30 (s, 9H), 1.27 (t, 3H); LC-MS: ESI 573 (M+H)$^+$. [Compound D7]

F. The following compounds were prepared in the manner described in Steps A-D above, except that at Step C, a two-step reduction was carried out in which the reduction of the nitro group occurred first using SnCl$_2$.H$_2$O in ethanol heated to reflux for up to several hours. This reaction was followed by a second reduction of the amide to the tertiary amine with BH$_3$-Me$_2$S in THF.

1-(5-tert-Butyl-isoxazol-3-yl)-3-[4-(7-morpholin-4-ylmethyl-imidazo[2,1-b][1,3]benzothiazol-2-yl)-phenyl]-urea hydrochloride; $^1$H NMR (DMSO-d$_6$) δ 10.7 (br, 1H), 9.58 (s, 1H), 9.09 (s, 1H), 8.68 (s, 1H), 8.12 (s, 1H), 8.01 (d, 1H), 7.73 (m, 3H), 7.48 (d, 2H), 6.46 (s, 1H), 4.39 (s, 2H), 3.88 (m, 2H), 3.66 (m, 2H), 3.22 (m, 2H), 3.10 (m, 2H), 1.24 (s, 9H); LC-MS: ESI 531 (M+H)$^+$. [Compound D8]

1-(5-tert-Butyl-isoxazol-3-yl)-3-{4-[7-(4-ethyl-piperazin-1-ylmethyl)-imidazo[2,1-b][1,3]benzothiazol-2-yl]-phenyl}-urea hydrochloride: $^1$H NMR (DMSO-d$_6$) δ 11.5 (br, 1H), 9.71 (s, 1H), 9.32 (s, 1H), 8.77 (s, 1H), 8.25 (s, 1H), 8.06 (d, 1H), 7.82 (m, 3H), 7.56 (d, 2H), 6.53 (s, 1H), 4.39 (s, 2H), 3.65 (m, 4H), 3.38 (m, 4H), 3.15 (m, 2H), 1.30 (s, 9H), 1.22 (t, 3H); LC-MS: ESI 559 (M+H)$^+$. [Compound D9]

1-(5-tert-Butyl-isoxazol-3-yl)-3-[4-(7-piperidin-1-ylmethyl-imidazo[2,1-b][1,3]benzothiazol-2-yl)-phenyl]urea hydrochloride: $^1$H NMR (DMSO-d$_6$) δ 10.5 (br, 1H), 9.79 (s, 1H), 9.44 (s, 1H), 8.83 (s, 1H), 8.29 (s, 1H), 8.13 (d, 1H), 7.87 (d and s, 3H), 7.62 (d, 2H), 6.60 (s, 1H), 4.44 (s, 2H), 3.40 (m, 2H), 2.95 (m, 2H), 1.84 (m, 5H), 1.45 (m, 1H), 1.37 (s, 9H); LC-MS: ESI 529 (M+H)$^+$. [Compound D10]

Example 17

Preparation of Morpholine-4-carboxylic acid {4-[7-(3-morpholin-4-yl-3-oxo-propyl)-benzo[d]imidazo[21-b]thiazol-2-yl]-phenyl}amide [Compound E1]

A. To a suspension of 3-{2-[4-({[(5-tert-butylisoxazol-3-yl)amino]carbonyl}amino)phenyl]imidazo[2,1-b][1,3]benzothiazol-7-yl}propanoic acid (0.504 g, 1 mmol) in CH$_2$Cl$_2$ was added 1.0 M solution of oxalyl chloride in CH$_2$Cl$_2$ (2 mL), and followed by several drops of DMF. After it was stirred at room temperature for 2 hours, solvent was evaporated. To the residue was added CH$_2$Cl$_2$ and morpholine (2 mL) and the mixture was stirred at room temperature for 2 hours. The reaction was quenched with water and CH$_2$Cl$_2$, basified with saturated NaHCO$_3$ solution, and extracted three times with CH$_2$Cl$_2$. The extracts were combined, dried over MgSO$_4$, and concentrated. The crude product was purified by Flash chromatography with 0-10% MeOH/EtOAc as eluant to give the product as white solid (0.126 g). $^1$H NMR (DMSO-d$_6$) δ 8.61 (s, 2H), 7.89 (s, 1H), 7.86 (d, 1H), 7.73 (d, 2H), 7.53 (d, 2H), 7.45 (d, 1H), 3.62 (m, 4H), 3.50 (m, 4H), 3.44 (m, 8H), 2.94 (m, 2H), 2.70 (m, 2H).

Example 18

Preparation of 2-benzo[d]isoxazol-3-yl-N-{4-[7-(2-morpholin-4-yl-ethoxy)-benzo[d]imidazo[2,1-b]thiazol-2-yl]-phenyl}-acetamide A. Benzo[d]isoxazol-3-yl-acetic acid (0.260 g, 1.47 mmol) was dissolved in 10 mL of dry DMF. To this solution was added HOBt (1-hydroxybenzotriazole hydrate, 0.238 g, 1.76 mmol) and EDCl (N-(3-dimethylaminopropyl)-N'-ethylcarbodiimide hydrochloride, 0.338 g, 1.76 mmol). After 20 minutes triethylamine (0.354 g, 0.487 mL, 3.5 mmol) was added followed by the addition of the amine intermediate from Example 3D (0.394 g, 1.50 mmol), the reaction was allowed to stir overnight at room temperature. The solution was then poured into brine, and extracted with ethyl acetate and then CH$_2$Cl$_2$. The combined extracts were dried over magnesium sulfate, filtered and concentrated to a solid. This was purified using silica gel chromatography, with a gradient of 0-10% methanol in CH$_2$Cl$_2$. containing 0.1% triethylamine. The appropriate fractions were collected and concentrated. The solid recrystallized from methanol, CH$_8$Cl$_2$, ethyl acetate. The resulting solid collected by filtration, and dissolved in methanol-CH$_2$Cl$_2$.

B. To this solution from Step A was added 3 mL of 4M HCl/dioxane, and the resulting solution concentrated to a solid. This solid was dissolved in 3 mL of methanol and ethyl ether added until a precipitate formed. This solid was collected by filtration, dried under high vacuum, to give 72 mg of the hydrochloride salt; $^1$H NMR (CDCl$_3$) 7.8 (m, 3H); 7.6 (m, 5H); 4.2 (m, 4H); 3.8 (m, 2H); 3.2 (s, 3H); 3.0 (s, 3H); 3.9 (m, 1H); 2.7 (m, 2H). [Compound E2]

C. The following compounds were prepared in the manner described in Step A using the appropriately substituted carboxylic acid in place of the acetic acid:

2-methyl-4-trifluoromethyl-thiazole-5-carboxylic acid {4-[7-(2-morpholin-4-yl-ethoxy)-benzo[d]imidazo[2,1-b]thiazol-2-yl]-phenyl}-amide; $^1$H NMR (CDCl$_3$) 7.8 (m, 3H); 7.6 (m, 2H); 7.4 (d, 1H); 6.9 (d, 1H); 4.3 (m, 2H), 3.8 (m, 2H); 3.1 (m, 2H); 2.9 (m, 2H); and [Compound E3]

2-(4-chloro-phenyl)-4-methyl-thiazole-5-carboxylic acid {4-[7-(2-morpholin-4-yl-ethoxy)-benzo[d]imidazo[2,1-b]thiazol-2-yl]-phenyl}-amide; $^1$H NMR (CDCl$_3$) 7.8 (m, 2H); 7.9 (s, 1H); 7.8 (d, 1H); 7.7 (d, 1H); 7.7-7.4 (m, 6H); 7.4 (d, 1H); 7.0 (m, 1H); 4.3 (m, 2H); 3.8 (m, 5H); 3.0 (m, 3H); 2.7 (m, 5H). [Compound E4]

Example 19

Preparation of 1-(2,3-Dihydro-benzo[1,4]dioxin-6-yl)-3-{4-[7-(2-morpholin-4-yl-ethoxy)-benzo[d]imidazo[2,1-b]thiazol-2-yl]-phenyl}-urea; [Compound F1]

A. The title compound and the compounds listed in this Section A were obtained using analogous procedures and reagents as described in Example 3E using 7-(2-morpholin-4-yl-ethoxy)-2-(4-amino-phenyl)imidazo[2,1-b][1.3]benzothiazole and the appropriately substituted isocyanate:

Title compound; $^1$H NMR (DMSO-d$_6$) 8.7 (s, 1H); 8.0 (d, 1H); 7.8 (m, 3H); 7.5 (d, 2H); 7.3 (d, 1H); 7.1 (s, 1H); 6.8 (s, 2H); 4.4 (s, 2H); 4.3 (m, 4H); 4.0 (m, 2H); 3.7 (m, 4H); 3.3 (m, 2H); [Compound F1]

1-(4-tert-Butyl-phenyl)-3-{4-[7-(2-morpholin-4-yl-ethoxy)-benzo[d]imidazo[2,1-b]thiazol-2-yl]-phenyl}-urea; $^1$H NMR (DMSO-d$_6$) 11.3 (s, 1H); 9.4 (s, 1H); 9.2 (s, 1H); 8.8 (s, 1H); 8.2 (d, 1H); 7.9 (s, 1H); 7.8 (d, 2H); 7.6 (d, 2H); 7.4 (d, 2H); 7.3 (d, 2H); 4.5 (s, 2H); 3.2 (m, 2H); 1.3 (s, 9H); [Compound F2] 1-benzo[1,3]dioxol-5-yl)-3-{4-[7-(2-morpholin-4-yl-ethoxy)-benzo[d]imidazo[2,1-b]thiazol-2-yl]-phenyl}urea; $^1$H NMR (DMSO-d$_6$) 8.5 (m, 3H); 7.8-7.6 (m, 3H); 7.5 (m, 2H); 7.2 (m, 2H); 6.9 (m, 2H); 5.9 (s, 2H); 4.3 (m, 2H); 3.5 (m, 5H); 2.7 (m, 5H); [Compound F3]

1-(2-methyl-benzothiazol-5-yl)-3-{4-[7-(2-morpholin-4-yl-ethoxy)-benzo[d]imidazo[2,1-b]thiazol-2-yl]-phenyl}-urea; $^1$H NMR (methanol-d$_4$) 8.4 (s, 1H); 8.2 (s, 1H); 7.8 (m, 4H); 7.4 (m, 4H); 7.1 (m, 1H); 4.2 (t, 2H); 3.7 (m, 5H); 2.9 (m, 2H); 2.8 (m, 4H); 1.2 (m, 2H). [Compound F8]

Binding Constant (K$_d$) Measurements for Small-Molecule-Kinase Interactions

Methods for measuring binding affinities for interactions between small molecules and kinases including FLT3, KIT, p38, ABL, VEGFR (also KDR) and EGFR are described in Fabian et al (2005) Nature Biotechnology 23 (3): 329-336, which is incorporated by reference herein. By testing across a large class of protein kinases, specificity of the kinase inhibitors provided herein is also determined. The components of the assays include various human kinases expressed as fusions to T7 bacteriophage particles and immobilized ligands that bind to the ATP site of the kinases. For the assay, phage-displayed kinases and immobilized ATP site ligands are combined with the compound to be tested. If the test compound binds the kinase, it competes with the immobilized ligand and prevents binding to the solid support. If the test compound does not bind the kinase, phage-displayed proteins are free to bind to the solid support through the interaction between the kinase and the immobilized ligand. The results are read out by quantitating the amount of fusion protein bound to the solid support, which is accomplished by either traditional phage plaque assays or by quantitative PCR (qPCR) using the phage genome as a template. To determine the affinity of the interactions between a test molecule and a kinase, the amount of phage-displayed kinase bound to the solid support is quantitated as a function of test compound concentration. The concentration of test molecule that reduces the number of phage bound to the solid support by 50% is equal to the K$_d$ for the interaction between the kinase and the test molecule. Typically, data are collected for twelve concentrations of test compound and the resultant binding curve is fit to a non-cooperative binding isotherm to calculate K$_d$.

Binding affinity values are shown in Table 1 below and are reported as follows: "+" represents binding dissociation constant (Kd) value of 1,000 nM or higher; "++" represents binding dissociation constant (Kd) value of 100 nM to 1,000 nM; "+++" for represents binding dissociation constant (Kd) value of 10 nM to 100 nM; and "++++" represents binding dissociation constant (Kd) value of less than 10 nM.

In Vivo Study

Representative compounds were tested in xenograft mouse model in order to evaluate the in vivo activity at 1, 3 and 10 mg/kg against well established subcutaneous MV4-11 tumors in female athymic nude mice. Xenograft were initiated from MV4-11 human leukemia cells cultured in Iscove's Modified Dulbecco's medium supplemented with 10% heat-inactivated fetal bovine serum, 100 units/mL penicillin G, 100 μg/mL streptomycin sulfate, 0.25 μg/mL amphotericin B, 2 mM glutamine, 0.075% sodium bicarbonate, and 25 μg/mL gentamicin. Tumor cells were maintained in humidified atmosphere of 95% air and 5% CO$_2$ at 37° C. The cells were harvested during logarithmic phase growth and resuspended at a concentration of 5×10$^7$ cells/mL in 50% Matrigel matrix (BD Biosciences) and 50% PBS. MV4-11 cells (1×10$^7$) were implanted subcutaneously into the right flank of each test mouse and the growth of tumors was monitored. Twelve days later, on Day 1 of the study, mice were placed in eight groups each consisting of ten mice with individual tumor sizes of 126 to 221 mm$^3$ and group mean tumor size of 174 mm$^3$, tumor volume calculated as a product of width×width×length in mm of an MV4-11 tumor. The test compounds were formulated for dosing at 10 mL/kg and were administered by oral gavage (p.o.) once daily for twenty-eight days (qd×28). Each dose of drug was given in a volume of 0.2 mL per 20 g of body weight (10 mL/kg) and was adjusted for the body weight of the animal. Each animal was sacrificed when its tumor reached the predetermined endpoint size of 1000 mm$^3$ or on the last day of the study (Day 59), whichever came first. The time to endpoint (TTE) for each mouse was calculated from the following equation: TTE (days)=[log 10(endpoint volume in mm$^3$)–b]/m where b is the intercept and m is the slope of the line obtained by linear regression of a log transformed tumor growth data set. Treatment outcome was determined from tumor growth delay (TGD), defined as the increase in the median time to endpoint (TTE) in a treatment group compared to the control group expressed in days, or as a percentage of the median TTE of the control group. FIG. 1 shows median tumor growth curves generated from the in vivo experiment which demonstrates that a representative compound provided herein produces dose-dependent antitumor activity.

Cellular Proliferation Assay

Cancer cell viability and proliferation can be evaluated using a tetrazolium salt reduction cell-based assay. In viable cells, this colorimetric assay can measure mitochondrial reduction of a tetrazolium component (MTS) into an insoluble formazan product.

MV4-11 is a well-characterized Flt3-dependent human cell line contain internal tandem duplications (ITD) found in patients with acute myeloid leukemia and which express constitutively active Flt3 receptors (Yee et al. Blood (2002)100 (8):2941-2949). This cell line was used to determine the ability of the compounds provided herein to inhibit Flt3 in intact cells. The RS4-11 cell line, which expresses the wild-type (WT) receptor, is also used as a control to verify the test compound's ability to inhibit the FLT3 receptor containing the ITD mutation. MV4-11 cell proliferation was measured after 72 hour incubation with the compounds provided herein, and RS4-11 after 48 hour incubation with the compounds provided herein, in both cases using a standard MTS protocol (Promega Cat #5430 "Cell Titer 96 Aqueous Non-radioactive Cell Proliferation Assay").

MV4-11 cells were plated at 10,000 cells per well in DMEM medium with 0.5% serum. RS4-11 cells were plated at 20,000 cells per well in RPMI with 0.5% serum. The compound plate was set up by aliquoting into column 1 of a 96 well 300 ul polypropylene plate, the negative control (DMSO), aliquoting into column 12 the positive control (an internal compound previously shown to have an IC50 of 64 nM in the MV4-11 assay) and titrating the test compound in serial dilutions into columns 2-11. An aliquot from each well of the compound plate was transferred to the plated cells and then incubated @ 37° C. in 5% CO$_2$ (for 3 days for the MV4-11 cells, 2 days for the RS4-11 cells).

MTS tetrazolium compound (Owen's reagent) was thawed in a H$_2$O bath. 20 μl of MTS tetrazolium was added to each well of optical plate and the cells were incubated @ 37° C. in 5% $CO_2$ for 2 hours. The absorbance measured at 490 nm using Spectramax Plus 384 Absorbance Microplate Reader by Molecular Devices.

Cell proliferation values are measured in terms of concentration of test compound that achieves 50% inhibition of cellular proliferation compared to control ($IC_{50}$) and are reported in Tables 1 and 2 below as follows: "+" represents $IC_{50}$ values of less than 10 nM, "++" represents $IC_{50}$ values of between 10 nM and 100 nM and "+++" represents $IC_{50}$ values of greater than 100 nM.

TABLE 1

| Compound No. | Binding Assay FLT3 $K_d$ (nM) | Cellular Assay MV-proliferation $IC_{50}$ (nM) | Binding Assay KIT $K_d$ (nM) | Binding Assay CSF1R $K_d$ (nM) |
|---|---|---|---|---|
| A1 | ++++ | + | | |
| A2 | +++ | + | | |
| A3 | ++++ | + | | |
| A4 | ++++ | + | | |
| A5 | ++++ | + | | |
| A6 | ++++ | + | | |
| A7 | ++++ | + | | |
| B1 | ++++ | + | ++++ | +++ |
| B2 | ++++ | + | ++++ | |
| B3 | ++++ | + | ++++ | |
| B4 | ++++ | + | ++++ | |
| B5 | ++++ | + | +++ | +++ |
| B6 | ++++ | + | +++ | |
| B7 | ++++ | + | +++ | +++ |
| B8 | ++++ | ++ | +++ | +++ |
| B9 | ++++ | + | +++ | |
| B10 | ++++ | + | +++ | +++ |
| B11 | ++++ | + | +++ | ++ |
| B12 | ++++ | + | +++ | ++ |
| B13 | ++ | +++ | + | + |
| B14 | + | +++ | + | + |
| C1 | ++++ | + | ++++ | |
| C2 | ++++ | + | ++++ | |
| C3 | ++++ | + | +++ | + |
| C4 | ++++ | + | ++++ | +++ |
| C5 | ++++ | + | ++++ | +++ |
| C7 | ++++ | + | ++++ | +++ |
| C8 | ++++ | + | ++++ | +++ |
| C9 | ++++ | + | ++++ | ++++ |
| C10 | ++++ | + | ++++ | +++ |
| C11 | ++++ | + | ++++ | ++++ |
| C12 | ++++ | + | ++++ | +++ |
| C13 | ++++ | + | ++++ | +++ |
| C14 | ++++ | + | ++++ | +++ |
| C15 | ++++ | + | ++++ | +++ |

TABLE 2

| Compound No. | Binding Assay FLT3 $K_d$ (nM) | Cellular Assay MV-proliferation $IC_{50}$ (nM) | Binding Assay KIT $K_d$ (nM) | Binding Assay CSF1R $K_d$ (nM) |
|---|---|---|---|---|
| C16 | ++++ | + | ++++ | +++ |
| C17 | ++++ | + | ++++ | +++ |
| C18 | ++++ | + | ++++ | +++ |
| C19 | ++++ | + | ++++ | +++ |
| C20 | ++++ | + | ++++ | +++ |
| C21 | ++++ | + | ++++ | +++ |
| C22 | ++++ | + | ++++ | +++ |
| C23 | ++++ | + | ++++ | +++ |
| C24 | ++++ | + | ++++ | +++ |
| C25 | ++++ | + | ++++ | +++ |
| C26 | ++++ | + | +++ | ++ |
| C27 | ++++ | + | ++++ | +++ |
| D1 | ++++ | + | ++++ | |
| D2 | +++ | ++ | ++++ | +++ |
| D3 | ++++ | + | ++++ | +++ |
| D4 | ++++ | + | +++ | +++ |
| D5 | ++++ | + | ++++ | ++++ |
| D6 | ++++ | + | ++++ | ++++ |
| D7 | ++++ | + | ++++ | ++++ |
| D8 | ++++ | + | ++++ | +++ |
| D9 | ++++ | + | ++++ | +++ |
| D10 | ++++ | + | ++++ | +++ |
| E1 | ++ | +++ | + | + |
| E2 | ++++ | + | +++ | + |
| E3 | + | +++ | + | + |
| E4 | +++ | ++ | ++ | ++ |
| F1 | ++++ | + | ++++ | ++ |
| F2 | ++++ | + | ++++ | +++ |
| F3 | ++++ | + | ++++ | + |
| F8 | ++++ | + | +++ | ++ |

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound selected from (7-(2-morpholin-4-yl-ethoxy)-2-(4-nitro-phenyl)imidazo[2,1-b][1,3]benzothiazole) and 4-(7-(2-morpholinoethoxy)benzo[d]imidazo[2,1-b]thiazol-2-yl)aniline.

* * * * *